(12) United States Patent
Witschel et al.

(10) Patent No.: US 7,687,435 B2
(45) Date of Patent: Mar. 30, 2010

(54) BENZOYL-SUBSTITUTED PHENYLALANINEAMIDES

(75) Inventors: Matthias Witschel, Bad Duerkheim (DE); Michael Puhl, Lampertheim (DE); Gerhard Hamprecht, Weinheim (DE); Liliana Parra Rapado, Offenburg (DE); Ulf Misslitz, Neustadt (DE); CyrilL Zagar, Mannheim (DE); Peter Plath, Frankenthal (DE); Robert Reinhard, Ludwigshafen (DE); Bernd Sievernich, Hassloch (DE); Rex Liebl, Deidesheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 700 days.

(21) Appl. No.: 10/581,444

(22) PCT Filed: Dec. 17, 2004

(86) PCT No.: PCT/EP2004/014392

§ 371 (c)(1),
(2), (4) Date: Jun. 2, 2006

(87) PCT Pub. No.: WO2005/061443

PCT Pub. Date: Jul. 7, 2005

(65) Prior Publication Data

US 2007/0142230 A1    Jun. 21, 2007

(30) Foreign Application Priority Data

Dec. 19, 2003    (DE) ................ 103 60 395

(51) Int. Cl.
*A01N 37/18* (2006.01)
*C07C 237/42* (2006.01)
(52) U.S. Cl. ...................... 504/335; 564/155
(58) Field of Classification Search ............ 504/335; 564/152

See application file for complete search history.

(56) References Cited

U.S. PATENT DOCUMENTS 4,004,008 A    1/1977    Makovec et al.
2004/0229955 A1 *  11/2004   Andersen et al. ........... 514/616

FOREIGN PATENT DOCUMENTS

| CA | 2 474 354 A1 | 8/2003 |
|---|---|---|
| GB | 2 369 117 A | 5/2002 |
| JP | 3-294253 A | 12/1991 |
| JP | 10-298151 | 11/1998 |
| WO | WO 97/05865 A1 | 2/1997 |

OTHER PUBLICATIONS

Patani et al., Bioisosterism: A Rational Approach in Drug Design, 1996, Chem. Rev., 96, p. 3149.*

Sawamura et al., Gold(I)-Catalyzed Asymmetric Aldol Reaction of N-Methoxy-N-methyl-alpha-isocyanoacetamide (alpha-Isocyano Weinreb Amide). An Efficient Synthesis of Optically Active beta-Hydroxy alpha-Amino Aldehydes and Ketones, 1995, J. Org. Chem., 60, pp. 1727 and 1728.*

Zupancic et al., Reductive Ring Cleavage of 1-Alkyl-4-benzoylamino-5-phenyl-3-pyrazolidinones with Raney-Nickel Alloy. Synthesis of N-Benzoyl-3-alkylamino-3-phenylalanine Amides from rel-(4R,5R)-4-Benzoylamino-5-phenyl-3-pyrazolidinone, 1999, J. Heterocyclic Chem., 36, p. 607.*

Soloshonok et al., "Gold(I)-Catalyzed Asymmetric Aldol Reactions of Fluorinated Benzaldehydes with an α-Isocyanoacetamide", Tetrahedron:Asymmetry, vol. 5, No. 6, pp. 1091-1094, 1994. Chemical Abstract, Accession No. XP-002329711.

Soloshonok et al., Gold(I)-Catalyzed Asymmetric Aldol Reaction of Methyl Isocyanoacetate with Fluorinated Benzaldehydes, Tetrahedron Letters, vol. 35, No. 17, pp. 2713-2716, 1994, Chemical Abstract, Accession No. XP-002329712.

Jommi et al., "Asymmetric Synthesis of β-Hydroxy-α-amino acids by condensation of aliphatic and aromatic aldehydes . . . ", Gazzetta Chimica Italiana, vol. 124, 1994, pp. 299-300, Chemical Abstract, Accession No. XP-002329713.

Soloshonok et al., "Transition Metal/Base-Catalyzed Aldol Reactions of Isocyanoacetic Acid Derivatives . . . ", J. Org. Chem, 1997, vol. 62, pp. 3470-3479, Chemical Abstract, Accession No. XP-002329714.

Sheehan and Ryan, The synthesis of substituted penicillins and simpler structural analogs. I. Alpha amino monocyclic B-lactams. Journal of the American Chemical Society, 1951, 1204-1206, 73.

* cited by examiner

*Primary Examiner*—Kamal A Saeed
*Assistant Examiner*—Kristin Bianchi
(74) *Attorney, Agent, or Firm*—Rothwell, Figg, Ernst & Manbeck, P.C.

(57) ABSTRACT

The present invention relates to benzoyl-substituted phenylalanineamides of the formula I

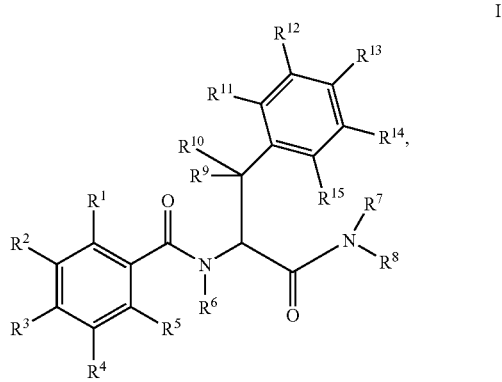

in which the variables $R^1$ to $R^{15}$ are as defined in the description,
and to their agriculturally useful salts,
to processes and intermediates for their preparation and to the use of these compounds or of compositions comprising these compounds for controlling unwanted plants.

13 Claims, No Drawings

BENZOYL-SUBSTITUTED PHENYLALANINEAMIDES

CROSS REFERENCE TO RELATED APPLICATION

This application is a 35 USC §371 National Phase Entry Application from PCT/EP2004/014392, filed Dec. 17, 2004, and designating the United States.

The present invention relates to benzoyl-substituted phenylalanineamides of the formula I

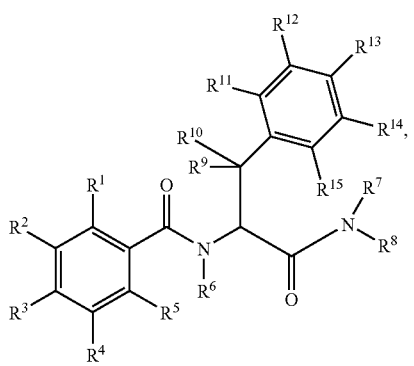

in which the variables are as defined below:
- $R^1$ is halogen, cyano, $C_1$-$C_6$-alkyl, $C_1$-$C_6$-haloalkyl, $C_1$-$C_6$-haloalkoxy, nitro, hydroxycarbonyl, $C_1$-$C_6$-alkoxycarbonyl, $C_1$-$C_6$-haloalkylthio or phenyl;
- $R^2$, $R^3$, $R^4$, $R^5$ are hydrogen, halogen, cyano, $C_1$-$C_6$-alkyl, $C_1$-$C_6$-haloalkyl, $C_1$-$C_6$-alkoxy, $C_1$-$C_6$-haloalkoxy, nitro, amino, $C_1$-$C_6$-alkylamino, di($C_1$-$C_6$-alkyl)amino, $C_1$-$C_6$-alkylthio or $C_1$-$C_6$-alkoxycarbonyl;
- $R^6$, $R^7$ are hydrogen, hydroxyl or $C_1$-$C_6$-alkoxy;
- $R^8$ is $C_1$-$C_6$-alkyl, $C_1$-$C_4$-cyanoalkyl or $C_1$-$C_6$-haloalkyl;
- $R^9$ is $OR^{16}$, $SR^{17}$ or $NR^{18}R^{19}$;
- $R^{10}$ is hydrogen or $C_1$-$C_6$-alkyl;
- $R^{11}$, $R^{12}$ are hydrogen, halogen, cyano, $C_1$-$C_6$-alkyl, $C_1$-$C_6$-haloalkyl, hydroxyl, $C_1$-$C_6$-alkoxy, $C_1$-$C_6$-haloalkoxy, hydroxyl, nitro, hydroxy-$C_1$-$C_4$-alkyl, $C_1$-$C_6$-alkoxy-$C_1$-$C_4$-alkyl, tri($C_1$-$C_6$-alkyl)silyloxy-$C_1$-$C_4$-alkyl, $C_1$-$C_4$-alkylthio, (hydroxycarbonyl)-$C_1$-$C_6$-alkyl, ($C_1$-$C_6$-alkoxycarbonyl)-$C_1$-$C_6$-alkyl, (hydroxycarbonyl)-$C_2$-$C_6$-alkenyl, ($C_1$-$C_6$-alkoxycarbonyl)-$C_2$-$C_6$-alkeynl, (hydroxycarbonyl)-$C_1$-$C_4$-alkoxy, ($C_1$-$C_4$-alkoxycarbonyl)-$C_1$-$C_4$-alkoxy, ($C_1$-$C_4$-alkylcarbonyl)oxy-$C_1$-$C_4$-alkyl, hydroxycarbonyl-$C_1$-$C_4$-alkoxy-$C_1$-$C_4$-alkyl, ($C_1$-$C_4$-alkylsulfonyl)oxy-$C_1$-$C_4$-alkyl, $C_1$-$C_4$-alkyl-O—C(O)—[$C_1$-$C_4$-alkyl-O]$_3$—$C_1$-$C_4$-alkyl, carbamoyloxy-$C_1$-$C_4$-alkyl, ($C_1$-$C_4$-alkylaminocarbonyl)oxy-$C_1$-$C_4$-alkyl, [di($C_1$-$C_4$-alkyl)aminocarbonyl]oxy-$C_1$-$C_4$-alkyl, [($C_1$-$C_4$-haloalkylsulfonyl)aminocarbonyl]oxy-$C_1$-$C_4$-alkyl, benzyloxy, where the phenyl ring may be substituted by 1 to 3 radicals from the group consisting of halogen and $C_1$-$C_4$-alkyl, amino, $C_1$-$C_4$-alkylamino, di($C_1$-$C_4$-alkyl)amino, $C_1$-$C_4$-alkylsulfonylamino, $C_1$-$C_4$-haloalkylsulfonylamino, $C_1$-$C_4$-alkylcarbonylamino, carbamoylamino, ($C_1$-$C_4$-alkylamino)carbonylamino, [di($C_1$-$C_4$-alkyl)amino]carbonylamino, [($C_1$-$C_4$-haloalkylsulfonyl)aminocarbonyl]-amino, phenyl or heterocyclyl, where the phenyl and the heterocyclyl radical of the two last-mentioned substituents may carry 1 to 3 radicals from the following group: halogen, nitro, $C_1$-$C_4$-alkyl, $C_1$-$C_4$-haloalkyl, hydroxycarbonyl and $C_1$-$C_6$-alkoxycarbonyl;
- $R^{13}$, $R^{14}$, $R^{15}$ are hydrogen, halogen, cyano, $C_1$-$C_6$-alkyl, $C_1$-$C_6$-haloalkyl, $C_1$-$C_6$-alkoxy, $C_1$-$C_6$-haloalkoxy, hydroxyl, nitro, $C_1$-$C_4$-alkylthio or benzyloxy;
- $R^{16}$, $R^{17}$, $R^{18}$ are hydrogen, $C_1$-$C_6$-alkyl, tri($C_1$-$C_6$-alkyl)silyl, $C_3$-$C_6$-cycloalkyl, $C_3$-$C_6$-alkenyl, $C_3$-$C_6$-alkynyl, $C_3$-$C_6$-haloalkenyl, $C_3$-$C_6$-haloalkynyl, formyl, $C_1$-$C_6$-alkylcarbonyl, $C_3$-$C_6$-cycloalkylcarbonyl, $C_2$-$C_6$-alkenylcarbonyl, $C_2$-$C_6$-alkynylcarbonyl, $C_1$-$C_6$-alkoxycarbonyl, $C_3$-$C_6$-alkenyloxycarbonyl, $C_3$-$C_6$-alkynyloxycarbonyl, $C_1$-$C_6$-alkylaminocarbonyl, $C_3$-$C_6$-alkenylaminocarbonyl, $C_3$-$C_6$-alkynylaminocarbonyl, $C_1$-$C_6$-alkylsulfonylaminocarbonyl, $C_1$-$C_6$-haloalkylsulfonylaminocarbonyl, di($C_1$-$C_6$-alkyl)aminocarbonyl, N—($C_3$-$C_6$-alkenyl)-N—($C_1$-$C_6$-alkyl)aminocarbonyl, N—($C_3$-$C_6$-alkynyl)-N—($C_1$-$C_6$-alkyl)aminocarbonyl, N—($C_1$-$C_6$-alkoxy)-N—($C_1$-$C_6$-alkyl)aminocarbonyl, N—($C_3$-$C_6$-alkenyl)-N—($C_1$-$C_6$-alkoxy)aminocarbonyl, N—($C_3$-$C_6$-alkynyl)-N—($C_1$-$C_6$-alkoxy)aminocarbonyl, di($C_1$-$C_6$-alkyl)aminothiocarbonyl, $C_1$-$C_6$-alkylcarbonyl-$C_1$-$C_6$-alkyl, $C_1$-$C_6$-alkoxyimino-$C_1$-$C_6$-alkyl, N—($C_1$-$C_6$-alkylamino)imino-$C_1$-$C_6$-alkyl or N-(di-$C_1$-$C_6$-alkylamino)imino-$C_1$-$C_6$-alkyl,
  where the alkyl, cycloalkyl and alkoxy radicals mentioned may be partially or fully halogenated and/or may carry 1 to 3 of the following groups: cyano, hydroxyl, $C_3$-$C_6$-cycloalkyl, $C_1$-$C_4$-alkoxy, $C_1$-$C_4$-alkylthio, di($C_1$-$C_4$-alkyl)amino, $C_1$-$C_4$-alkylcarbonyl, hydroxycarbonyl, $C_1$-$C_4$-alkoxycarbonyl, aminocarbonyl, $C_1$-$C_4$-alkylaminocarbonyl, di($C_1$-$C_4$-alkyl)aminocarbonyl or $C_1$-$C_4$-alkylcarbonyloxy;
  phenyl, phenyl-$C_1$-$C_6$-alkyl, phenylcarbonyl, phenylcarbonyl-$C_1$-$C_6$-alkyl, phenoxycarbonyl, phenylaminocarbonyl, phenylsulfonylaminocarbonyl, N—($C_1$-$C_6$-alkyl)-N-(phenyl)aminocarbonyl, phenyl-$C_1$-$C_6$-alkylcarbonyl, heterocyclyl, heterocyclyl-$C_1$-$C_6$-alkyl, heterocyclylcarbonyl, heterocyclylcarbonyl-$C_1$-$C_6$-alkyl, heterocyclyloxycarbonyl, heterocyclylaminocarbonyl, heterocyclylsulfonylaminocarbonyl, N—($C_1$-$C_6$-alkyl)-N-(heterocyclyl)aminocarbonyl or heterocyclyl-$C_1$-$C_6$-alkylcarbonyl,
  where the phenyl and the heterocyclyl radical of the 17 last-mentioned substituents may be partially or fully halogenated and/or may carry 1 to 3 of the following groups: nitro, cyano, $C_1$-$C_4$-alkyl, $C_1$-$C_4$-haloalkyl, $C_1$-$C_4$-alkoxy or $C_1$-$C_4$-haloalkoxy;
  $SO_2R^{20}$;
  —C(O)—[$C_1$-$C_4$-alkyl-O]$_3$—$C_1$-$C_4$-alkyl; or
  —C(O)—O—$C_1$-$C_4$-alkyl-O-phenyl, where the phenyl radical may optionally be substituted by 1 to 3 radicals from the group consisting of halogen and $C_1$-$C_4$-alkyl;
- $R^{19}$ is hydrogen, $C_1$-$C_6$-alkyl, $C_3$-$C_6$-cycloalkyl, $C_3$-$C_6$-alkenyl, $C_3$-$C_6$-alkynyl, $C_3$-$C_6$-haloalkenyl, $C_3$-$C_6$-haloalkynyl,
  where the alkyl and cycloalkyl radicals mentioned may be partially or fully halogenated and/or may carry 1 to 3 of the following groups: cyano, hydroxyl, $C_3$-$C_6$-cycloalkyl, $C_1$-$C_4$-alkoxy, $C_1$-$C_4$-alkylthio, di($C_1$-$C_4$-alkyl)amino, $C_1$-$C_4$-alkylcarbonyl, hydroxycarbonyl, $C_1$-$C_4$-alkoxycarbonyl, aminocarbonyl, $C_1$-$C_4$-alkylaminocarbonyl, di($C_1$-$C_4$-alkyl)aminocarbonyl or $C_1$-$C_4$-alkylcarbonyloxy; or
  phenyl, phenyl-$C_1$-$C_6$-alkyl, heterocyclyl or heterocyclyl-$C_1$-$C_6$-alkyl, where the phenyl and the heterocyclyl radical of the 4 last-mentioned substituents may be partially or fully halogenated, and/or may carry 1 to 3 of the following groups: nitro, cyano, $C_1$-$C_4$-alkyl, $C_1$-$C_4$-haloalkyl, $C_1$-$C_4$-alkoxy or $C_1$-$C_4$-haloalkoxy;

$R^{20}$ is $C_1$-$C_6$-alkyl, $C_1$-$C_6$-haloalkyl or phenyl,
where the phenyl radical may be partially or fully halogenated and/or may carry 1 to 3 of the following groups: $C_1$-$C_6$-alkyl, $C_1$-$C_6$-haloalkyl or $C_1$-$C_6$-alkoxy;

and to their agriculturally useful salts.

Moreover, the invention relates to processes and intermediates for preparing compounds of the formula I, to compositions comprising them and to the use of these derivatives or of the compositions comprising them for controlling harmful plants.

Herbicidally active phenylalanine derivatives which are unsubstituted in the β-position or may carry unsubstituted or halogen-substituted alkyl, alkenyl or alkynyl radicals are known from the literature, for example from WO 03/066576.

Benzoyl-substituted amino acid amides having pharmaceutical activity are described, inter alia, in WO 97/05865, GB 2369117, JP 10/298151 and JP 03/294253.

However, the herbicidal properties of the prior-art compounds and/or their compatibility with crop plants are not entirely satisfactory. It is therefore an object of the present invention to provide novel, in particular herbicidally active, compounds having improved properties.

We have found that this object is achieved by the benzoyl-substituted phenylalanineamides of the formula I and their herbicidal action.

Furthermore, we have found herbicidal compositions which comprise the compounds I and have very good herbicidal action. Moreover, we have found processes for preparing these compositions and methods for controlling unwanted vegetation using the compounds I.

Depending on the substitution pattern, the compounds of the formula I comprise two or more centers of chirality, in which case they are present as enantiomers or diastereomer mixtures. The invention provides both the pure enantiomers or diastereomers and their mixtures.

The compounds of the formula I may also be present in the form of their agriculturally useful salts, the nature of the salt generally being immaterial. Suitable salts are, in general, the cations or the acid addition salts of those acids whose cations or anions have no adverse effect on the herbicidal action of the compounds I.

Suitable cations are in particular ions of the alkali metals, preferably lithium, sodium and potassium, of the alkaline earth metals, preferably calcium and magnesium, and of the transition metals, preferably manganese, copper, zinc and iron, and also ammonium, where, if desired, one to four hydrogen atoms may be replaced by $C_1$-$C_4$-alkyl, hydroxy-$C_1$-$C_4$-alkyl, $C_1$-$C_4$-alkoxy-$C_1$-$C_4$-alkyl, hydroxy-$C_1$-$C_4$-alkoxy-$C_1$-$C_4$-alkyl, phenyl or benzyl, preferably ammonium, dimethylammonium, diisopropylammonium, tetramethylammonium, tetrabutylammonium, 2-(2-hydroxyeth-1-oxy)eth-1-ylammonium, di(2-hydroxyeth-1-yl)ammonium, trimethylbenzylammonium, furthermore phosphonium ions, sulfonium ions, preferably tri($C_1$-$C_4$-alkyl)sulfonium, and sulfoxonium ions, preferably tri($C_1$-$C_4$alkyl)sulfoxonium.

Anions of useful acid addition salts are primarily chloride, bromide, fluoride, hydrogensulfate, sulfate, dihydrogenphosphate, hydrogenphosphate, nitrate, bicarbonate, carbonate, hexafluorosilicate, hexafluorophosphate, benzoate, and the anions of $C_1$-$C_4$-alkanoic acids, preferably formate, acetate, propionate and butyrate.

The organic moieties mentioned for the substituents $R^1$-$R^{20}$ or as radicals on phenyl or heterocyclyl rings are collective terms for individual enumerations of the specific group members. All hydrocarbon chains, i.e. all alkyl, alkenyl, alkynyl, cyanoalkyl, haloalkyl, haloalkenyl, haloalkynyl, alkoxy, haloalkoxy, alkoxyalkyl, alkylcarbonyl, alkenylcarbonyl, alkynylcarbonyl, alkoxycarbonyl, alkenyloxycarbonyl, alkynyloxycarbonyl, alkylamino, alkylaminocarbonyl, alkenylaminocarbonyl, alkynylaminocarbonyl, alkylsulfonylaminocarbonyl, dialkylaminocarbonyl, N-alkenyl-N-alkylaminocarbonyl, N-alkynyl-N-alkylaminocarbonyl, N-alkoxy-N-alkylaminocarbonyl, N-alkenyl-N-alkoxyaminocarbonyl, N-alkynyl-N-alkoxyaminocarbonyl, dialkylaminothiocarbonyl, alkylcarbonylalkyl, alkoxyiminoalkyl, N-(alkylamino)iminoalkyl, N-(dialkylamino)iminoalkyl, phenylalkyl, phenylcarbonylalkyl, N-alkyl-N-phenylaminocarbonyl, phenylalkylcarbonyl, heterocyclylalkyl, heterocyclylcarbonylalkyl, N-alkyl-N-heterocyclylaminocarbonyl, heterocyclylalkylcarbonyl, alkylthio and alkylcarbonyloxy moieties, may be straight-chain or branched.

Unless indicated otherwise, halogenated substituents preferably carry one to five identical or different halogen atoms. The term halogen denotes in each case fluorine, chlorine, bromine or iodine.

Examples of other meanings are:

$C_1$-$C_4$-alkyl and the alkyl moieties of $C_1$-$C_6$-alkyliminooxy-$C_1$-$C_4$-alkyl, hydroxy($C_1$-$C_4$-alkyl), tri($C_1$-$C_6$-alkyl)silyloxy-$C_1$-$C_4$-alkyl, ($C_1$-$C_4$-alkylcarbonyl)oxy-$C_1$-$C_4$-alkyl, hydroxycarbonyl-$C_1$-$C_4$-alkoxy-$C_1$-$C_4$-alkyl, ($C_1$-$C_4$-alkylsulfonyl)oxy-$C_1$-$C_4$-alkyl, $C_1$-$C_4$-alkyl-O—C(O)—[$C_1$-$C_4$-alkyl-O]$_3$—$C_1$-$C_4$-alkyl, carbamoyloxy-$C_1$-$C_4$-alkyl, ($C_1$-$C_4$-alkylaminocarbonyl)oxy-$C_1$-$C_4$-alkyl, [di($C_1$-$C_4$-alkyl)aminocarbonyl]oxy-$C_1$-$C_4$-alkyl, [($C_1$-$C_4$-haloalkylsulfonyl)aminocarbonyl]oxy-$C_1$-$C_4$-alkyl, $C_1$-$C_4$-alkylsulfonylamino, —C(O)—[$C_1$-$C_4$-alkyl-O]$_3$—$C_1$-$C_4$-alkyl, —C(O)—O—$C_1$-$C_4$-alkyl-O-phenyl: for example methyl, ethyl, n-propyl, 1-methylethyl, n-butyl, 1-methylpropyl, 2-methylpropyl and 1,1-dimethylethyl;

$C_1$-$C_6$-alkyl and the alkyl moieties of $C_1$-$C_6$-alkylsulfonylaminocarbonyl, N—($C_3$-$C_6$-alkenyl)-N—($C_1$-$C_6$-alkyl)aminocarbonyl, ($C_3$-$C_6$-alkynyl)-N—($C_1$-$C_6$-alkyl)aminocarbonyl, N—($C_1$-$C_6$-alkoxy)-N—($C_1$-$C_6$-alkyl)aminocarbonyl, $C_1$-$C_6$-alkylcarbonyl-$C_1$-$C_6$-alkyl, $C_1$-$C_6$-alkoxyimino-$C_1$-$C_6$-alkyl, N—($C_1$-$C_6$-alkylamino)imino-$C_1$-$C_6$-alkyl, N-(di-$C_1$-$C_6$-alkylamino)imino-$C_1$-$C_6$-alkyl, phenyl-$C_1$-$C_6$-alkyl, phenylcarbonyl-$C_1$-$C_6$-alkyl, N—($C_1$-$C_6$-alkyl)-N-phenylaminocarbonyl, heterocyclyl-$C_1$-$C_6$-alkyl, heterocyclylcarbonyl-$C_1$-$C_6$-alkyl, N—($C_1$-$C_6$-alkyl)-N-heterocyclylaminocarbonyl, tri($C_1$-$C_6$-alkyl)silyloxy-$C_1$-$C_4$-alkyl, tri($C_1$-$C_6$-alkyl)silyl, (hydroxycarbonyl)-$C_1$-$C_6$-alkyl, ($C_1$-$C_6$-alkoxy-carbonyl)-$C_1$-$C_6$-alkyl:

$C_1$-$C_4$-alkyl as mentioned above, and also, for example, n-pentyl, 1-methyl-butyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-di-methylbutyl, 2,2-dimethylbutyl, 2,3-dimethylbutyl, 3,3-dimethylbutyl, 1-ethyl-butyl, 2-ethylbutyl, 1,1,2-trimethylpropyl, 1-ethyl-1-methylpropyl and 1-ethyl-3-methylpropyl;

$C_1$-$C_4$-alkylcarbonyl and the alkylcarbonyl moieties of ($C_1$-$C_4$-alkylcarbonyl)oxy, ($C_1$-$C_4$-alkylcarbonyl)oxy- $C_1$-$C_4$-alkyl, $C_1$-$C_4$-alkylcarbonylamino: for example methylcarbonyl, ethylcarbonyl, propylcarbonyl, 1-methylethylcarbonyl, butylcarbonyl, 1-methylpropylcarbonyl, 2-methylpropylcarbonyl or 1,1-dimethylethylcarbonyl;

$C_1$-$C_6$-alkylcarbonyl, and the alkylcarbonyl radicals of $C_1$-$C_6$-alkylcarbonyl-$C_1$-$C_6$-alkyl, phenyl-$C_1$-$C_6$-alkylcarbonyl and heterocyclyl-$C_1$-$C_6$-alkylcarbonyl: $C_1$-$C_4$-alkylcarbonyl as mentioned above, and also, for example, pentylcarbonyl, 1-methylbutylcarbonyl, 2-methylbutylcarbonyl, 3-methylbutylcarbonyl, 2,2-dimethylpropylcarbonyl, 1-ethylpropylcarbonyl, hexylcarbonyl, 1,1-dimethylpropylcarbonyl, 1,2-dimethylpropylcarbonyl, 1-methylpentylcarbonyl, 2-methylpentylcarbonyl, 3-methylpentylcarbonyl, 4-methylpentylcarbonyl, 1,1-dimethylbutylcarbonyl, 1,2-dimethylbutylcarbonyl, 1,3-dimethylbutylcarbonyl, 2,2-dimethylbutylcarbonyl, 2,3-dimethylbutylcarbonyl, 3,3-dimethylbutylcarbonyl, 1-ethylbutylcarbonyl, 2-ethylbutylcarbonyl, 1,1,2-trimethylpropylcarbonyl, 1,2,2-trimethylpropylcarbonyl, 1-ethyl-1-methylpropylcarbonyl or 1-ethyl-2-methylpropylcarbonyl;

$C_3$-$C_6$-cycloalkyl and the cycloalkyl moieties of $C_3$-$C_6$-cycloalkylcarbonyl: monocyclic saturated hydrocarbons having 3 to 6 ring members, such as cyclopropyl, cyclobutyl, cyclopentyl and cyclohexyl;

$C_3$-$C_6$-alkenyl and the alkenyl moieties of $C_3$-$C_6$-alkenyloxycarbonyl, $C_3$-$C_6$-alkenylaminocarbonyl, N—($C_3$-$C_6$-alkenyl)-N—($C_1$-$C_6$-alkyl)aminocarbonyl and N—($C_3$-$C_6$-alkenyl)-N—($C_1$-$C_6$-alkoxy)aminocarbonyl: for example 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

$C_2$-$C_6$-alkenyl and the alkenyl moieties of $C_2$-$C_6$-alkenylcarbonyl, (hydroxycarbonyl)-$C_2$-$C_6$-alkenyl, ($C_1$-$C_6$-alkoxycarbonyl)-$C_2$-$C_6$-alkenyl: $C_3$-$C_6$-alkenyl as mentioned above, and also ethenyl;

$C_3$-$C_6$-alkynyl and the alkynyl moieties of $C_3$-$C_6$-alkynyloxycarbonyl, $C_3$-$C_6$-alkynylaminocarbonyl, N—($C_3$-$C_6$-alkynyl)-N—($C_1$-$C_6$-alkyl)aminocarbonyl, N—($C_3$-$C_6$-alkynyl)-N—($C_1$-$C_6$-alkoxy)aminocarbonyl: for example 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

$C_2$-$C_6$-alkynyl and the alkynyl moieties of $C_2$-$C_6$-alkynylcarbonyl: $C_3$-$C_6$-alkynyl as mentioned above, and also ethynyl;

$C_1$-$C_4$-cyanoalkyl: for example cyanomethyl, 1-cyanoeth-1-yl, 2-cyanoeth-1-yl, 1-cyanoprop-1-yl, 2-cyanoprop-1-yl, 3-cyanoprop-1-yl, 1-cyanoprop-2-yl, 2-cyanoprop-2-yl, 1-cyanobut-1-yl, 2-cyanobut-1-yl, 3-cyanobut-1-yl, 4-cyanobut-1-yl, 1-cyanobut-2-yl, 2-cyanobut-2-yl, 1-cyanobut-3-yl, 2-cyanobut-3-yl, 1-cyano-2-methylprop-3-yl, 2-cyano-2-methylprop-3-yl, 3-cyano-2-methylprop-3-yl and 2-cyanomethylprop-2-yl;

$C_1$-$C_4$-haloalkyl and the haloalkyl radicals of [(($C_1$-$C_4$-haloalkylsulfonyl)-aminocarbonyl]oxy-$C_1$-$C_4$-alkyl, $C_1$-$C_4$-haloalkylsulfonylamino, [($C_1$-$C_4$-haloalkylsulfonyl)aminocarbonyl]amino: a $C_1$-$C_4$-alkyl radical as mentioned above which is partially or fully substituted by fluorine, chlorine, bromine and/or iodine, i.e., for example, chloromethyl, dichloromethyl, trichloromethyl, fluoromethyl, difluoromethyl, trifluoromethyl, chlorofluoromethyl, dichlorofluoromethyl, chlorodifluoromethyl, bromomethyl, iodomethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl and nonafluorobutyl;

$C_1$-$C_6$-haloalkyl and the haloalkyl radicals of $C_1$-$C_6$-haloalkyl-sulfonylaminocarbonyl, $C_1$-$C_6$-haloalkylthio: $C_1$-$C_4$-haloalkyl as mentioned above, and also, for example, 5-fluoropentyl, 5-chloropentyl, 5-bromopentyl, 5-iodopentyl, undecafluoropentyl, 6-fluorohexyl, 6-chlorohexyl, 6-bromohexyl, 6-iodohexyl and dodecafluorohexyl;

$C_3$-$C_6$-haloalkenyl: a $C_3$-$C_6$-alkenyl radical as mentioned above which is partially or fully substituted by fluorine, chlorine, bromine and/or iodine, for example 2-chloroprop-2-en-1-yl, 3-chloroprop-2-en-1-yl, 2,3-dichloroprop-2-en-1-yl, 3,3-dichloroprop-2-en-1-yl, 2,3,3-trichloro-2-en-1-yl, 2,3-dichlorobut-2-en-1-yl, 2-bromoprop-2-en-1-yl, 3-bromoprop-2-en-1-yl, 2,3-dibromoprop-2-en-1-yl, 3,3-dibromoprop-2-en-1-yl, 2,3,3-tribromo-2-en-1-yl or 2,3-dibromobut-2-en-1-yl;

$C_3$-$C_6$-haloalkynyl: a $C_3$-$C_6$-alkynyl radical as mentioned above which is partially or fully substituted by fluorine, chlorine, bromine and/or iodine, for example 1,1-difluoroprop-2-yn-1-yl, 3-iodoprop-2-yn-1-yl, 4-fluorobut-2-yn-1-yl, 4-chlorobut-2-yn-1-yl, 1,1-difluorobut-2-yn-1-yl, 4-iodobut-3-yn-1-yl, 5-fluoropent-3-yn-1-yl, 5-iodopent-4-yn-1-yl, 6-fluorohex-4-yn-1-yl or 6-iodohex-5-yn-1-yl;

$C_1$-$C_4$-alkoxy and the alkoxy moieties of ($C_1$-$C_4$-alkoxycarbonyl)-$C_1$-$C_4$-alkoxy, hydroxycarbonyl-$C_1$-$C_4$-alkoxy-$C_1$-$C_4$-alkyl, (hydroxycarbonyl)-$C_1$-$C_4$-alkoxy: for example methoxy, ethoxy, propoxy, 1-methylethoxy, butoxy, 1-methylpropoxy, 2-methylpropoxy and 1,1-dimethylethoxy; $C_1$-$C_6$-alkoxy and the alkoxy moieties of N—($C_1$-$C_6$-alkoxy)-N—($C_1$-$C_6$-alkyl)aminocarbonyl, N—($C_3$-$C_6$-alkenyl)-N—($C_1$-$C_6$-alkoxy)aminocarbonyl, N—($C_3$-$C_6$-alkynyl)-N—($C_1$-$C_6$-alkoxy)aminocarbonyl and $C_1$-$C_6$-alkoxyimino-$C_1$-$C_6$-alkyl: $C_1$-$C_4$-alkoxy as mentioned above, and also, for example, pentoxy, 1-methylbutoxy, 2-methylbutoxy, 3-methoxylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy;

$C_1$-$C_4$-haloalkoxy: a $C_1$-$C_4$-alkoxy radical as mentioned above which is partially or fully substituted by fluorine, chlorine, bromine and/or iodine, i.e., for example, fluoromethoxy, difluoromethoxy, trifluoromethoxy, chlorodifluoromethoxy, bromodifluoromethoxy, 2-fluoroethoxy, 2-chloroethoxy, 2-bromomethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2-chloropropoxy, 3-chloropropoxy, 2-bromopropoxy, 3-bromopropoxy, 2,2-difluoropropoxy, 2,3-difluoropropoxy, 2,3-dichloropropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy and nonafluorobutoxy;

$C_1$-$C_6$-haloalkoxy: $C_1$-$C_4$-haloalkoxy as mentioned above, and also, for example, 5-fluoropentoxy, 5-chloropentoxy, 5-bromopentoxy, 5-iodopentoxy, undecafluoropentoxy, 6-fluorohexoxy, 6-chlorohexoxy, 6-bromohexoxy, 6-iodohexoxy and dodecafluorohexoxy;

$C_1$-$C_6$-alkoxy-$C_1$-$C_4$-alkyl: $C_1$-$C_4$-alkyl which is substituted by $C_1$-$C_6$-alkoxy as mentioned above, i.e., for example, methoxymethyl, ethoxymethyl, propoxymethyl, (1-methylethoxy)methyl, butoxymethyl, (1-methylpropoxy)methyl, (2-methylpropoxy)methyl, (1,1-dimethylethoxy)methyl, 2-(methoxy)ethyl, 2-(ethoxy)ethyl, 2-(propoxy)ethyl, 2-(1-methylethoxy)ethyl, 2-(butoxy)ethyl, 2-(1-methylpropoxy)ethyl, 2-(2-methylpropoxy)ethyl, 2-(1,1-dimethylethoxy)ethyl, 2-(methoxy)propyl, 2-(ethoxy)propyl, 2-(propoxy)propyl, 2-(1-methylethoxy)propyl, 2-(butoxy)propyl, 2-(1-methylpropoxy)propyl, 2-(2-methylpropoxy)propyl, 2-(1,1-dimethylethoxy)propyl, 3-(methoxy)propyl, 3-(ethoxy)propyl, 3-(propoxy)propyl, 3-(1-methylethoxy)propyl, 3-(butoxy)propyl, 3-(1-methylpropoxy)propyl, 3-(2-methylpropoxy)propyl, 3-(1,1-dimethylethoxy)propyl, 2-(methoxy)butyl, 2-(ethoxy)butyl, 2-(propoxy)butyl, 2-(1-methylethoxy)butyl, 2-(butoxy)butyl, 2-(1-methylpropoxy)butyl, 2-(2-methylpropoxy)butyl, 2-(1,1-dimethylethoxy)butyl, 3-(methoxy)butyl, 3-(methoxy)butyl, 3-(ethoxy)butyl, 3-(propoxy)butyl, 3-(1-methylethoxy)butyl, 3-(butoxy)butyl, 3-(1-methylpropoxy)butyl, 3-(2-methylpropoxy)butyl, 3-(1,1-dimethylethoxy)butyl, 4-(methoxy)butyl, 4-(ethoxy)butyl, 4-(propoxy)butyl, 4-(1-methylethoxy)butyl, 4-(butoxy)butyl, 4-(1-methylpropoxy)butyl, 4-(2-methylpropoxy)butyl and 4-(1,1-dimethylethoxy)butyl;

$C_1$-$C_4$-alkoxycarbonyl and the alkoxycarbonyl moieties of $C_1$-$C_4$-alkoxy-$C_1$-$C_4$-alkoxycarbonyl, di-($C_1$-$C_4$-alkyl)amino-$C_1$-$C_4$-alkoxycarbonyl, ($C_1$-$C_4$-alkoxycarbonyl)-$C_1$-$C_4$-alkoxy: for example methoxycarbonyl, ethoxycarbonyl, propoxycarbonyl, 1-methylethoxycarbonyl, butoxycarbonyl, 1-methylpropoxycarbonyl, 2-methylpropoxycarbonyl or 1,1-dimethylethoxycarbonyl;

$C_1$-$C_6$-alkoxycarbonyl and the alkoxycarbonyl moieties of ($C_1$-$C_6$-alkoxycarbonyl)-$C_1$-$C_6$-alkyl, ($C_1$-$C_6$-alkoxycarbonyl)-$C_2$-$C_6$-alkenyl: $C_1$-$C_4$-alkoxycarbonyl as mentioned above, and also, for example, pentoxycarbonyl, 1-methylbutoxycarbonyl, 2-methylbutoxycarbonyl, 3-methylbutoxycarbonyl, 2,2-dimethylpropoxycarbonyl, 1-ethylpropoxycarbonyl, hexoxycarbonyl, 1,1-dimethylpropoxycarbonyl, 1,2-dimethylpropoxycarbonyl, 1-methylpentoxycarbonyl, 2-methylpentoxycarbonyl, 3-methylpentoxycarbonyl, 4-methylpentoxycarbonyl, 1,1-dimethylbutoxycarbonyl, 1,2-dimethylbutoxycarbonyl, 1,3-dimethylbutoxycarbonyl, 2,2-dimethylbutoxycarbonyl, 2,3-dimethylbutoxycarbonyl, 3,3-dimethylbutoxycarbonyl, 1-ethylbutoxycarbonyl, 2-ethylbutoxycarbonyl, 1,1,2-trimethylpropoxycarbonyl, 1,2,2-trimethylpropoxycarbonyl, 1-ethyl-1-methyl-propoxycarbonyl or 1-ethyl-2-methylpropoxycarbonyl;

$C_1$-$C_4$-alkylthio: for example methylthio, ethylthio, propylthio, 1-methylethylthio, butylthio, 1-methylpropylthio, 2-methylpropylthio and 1,1-dimethylethylthio;

$C_1$-$C_6$-alkylthio: $C_1$-$C_4$-alkylthio as mentioned above, and also, for example, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio and 1-ethyl-2-methylpropylthio;

$C_1$-$C_6$-alkylamino and the alkylamino radicals of N—($C_1$-$C_6$-alkylamino)imino-$C_1$-$C_6$-alkyl: for example methylamino, ethylamino, propylamino, 1-methylethylamino, butylamino, 1-methylpropylamino, 2-methylpropylamino, 1,1-dimethylethylamino, pentylamino, 1-methylbutylamino, 2-methylbutylamino, 3-methylbutylamino, 2,2-dimethylpropylamino, 1-ethylpropylamino, hexylamino, 1,1-dimethylpropylamino, 1,2-dimethylpropylamino, 1-methylpentylamino, 2-methylpentylamino, 3-methylpentylamino, 4-methylpentylamino, 1,1-dimethylbutylamino, 1,2-dimethylbutylamino, 1,3-dimethylbutylamino, 2,2-dimethylbutylamino, 2,3-dimethylbutylamino, 3,3-dimethylbutylamino, 1-ethylbutylamino, 2-ethylbutylamino, 1,1,2-trimethylpropylamino, 1,2,2-trimethylpropylamino, 1-ethyl-1-methylpropylamino or 1-ethyl-2-methylpropylamino;

di($C_1$-$C_4$-alkyl)amino: for example N,N-dimethylamino, N,N-diethylamino, N,N-dipropylamino, N,N-di(1-methylethyl)amino, N,N-dibutylamino, N,N-di(1-methylpropyl)amino, N,N-di(2-methylpropyl)amino, N,N-di(1,1-dimethylethyl)amino, N-ethyl-N-methylamino, N-methyl-N-propylamino, N-methyl-N-(1-methylethyl)amino, N-butyl-N-methylamino, N-methyl-N-(1-methylpropyl)amino, N-methyl-N-(2-methylpropyl)amino, N-(1,1-dimethylethyl)-N-methylamino, N-ethyl-N-propylamino, N-ethyl-N-(1-methylethyl)amino, N-butyl-N-ethylamino, N-ethyl-N-(1-methylpropyl)amino, N-ethyl-N-(2-methylpropyl)amino, N-ethyl-N-(1,1-dimethylethyl)amino, N-(1-methylethyl)-N-propylamino, N-butyl-N-propylamino, N-(1-methylpropyl)-N-propylamino, N-(2-methylpropyl)-N-propylamino, N-(1,1-dimethylethyl)-N-propylamino, N-butyl-N-(1-methylethyl)amino, N-(1-methylethyl)-N-(1-methylpropyl)amino, N-(1-methylethyl)-N-(2-methylpropyl)amino, N-(1,1-dimethylethyl)-N-(1-methylethyl)amino, N-butyl-N-(1-methylpropyl)amino, N-butyl-N-(2-methylpropyl)amino, N-butyl-N-(1,1-dimethylethyl)amino, N-(1-methylpropyl)-N-(2-methylpropyl)amino, N-(1,1-dimethylethyl)-N-(1-methylpropyl)amino and N-(1,1-dimethylethyl)-N-(2-methylpropyl)amino;

di($C_1$-$C_6$-alkyl)amino and the dialkylamino radicals of N-(di-$C_1$-$C_6$-alkylamino)imino-$C_1$-$C_6$-alkyl: di($C_1$-$C_4$-alkyl)amino as mentioned above, and also, for example, N,N-dipentylamino, N,N-dihexylamino, N-methyl-N-pentylamino, N-ethyl-N-pentylamino, N-methyl-N-hexylamino and N-ethyl-N-hexylamino;

($C_1$-$C_4$-alkylamino)carbonyl and the (alkylamino)carbonyl moieties of ($C_1$-$C_4$-alkylaminocarbonyl)oxy-$C_1$-$C_4$-alkyl, ($C_1$-$C_4$-alkylamino)carbonylamino: for example methylaminocarbonyl, ethylaminocarbonyl, propylaminocarbonyl, 1-methylethylaminocarbonyl, butylaminocarbonyl, 1-methylpropylaminocarbonyl, 2-methylpropylaminocarbonyl or 1,1-dimethylethylaminocarbonyl;

di($C_1$-$C_4$-alkyl)aminocarbonyl and the di($C_1$-$C_4$)alkylaminocarbonyl moieties of [di($C_1$-$C_4$-alkyl)aminocarbonyl]oxy-$C_1$-$C_4$-alkyl, [di($C_1$-$C_4$-alkyl)amino]carbonyl-amino: for example N,N-dimethylaminocarbonyl, N,N-diethylaminocarbonyl, N,N-di(1-methylethyl)aminocarbonyl, N,N-dipropylaminocarbonyl, N,N-dibutylaminocarbonyl, N,N-di(1-methylpropyl)aminocarbonyl, N,N-di(2-methylpropyl)aminocarbonyl, N,N-di(1,1-dimethylethyl)aminocarbonyl, N-ethyl-N-methylaminocarbonyl, N-methyl-N-propylaminocarbonyl, N-methyl-N-(1-methylethyl)aminocarbonyl, N-butyl-N-methylaminocarbonyl, N-methyl-N-(1-methylpropyl)aminocarbonyl, N-methyl-N-(2-methylpropyl)aminocarbonyl, N-(1,1-dimethylethyl)-N-methylaminocarbonyl, N-ethyl-N-propylaminocarbonyl, N-ethyl-N-(1-methylethyl)aminocarbonyl, N-butyl-N-ethylaminocarbonyl, N-ethyl-N-(1-methylpropyl)aminocarbonyl, N-ethyl-N-(2-methylpropyl)aminocarbonyl, N-ethyl-N-(1,1-dimethylethyl)aminocarbonyl, N-(1-methylethyl)-N-propylaminocarbonyl, N-butyl-N-propylaminocarbonyl, N-(1-methylpropyl)-N-propylaminocarbonyl, N-(2-methylpropyl)-N-propylaminocarbonyl, N-(1,1-dimethylethyl)-N-propylaminocarbonyl, N-butyl-N-(1-methylethyl)aminocarbonyl, N-(1-methylethyl)-N-(1-methylpropyl)aminocarbonyl, N-(1-methylethyl)-N-(2-methylpropyl)aminocarbonyl, N-(1,1-dimethylethyl)-N-(1-methylethyl)aminocarbonyl, N-butyl-N-(1-methylpropyl)aminocarbonyl, N-butyl-N-(2-methylpropyl)aminocarbonyl, N-butyl-N-(1,1-dimethylethyl)aminocarbonyl, N-(1-methylpropyl)-N-(2-methylpropyl)aminocarbonyl, N-(1,1-dimethylethyl)-N-(1-methylpropyl)aminocarbonyl or N-(1,1-dimethylethyl)-N-(2-methylpropyl)aminocarbonyl;

($C_1$-$C_6$-alkylamino)carbonyl: ($C_1$-$C_4$-alkylamino)carbonyl as mentioned above, and also, for example, pentylaminocarbonyl, 1-methylbutylaminocarbonyl, 2-methylbutylaminocarbonyl, 3-methylbutylaminocarbonyl, 2,2-dimethylpropylaminocarbonyl, 1-ethylpropylaminocarbonyl, hexylaminocarbonyl, 1,1-dimethylpropylaminocarbonyl, 1,2-dimethylpropylaminocarbonyl, 1-methylpentylaminocarbonyl, 2-methylpentylaminocarbonyl, 3-methylpentylaminocarbonyl, 4-methylpentylaminocarbonyl, 1,1-dimethylbutylaminocarbonyl, 1,2-dimethylbutylaminocarbonyl, 1,3-dimethylbutylaminocarbonyl, 2,2-dimethylbutylaminocarbonyl, 2,3-dimethylbutylaminocarbonyl, 3,3-dimethylbutylaminocarbonyl, 1-ethylbutylaminocarbonyl, 2-ethylbutylaminocarbonyl, 1,1,2-trimethylpropylaminocarbonyl, 1,2,2-trimethyl-propylaminocarbonyl, 1-ethyl-1-methylpropylaminocarbonyl or 1-ethyl-2-methylpropylaminocarbonyl;

di-($C_1$-$C_6$-alkyl)aminocarbonyl: di-($C_1$-$C_4$-alkyl)aminocarbonyl as mentioned above, and also, for example, N-methyl-N-pentylaminocarbonyl, N-methyl-N-(1-methylbutyl)aminocarbonyl, N-methyl-N-(2-methylbutyl)aminocarbonyl, N-methyl-N-(3-methylbutyl)aminocarbonyl, N-methyl-N-(2,2-dimethylpropyl)aminocarbonyl, N-methyl-N-(1-ethylpropyl)aminocarbonyl, N-methyl-N-hexylaminocarbonyl, N-methyl-N-(1,1-dimethylpropyl)aminocarbonyl, N-methyl-N-(1,2-dimethylpropyl)aminocarbonyl, N-methyl-N-(1-methylpentyl)aminocarbonyl, N-methyl-N-(2-methylpentyl)aminocarbonyl, N-methyl-N-(3-methylpentyl)aminocarbonyl, N-methyl-N-(4-methylpentyl)aminocarbonyl, N-methyl-N-(1,1-dimethylbutyl)aminocarbonyl, N-methyl-N-(1,2-dimethylbutyl)aminocarbonyl, N-methyl-N-(1,3-dimethylbutyl)aminocarbonyl, N-methyl-N-(2,2-dimethylbutyl)aminocarbonyl, N-methyl-N-(2,3-dimethylbutyl)aminocarbonyl, N-methyl-N-(3,3-dimethylbutyl)aminocarbonyl, N-methyl-N-(1-ethylbutyl)aminocarbonyl, N-methyl-N-(2-ethylbutyl)aminocarbonyl, N-methyl-N-(1,1,2-trimethylpropyl)aminocarbonyl, N-methyl-N-(1,2,2-trimethylpropyl)aminocarbonyl, N-methyl-N-(1-ethyl-1-methylpropyl)aminocarbonyl, N-methyl-N-(1-ethyl-2-methylpropyl)aminocarbonyl, N-ethyl-N-pentylaminocarbonyl, N-ethyl-N-(1-methylbutyl)aminocarbonyl, N-ethyl-N-(2-methylbutyl)aminocarbonyl, N-ethyl-N-(3-methylbutyl)aminocarbonyl, N-ethyl-N-(2,2-dimethylpropyl)aminocarbonyl, N-ethyl-N-(1-ethylpropyl)aminocarbonyl, N-ethyl-N-hexylaminocarbonyl, N-ethyl-N-(1,1-dimethylpropyl)aminocarbonyl, N-ethyl-N-(1,2-dimethylpropyl)aminocarbonyl, N-ethyl-N-(1-methylpentyl)aminocarbonyl, N-ethyl-N-(2-methylpentyl)aminocarbonyl, N-ethyl-N-(3-methylpentyl)aminocarbonyl, N-ethyl-N-(4-methylpentyl)aminocarbonyl, N-ethyl-N-(1,1-dimethylbutyl)aminocarbonyl, N-ethyl-N-(1,2-dimethylbutyl)aminocarbonyl, N-ethyl-N-(1,3-dimethylbutyl)aminocarbonyl, N-ethyl-N-(2,2-dimethylbutyl)aminocarbonyl, N-ethyl-N-(2,3-dimethylbutyl)aminocarbonyl, N-ethyl-N-(3,3-dimethylbutyl)

aminocarbonyl, N-ethyl-N-(1-ethylbutyl)aminocarbonyl, N-ethyl-N-(2-ethylbutyl)aminocarbonyl, N-ethyl-N-(1,1,2-trimethylpropyl)aminocarbonyl, N-ethyl-N-(1,2,2-trimethylpropyl)aminocarbonyl, N-ethyl-N-(1-ethyl-1-methylpropyl)aminocarbonyl, N-ethyl-N-(1-ethyl-2-methylpropyl)aminocarbonyl, N-propyl-N-pentylaminocarbonyl, N-butyl-N-pentylaminocarbonyl, N,N-dipentylaminocarbonyl, N-propyl-N-hexylaminocarbonyl, N-butyl-N-hexylaminocarbonyl, N-pentyl-N-hexylaminocarbonyl or N,N-dihexylaminocarbonyl;

di($C_1$-$C_6$-alkyl)aminothiocarbonyl: for example N,N-dimethylaminothiocarbonyl, N,N-diethylaminothiocarbonyl, N,N-di(1-methylethyl)aminothiocarbonyl, N,N-dipropylaminothiocarbonyl, N,N-dibutylaminothiocarbonyl, N,N-di(1-methylpropyl)aminothiocarbonyl, N,N-di(2-methylpropyl)aminothiocarbonyl, N,N-di(1,1-dimethylethyl)aminothiocarbonyl, N-ethyl-N-methylaminothiocarbonyl, N-methyl-N-propylaminothiocarbonyl, N-methyl-N-(1-methylethyl)aminothiocarbonyl, N-butyl-N-methylaminothiocarbonyl, N-methyl-N-(1-methylpropyl)aminothiocarbonyl, N-methyl-N-(2-methylpropyl)aminothiocarbonyl, N-(1,1-dimethylethyl)-N-methylaminothiocarbonyl, N-ethyl-N-propylaminothiocarbonyl, N-ethyl-N-(1-methylethyl)aminothiocarbonyl, N-butyl-N-ethylaminothiocarbonyl, N-ethyl-N-(1-methylpropyl)aminothiocarbonyl, N-ethyl-N-(2-methylpropyl)aminothiocarbonyl, N-ethyl-N-(1,1-dimethylethyl)aminothiocarbonyl, N-(1-methylethyl)-N-propylaminothiocarbonyl, N-butyl-N-propylaminothiocarbonyl, N-(1-methylpropyl)-N-propylaminothiocarbonyl, N-(2-methylpropyl)-N-propylaminothiocarbonyl, N-(1,1-dimethylethyl)-N-propylaminothiocarbonyl, N-butyl-N-(1-methylethyl)aminothiocarbonyl, N-(1-methylethyl)-N-(1-methylpropyl)aminothiocarbonyl, N-(1-methylethyl)-N-(2-methypropyl)aminothiocarbonyl, N-(1,1-dimethylethyl)-N-(1-methylethyl)aminothiocarbonyl, N-butyl-N-(1-methylpropyl)aminothiocarbonyl, N-butyl-N-(2-methylpropyl)aminothiocarbonyl, N-butyl-N-(1,1-dimethylethyl)aminothiocarbonyl, N-(1-methylpropyl)-N-(2-methylpropyl)aminothiocarbonyl, N-(1,1-dimethylethyl)-N-(1-methylpropyl)aminothiocarbonyl, N-(1,1-dimethylethyl)-N-(2-methylpropyl)aminothiocarbonyl, N-methyl-N-pentylaminothiocarbonyl, N-methyl-N-(1-methylbutyl)aminothiocarbonyl, N-methyl-N-(2-methylbutyl)aminothiocarbonyl, N-methyl-N-(3-methylbutyl)aminothiocarbonyl, N-methyl-N-(2,2-dimethylpropyl)aminothiocarbonyl, N-methyl-N-(1-ethylpropyl)aminothiocarbonyl, N-methyl-N-hexylaminothiocarbonyl, N-methyl-N-(1,1-dimethylpropyl)aminothiocarbonyl, N-methyl-N-(1,2-dimethylpropyl)aminothiocarbonyl, N-methyl-N-(1-methylpentyl)-aminothiocarbonyl, N-methyl-N-(2-methylpentyl)aminothiocarbonyl, N-methyl-N-(3-methylpentyl)aminothiocarbonyl, N-methyl-N-(4-methylpentyl)-aminothiocarbonyl, N-methyl-N-(1,1-dimethylbutyl)aminothiocarbonyl, N-methyl-N-(1,2-dimethylbutyl)aminothiocarbonyl, N-methyl-N-(1,3-dimethylbutyl)aminothiocarbonyl, N-methyl-N-(2,2-dimethylbutyl)-aminothiocarbonyl, N-methyl-N-(2,3-dimethylbutyl)aminothiocarbonyl, N-methyl-N-(3,3-dimethylbutyl)aminothiocarbonyl, N-methyl-N-(1-ethyl-butyl)aminothiocarbonyl, N-methyl-N-(2-ethylbutyl)aminothiocarbonyl, N-methyl-N-ethyl-N-(1,1,2-trimethylpropyl)aminothiocarbonyl, N-methyl-N-(1,2,2-trimethylpropyl)aminothiocarbonyl, N-methyl-N-(1-ethyl-1-methyl-propyl)aminothiocarbonyl, N-methyl-N-(1-ethyl-2-methylpropyl)-aminothiocarbonyl, N-ethyl-N-pentylaminothiocarbonyl, N-ethyl-N-(1-methylbutyl)aminothiocarbonyl, N-ethyl-N-(2-methylbutyl)aminothiocarbonyl, N-ethyl-N-(3-methylbutyl)aminothiocarbonyl, N-ethyl-N-(2,2-dimethylpropyl)aminothiocarbonyl, N-ethyl-N-(1-ethylpropyl)aminothiocarbonyl, N-ethyl-N-hexylaminothiocarbonyl, N-ethyl-N-(1,1-dimethylpropyl)aminothiocarbonyl, N-ethyl-N-(1,2-dimethylpropyl)aminothiocarbonyl, N-ethyl-N-(1-methylpentyl)aminothiocarbonyl, N-ethyl-N-(2-methylpentyl)aminothiocarbonyl, N-ethyl-N-(3-methylpentyl)aminothiocarbonyl, N-ethyl-N-(4-methylpentyl)aminothiocarbonyl, N-ethyl-N-(1,1-dimethylbutyl)aminothiocarbonyl, N-ethyl-N-(1,2-dimethylbutyl)aminothiocarbonyl, N-ethyl-N-(1,3-dimethylbutyl)-aminothiocarbonyl, N-ethyl-N-(2,2-dimethylbutyl)aminothiocarbonyl, N-ethyl-N-(2,3-dimethylbutyl)aminothiocarbonyl, N-ethyl-N-(3,3-dimethylbutyl)aminothiocarbonyl, N-ethyl-N-(1-ethylbutyl)aminothiocarbonyl, N-ethyl-N-(2-ethylbutyl)aminothiocarbonyl, N-ethyl-N-(1,1,2-trimethylpropyl)aminothiocarbonyl, N-ethyl-N-(1,2,2-trimethylpropyl)aminothiocarbonyl, N-ethyl-N-(1-ethyl-1-methylpropyl)aminothiocarbonyl, N-ethyl-N-(1-ethyl-2-methylpropyl)aminothiocarbonyl, N-propyl-N-pentylaminothiocarbonyl, N-butyl-N-pentylaminothiocarbonyl, N,N-dipentylaminothiocarbonyl, N-propyl-N-hexylaminothiocarbonyl, N-butyl-N-hexylaminothiocarbonyl, N-pentyl-N-hexylaminothiocarbonyl or N,N-dihexylaminothiocarbonyl;

heterocyclyl and the heterocyclyl moieties of heterocyclyl-$C_1$-$C_6$-alkyl, heterocyclylcarbonyl, heterocyclylcarbonyl-$C_1$-$C_6$-alkyl, heterocyclyloxycarbonyl, heterocyclylaminocarbonyl, heterocyclylsulfonylaminocarbonyl, N—($C_1$-$C_6$-alkyl)-N-(heterocyclyl)aminocarbonyl and heterocyclyl-$C_1$-$C_6$-alkylcarbonyl: a saturated, partially unsaturated or aromatic 5- or 6-membered heterocyclic ring which contains one to four identical or different heteroatoms selected from the group consisting of oxygen, sulfur and nitrogen and which may be attached via carbon or nitrogen, for example 5-membered saturated rings attached via carbon, such as tetrahydrofuran-2-yl, tetrahydrofuran-3-yl, tetrahydrothien-2-yl, tetrahydrothien-3-yl, tetrahydropyrrol-2-yl, tetrahydropyrrol-3-yl, tetrahydropyrazol-3-yl, tetrahydropyrazol-4-yl, tetrahydroisoxazol-3-yl, tetrahydroisoxazol-4-yl, tetrahydroisoxazol-5-yl, 1,2-oxathiolan-3-yl, 1,2-oxathiolan-4-yl, 1,2-oxathiolan-5-yl, tetrahydroisothiazol-3-yl, tetrahydroisothiazol-4-yl, tetrahydroisothiazol-5-yl, 1,2-dithiolan-3-yl, 1,2-dithiolan-4-yl, tetrahydroimidazol-2-yl, tetrahydroimidazol-4-yl, tetrahydrooxazol-2-yl, tetrahydrooxazol-4-yl, tetrahydrooxazol-5-yl, tetrahydrothiazol-2-yl, tetrahydrothiazol-4-yl, tetrahydrothiazol-5-yl, 1,3-dioxolan-2-yl, 1,3-dioxolan-4-yl, 1,3-oxathiolan-2-yl, 1,3-oxathiolan-4-yl, 1,3-oxathiolan-5-yl, 1,3-dithiolan-2-yl, 1,3-dithiolan-4-yl, 1,3,2-dioxathiolan-4-yl;

5-membered saturated rings which are attached via nitrogen, such as: tetrahydropyrrol-1-yl, tetrahydropyrazol-1-yl, tetrahydroisoxazol-2-yl, tetrahydroisothiazol-2-yl, tetrahydroimidazol-1-yl, tetrahydrooxazol-3-yl, tetrahydrothiazol-3-yl;

5-membered partially unsaturated rings which are attached via carbon, such as: 2,3-dihydrofuran-2-yl, 2,3-dihydrofuran-3-yl, 2,5-dihydrofuran-2-yl, 2,5-dihydrofuran-3-yl, 4,5-dihydrofuran-2-yl, 4,5-dihydrofuran-3-yl, 2,3-dihydrothien-2-yl, 2,3-dihydrothien-3-yl, 2,5-dihydrothien-2-yl, 2,5-dihydrothien-3-yl, 4,5-dihydrothien-2-yl, 4,5-dihydrothien-3-yl, 2,3-dihydro-1H-pyrrol-2-yl, 2,3-dihydro-1H-pyrrol-3-yl, 2,5-dihydro-1H-pyrrol-2-yl, 2,5-dihydro-1H-pyrrol-3-yl, 4,5-dihydro-1H-pyrrol-2-yl, 4,5-dihydro-1H-pyrrol-3-yl, 3,4-dihydro-2H-pyrrol-2-yl, 3,4-dihydro-2H-pyrrol-3-yl, 3,4-dihydro-5H-pyrrol-2-yl, 3,4-dihydro-5H-pyrrol-3-yl, 4,5-dihydro-1H-pyrazol-3-yl, 4,5-dihydro-1H-pyrazol-4-yl, 4,5-dihydro-1H-pyrazol-5-yl, 2,5-dihydro-1H-pyrazol-3-yl, 2,5-dihydro-1H-pyrazol-4-yl, 2,5-dihydro-1H-pyrazol-5-yl, 4,5-dihydroisoxazol-3-yl, 4,5-dihydroisoxazol-4-yl, 4,5-dihydroisoxazol-5-yl, 2,5-dihydroisoxazol-3-yl, 2,5-dihydroisoxazol-4-yl, 2,5-dihydroisoxazol-5-yl, 2,3-dihydroisoxazol-3-yl, 2,3-dihydroisoxazol-4-yl, 2,3-dihydroisoxazol-5-yl, 4,5-dihydroisothiazol-3-yl, 4,5-dihydroisothiazol-4-yl, 4,5-dihydroisothiazol-5-yl, 2,5-dihydroisothiazol-3-yl, 2,5-dihydroisothiazol-4-yl, 2,5-dihydroisothiazol-5-yl, 2,3-dihydroisothiazol-3-yl, 2,3-dihydroisothiazol-4-yl, 2,3-dihydroisothiazol-5-yl, $\Delta^3$-1,2-dithiol-3-yl, $\Delta^3$-1,2-dithiol-4-yl, $\Delta^3$-1,2-dithiol-5-yl, 4,5-dihydro-1H-imidazol-2-yl, 4,5-dihydro-1H-imidazol-4-yl, 4,5-dihydro-1H-imidazol-5-yl, 2,5-dihydro-1H-imidazol-2-yl, 2,5-dihydro-1H-imidazol-4-yl, 2,5-dihydro-1H-imidazol-5-yl, 2,3-dihydro-1H-imidazol-2-yl, 2,3-dihydro-1H-imidazol-4-yl, 4,5-dihydrooxazol-2-yl, 4,5-dihydrooxazol-4-yl, 4,5-dihydrooxazol-5-yl, 2,5-dihydrooxazol-2-yl, 2,5-dihydrooxazol-4-yl, 2,5-dihydrooxazol-5-yl, 2,3-dihydrooxazol-2-yl, 2,3-dihydrooxazol-4-yl, 2,3-dihydrooxazol-5-yl, 4,5-dihydrothiazol-2-yl, 4,5-dihydrothiazol-4-yl, 4,5-dihydrothiazol-5-yl, 2,5-dihydrothiazol-2-yl, 2,5-dihydrothiazol-4-yl, 2,5-dihydrothiazol-5-yl, 2,3-dihydrothiazol-2-yl, 2,3-dihydrothiazol-4-yl, 2,3-dihydrothiazol-5-yl, 1,3-dioxol-2-yl, 1,3-dioxol-4-yl, 1,3-dithiol-2-yl, 1,3-dithiol-4-yl, 1,3-oxathiol-2-yl, 1,3-oxathiol-4-yl, 1,3-oxathiol-5-yl, 1,2,3-$\Delta^2$-oxadiazolin-4-yl, 1,2,3-$\Delta^2$-oxadiazolin-5-yl, 1,2,4-$\Delta^4$-oxadiazolin-3-yl, 1,2,4-$\Delta^4$-oxadiazolin-5-yl, 1,2,4-$\Delta^2$-oxadiazolin-3-yl, 1,2,4-$\Delta^2$-oxadiazolin-5-yl, 1,2,4-$\Delta^3$-oxadiazolin-3-yl, 1,2,4-$\Delta^3$-oxadiazolin-5-yl, 1,3,4-$\Delta^2$-oxadiazolin-2-yl, 1,3,4-$\Delta^2$-oxadiazolin-5-yl, 1,3,4-$\Delta^3$-oxadiazolin-2-yl, 1,3,4-oxadiazolin-2-yl, 1,2,4-$\Delta^4$-thiadiazolin-3-yl, 1,2,4-$\Delta^4$-thiadiazolin-5-yl, 1,2,4-$\Delta^3$-thiadiazolin-3-yl, 1,2,4-$\Delta^3$-thiadiazolin-5-yl, 1,2,4-$\Delta^2$-thiadiazolin-3-yl, 1,2,4-$\Delta^2$-thiadiazolin-5-yl, 1,3,4-$\Delta^2$-thiadiazolin-2-yl, 1,3,4-$\Delta^2$-thiadiazolin-5-yl, 1,3,4-$\Delta^3$-thiadiazolin-2-yl, 1,3,4-thiadiazolin-2-yl, 1,2,3-$\Delta^2$-triazolin-4-yl, 1,2,3-$\Delta^2$-triazolin-5-yl, 1,2,4-$\Delta^2$-triazolin-3-yl, 1,2,4-$\Delta^2$-triazolin-5-yl, 1,2,4-$\Delta^3$-triazolin-3-yl, 1,2,4-$\Delta^3$-triazolin-5-yl, 1,2,4-$\Delta^1$-triazolin-2-yl, 1,2,4-triazolin-3-yl, 3H-1,2,4-dithiazol-5-yl, 2H-1,3,4-dithiazol-5-yl, 2H-1,3,4-oxathiazol-5-yl;

5-membered partially unsaturated rings attached via nitrogen, such as: 2,3-dihydro-1H-pyrrol-1-yl, 2,5-dihydro-1H-pyrrol-1-yl, 4,5-dihydro-1H-pyrazol-1-yl, 2,5-dihydro-1H-pyrazol-1-yl, 2,3-dihydro-1H-pyrazol-1-yl, 2,5-dihydroisoxazol-2-yl, 2,3-dihydroisoxazol-2-yl, 2,5-dihydroisothiazol-2-yl, 2,3-dihydroisoxazol-2-yl, 4,5-dihydro-1H-imidazol-1-yl, 2,5-dihydro-1H-imidazol-1-yl, 2,3-dihydro-1H-imidazol-1-yl, 2,3-dihydrooxazol-3-yl, 2,3-dihydrothiazol-3-yl, 1,2,4-$\Delta^4$-oxadiazolin-2-yl, 1,2,4-$\Delta^2$-oxadiazolin-4-yl, 1,2,4-$\Delta^3$-oxadiazolin-2-yl, 1,3,4-$\Delta^2$-oxadiazolin-4-yl, 1,2,4-$\Delta^5$-thiadiazolin-2-yl, 1,2,4-$\Delta^3$-thiadiazolin-2-yl, 1,2,4-$\Delta^2$-thiadiazolin-4-yl, 1,3,4-$\Delta^2$-thiadiazolin-4-yl, 1,2,3-$\Delta^2$-triazolin-1-yl, 1,2,4-$\Delta^2$-triazolin-1-yl, 1,2,4-$\Delta^2$-triazolin-4-yl, 1,2,4-$\Delta^3$-triazolin-1-yl, 1,2,4-$\Delta^1$-triazolin-4-yl;

5-membered aromatic rings which are attached via carbon, such as: 2-furyl, 3-furyl, 2-thienyl, 3-thienyl, pyrrol-2-yl, pyrrol-3-yl, pyrazol-3-yl, pyrazol-4-yl, isoxazol-3-yl, isoxazol-4-yl, isoxazol-5-yl, isothiazol-3-yl, isothiazol-4-yl, isothiazol-5-yl, imidazol-2-yl, imidazol-4-yl, oxazol-2-yl, oxazol-4-yl, oxazol-5-yl, thiazol-2-yl, thiazol-4-yl, thiazol-5-yl, 1,2,3-oxadiazol-4-yl, 1,2,3-oxadiazol-5-yl, 1,2,4-oxadiazol-3-yl, 1,2,4-oxadiazol-5-yl, 1,3,4-oxadiazol-2-yl, 1,2,3-thiadiazol-4-yl, 1,2,3-thiadiazol-5-yl, 1,2,4-thiadiazol-3-yl, 1,2,4-thiadiazol-5-yl, 1,3,4-thiadiazolyl-2-yl, 1,2,3-triazol-4-yl, 1,2,4-triazol-3-yl, tetrazol-5-yl;

5-membered aromatic rings which are attached via nitrogen, such as: pyrrol-1-yl, pyrazol-1-yl, imidazol-1-yl, 1,2,3-triazol-1-yl, 1,2,4-triazol-1-yl, tetrazol-1-yl;

6-membered saturated rings which are attached via carbon, such as: tetrahydropyran-2-yl, tetrahydropyran-3-yl, tetrahydropyran-4-yl, piperidin-2-yl, piperidin-3-yl, piperidin-4-yl, tetrahydrothiopyran-2-yl, tetrahydrothiopyran-3-yl, tetrahydrothiopyran-4-yl, 1,3-dioxan-2-yl, 1,3-dioxan-4-yl, 1,3-dioxan-5-yl, 1,4-dioxan-2-yl, 1,3-dithian-2-yl, 1,3-dithian-4-yl, 1,3-dithian-5-yl, 1,4-dithian-2-yl, 1,3-oxathian-2-yl, 1,3-oxathian-4-yl, 1,3-oxathian-5-yl, 1,3-oxathian-6-yl, 1,4-oxathian-2-yl, 1,4-oxathian-3-yl, 1,2-dithian-3-yl, 1,2-dithian-4-yl, hexahydropyrimidin-2-yl, hexahydropyrimidin-4-yl, hexahydropyrimidin-5-yl, hexahydropyrazin-2-yl, hexahydropyridazin-3-yl, hexahydropyridazin-4-yl, tetrahydro-1,3-oxazin-2-yl, tetrahydro-1,3-oxazin-4-yl, tetrahydro-1,3-oxazin-5-yl, tetrahydro-1,3-oxazin-6-yl, tetrahydro-1,3-thiazin-2-yl, tetrahydro-1,3-thiazin-4-yl, tetrahydro-1,3-thiazin-5-yl, tetrahydro-1,3-thiazin-6-yl, tetrahydro-1,4-thiazin-2-yl, tetrahydro-1,4-thiazin-3-yl, tetrahydro-1,4-oxazin-2-yl, tetrahydro-1,4-oxazin-3-yl, tetrahydro-1,2-oxazin-3-yl, tetrahydro-1,2-oxazin-4-yl, tetrahydro-1,2-oxazin-5-yl, tetrahydro-1,2-oxazin-6-yl;

6-membered saturated rings which are attached via nitrogen, such as: piperidin-1-yl, hexahydropyrimidin-1-yl, hexahydropyrazin-1-yl, hexahydro-pyridazin-1-yl, tetrahydro-1,3-oxazin-3-yl, tetrahydro-1,3-thiazin-3-yl, tetrahydro-1,4-thiazin-4-yl, tetrahydro-1,4-oxazin-4-yl, tetrahydro-1,2-oxazin-2-yl;

6-membered partially unsaturated rings which are attached via carbon, such as: 2H-3,4-dihydropyran-6-yl, 2H-3,4-dihydropyran-5-yl, 2H-3,4-dihydropyran-4-yl, 2H-3,4-dihydropyran-3-yl, 2H-3,4-dihydropyran-2-yl, 2H-3,4-dihydro-pyran-6-yl, 2H-3,4-dihydrothiopyran-5-yl, 2H-3,4-dihydrothiopyran-4-yl, 2H-3,4-dihydropyran-3-yl, 2H-3,4-dihydropyran-2-yl, 1,2,3,4-tetrahydropyridin-6-yl, 1,2,3,4-tetrahydropyridin-5-yl, 1,2,3,4-tetrahydropyridin-4-yl, 1,2,3,4-tetrahydropyridin-3-yl, 1,2,3,4-tetrahydropyridin-2-yl, 2H-5,6-dihydropyran-2-yl, 2H-5,6-dihydropyran-3-yl, 2H-5,6-dihydropyran-4-yl, 2H-5,6-dihydropyran-5-yl, 2H-5,6-dihydropyran- 6-yl, 2H-5,6-dihydrothiopyran-2-yl, 2H-5,6-dihydrothiopyran-3-yl, 2H-5,6-dihydrothiopyran-4-yl, 2H-5,6-dihydrothiopyran-5-yl, 2H-5,6-dihydrothiopyran-6-yl, 1,2,5,6-tetrahydropyridin-2-yl, 1,2,5,6-tetrahydropyridin-3-yl, 1,2,5,6-tetrahydropyridin-4-yl, 1,2,5,6-tetrahydropyridin-5-yl, 1,2,5,6-tetrahydropyridin-6-yl, 2,3,4,5-tetrahydropyridin-2-yl, 2,3,4,5-tetrahydropyridin-3-yl, 2,3,4,5-tetrahydropyridin-4-yl, 2,3,4,5-tetrahydropyridin-5-yl, 2,3,4,5-tetrahydropyridin-6-yl, 4H-pyran-2-yl, 4H-pyran-3-yl, 4H-pyran-4-yl, 4H-thiopyran-2-yl, 4H-thiopyran-3-yl, 4H-thiopyran-4-yl, 1,4-dihydropyridin-2-yl, 1,4-dihydropyridin-3-yl, 1,4-dihydropyridin-4-yl, 2H-pyran-2-yl, 2H-pyran-3-yl, 2H-pyran-4-yl, 2H-pyran-5-yl, 2H-pyran-6-yl, 2H-thiopyran-2-yl, 2H-thiopyran-3-yl, 2H-thiopyran-4-yl, 2H-thiopyran-5-yl, 2H-thiopyran-6-yl, 1,2-dihydropyridin-2-yl, 1,2-dihydropyridin-3-yl, 1,2-dihydropyridin-4-yl, 1,2-dihydropyridin-5-yl, 1,2-dihydropyridin-6-yl, 3,4-dihydropyridin-2-yl, 3,4-dihydropyridin-3-yl, 3,4-dihydropyridin-4-yl, 3,4-dihydropyridin-5-yl, 3,4-dihydropyridin-4-yl, 2,5-dihydropyridin-2-yl, 2,5-dihydropyridin-3-yl, 2,5-dihydropyridin-4-yl, 2,5-dihydropyridin-5-yl, 2,5-dihydropyridin-6-yl, 2,3-dihydropyridin-2-yl, 2,3-dihydropyridin-3-yl, 2,3-dihydropyridin-4-yl, 2,3-dihydropyridin-5-yl, 2,3-dihydropyridin-6-yl, 2H-5,6-dihydro-1,2-oxazin-3-yl, 2H-5,6-dihydro-1,2-oxazin-4-yl, 2H-5,6-dihydro-1,2-oxazin-5-yl, 2H-5,6-dihydro-1,2-oxazin-6-yl, 2H-5,6-dihydro-1,2-thiazin-3-yl, 2H-5,6-dihydro-1,2-thiazin-4-yl, 2H-5,6-dihydro-1,2-thiazin-5-yl, 2H-5,6-dihydro-1,2-thiazin-6-yl, 4H-5,6-dihydro-1,2-oxazin-3-yl, 4H-5,6-dihydro-1,2-oxazin-4-yl, 4H-5,6-dihydro-1,2-oxazin-5-yl, 4H-5,6-dihydro-1,2-oxazin-6-yl, 4H-5,6-dihydro-1,2-thiazin-3-yl, 4H-5,6-dihydro-1,2-thiazin-4-yl, 4H-5,6-dihydro-1,2-thiazin-5-yl, 4H-5,6-dihydro-1,2-thiazin-6-yl, 2H-3,6-dihydro-1,2-oxazin-3-yl, 2H-3,6-dihydro-1,2-oxazin-4-yl, 2H-3,6-dihydro-1,2-oxazin-5-yl, 2H-3,6-dihydro-1,2-oxazin-6-yl, 2H-3,6-dihydro-1,2-thiazin-3-yl, 2H-3,6-dihydro-1,2-thiazin-4-yl, 2H-3,6-dihydro-1,2-thiazin-5-yl, 2H-3,6-dihydro-1,2-thiazin-6-yl, 2H-3,4-dihydro-1,2-oxazin-3-yl, 2H-3,4-dihydro-1,2-oxazin-4-yl, 2H-3,4-dihydro-1,2-oxazin-5-yl, 2H-3,4-dihydro-1,2-oxazin-6-yl, 2H-3,4-dihydro-1,2-thiazin-3-yl, 2H-3,4-dihydro-1,2-thiazin-4-yl, 2H-3,4-dihydro-1,2-thiazin-5-yl, 2H-3,4-dihydro-1,2-thiazin-6-yl, 2,3,4,5-tetrahydropyridazin-3-yl, 2,3,4,5-tetrahydropyridazin-4-yl, 2,3,4,5-tetrahydropyridazin-5-yl, 2,3,4,5-tetrahydropyridazin-6-yl, 3,4,5,6-tetrahydropyridazin-3-yl, 3,4,5,6-tetrahydropyridazin-4-yl, 1,2,5,6-tetrahydropyridazin-3-yl, 1,2,5,6-tetrahydropyridazin-4-yl, 1,2,5,6-tetrahydropyridazin-5-yl, 1,2,5,6-tetrahydropyridazin-6-yl, 1,2,3,6-tetrahydropyridazin-3-yl, 1,2,3,6-tetrahydropyridazin-4-yl, 4H-5,6-dihydro-1,3-oxazin-2-yl, 4H-5,6-dihydro-1,3-oxazin-4-yl, 4H-5,6-dihydro-1,3-oxazin-5-yl, 4H-5,6-dihydro-1,3-oxazin-6-yl, 4H-5,6-dihydro-1,3-thiazin-2-yl, 4H-5,6-dihydro-1,3-thiazin-4-yl, 4H-5,6-dihydro-1,3-thiazin-5-yl, 4H-5,6-dihydro-1,3-thiazin-6-yl, 3,4,5,6-tetrahydropyrimidin-2-yl, 3,4,5,6-tetrahydropyrimidin-4-yl, 3,4,5,6-tetrahydropyrimidin-5-yl, 3,4,5,6-tetrahydropyrimidin-6-yl, 1,2,3,4-tetrahydropyrazin-2-yl, 1,2,3,4-tetrahydropyrazin-5-yl, 1,2,3,4-tetrahydro-pyrimidin-2-yl, 1,2,3,4-tetrahydropyrimidin-4-yl, 1,2,3,4-tetrahydropyrimidin-5-yl, 1,2,3,4-tetrahydropyrimidin-6-yl, 2,3-dihydro-1,4-thiazin-2-yl, 2,3-dihydro-1,4-thiazin-3-yl, 2,3-dihydro-1,4-thiazin-5-yl, 2,3-dihydro-1,4-thiazin-6-yl, 2H-1,2-oxazin-3-yl, 2H-1,2-oxazin-4-yl, 2H-1,2-oxazin-5-yl, 2H-1,2-oxazin-6-yl, 2H-1,2-thiazin-3-yl, 2H-1,2-thiazin-4-yl, 2H-1,2-thiazin-5-yl, 2H-1,2-thiazin-6-yl, 4H-1,2-oxazin-3-yl, 4H-1,2-oxazin-4-yl, 4H-1,2-oxazin-5-yl, 4H-1,2-oxazin-6-yl, 4H-1,2-thiazin-3-yl, 4H-1,2-thiazin-4-yl, 4H-1,2-thiazin-5-yl, 4H-1,2-thiazin-6-yl, 6H-1,2-oxazin-3-yl, 6H-1,2-oxazin-4-yl, 6H-1,2-oxazin-5-yl, 6H-1,2-oxazin-6-yl, 6H-1,2-thiazin-3-yl, 6H-1,2-thiazin-4-yl, 6H-1,2-thiazin-5-yl, 6H-1,2-thiazin-6-yl, 2H-1,3-oxazin-2-yl, 2H-1,3-oxazin-4-yl, 2H-1,3-oxazin-5-yl, 2H-1,3-oxazin-6-yl, 2H-1,3-thiazin-2-yl, 2H-1,3-thiazin-4-yl, 2H-1,3-thiazin-5-yl, 2H-1,3-thiazin-6-yl, 4H-1,3-oxazin-2-yl, 4H-1,3-oxazin-4-yl, 4H-1,3-oxazin-5-yl, 4H-1,3-oxazin-6-yl, 4H-1,3-thiazin-2-yl, 4H-1,3-thiazin-4-yl, 4H-1,3-thiazin-5-yl, 4H-1,3-thiazin-6-yl, 6H-1,3-oxazin-2-yl, 6H-1,3-oxazin-4-yl, 6H-1,3-oxazin-5-yl, 6H-1,3-oxazin-6-yl, 6H-1,3-thiazin-2-yl, 6H-1,3-oxazin-4-yl, 6H-1,3-oxazin-5-yl, 6H-1,3-thiazin-6-yl, 2H-1,4-oxazin-2-yl, 2H-1,4-oxazin-3-yl, 2H-1,4-oxazin-5-yl, 2H-1,4-oxazin-6-yl, 2H-1,4-thiazin-2-yl, 2H-1,4-thiazin-3-yl, 2H-1,4-thiazin-5-yl, 2H-1,4-thiazin-6-yl, 4H-1,4-oxazin-2-yl, 4H-1,4-oxazin-3-yl, 4H-1,4-thiazin-2-yl, 4H-1,4-thiazin-3-yl, 1,4-dihydropyridazin-3-yl, 1,4-dihydropyridazin-4-yl, 1,4-dihydropyridazin-5-yl, 1,4-dihydropyridazin-6-yl, 1,4-dihydropyrazin-2-yl, 1,2-dihydropyrazin-2-yl, 1,2-dihydropyrazin-3-yl, 1,2-dihydropyrazin-5-yl, 1,2-dihydropyrazin-6-yl, 1,4-dihydropyrimidin-2-yl, 1,4-dihydropyrimidin-4-yl, 1,4-dihydropyrimidin-5-yl, 1,4-dihydropyrimidin-6-yl, 3,4-dihydropyrimidin-2-yl, 3,4-dihydropyrimidin-4-yl, 3,4-dihydropyrimidin-5-yl or 3,4-dihydropyrimidin-6-yl;

6-membered partially unsaturated rings which are attached via nitrogen, such as: 1,2,3,4-tetrahydropyridin-1-yl, 1,2,5,6-tetrahydropyridin-1-yl, 1,4-dihydro-pyridin-1-yl, 1,2-dihydropyridin-1-yl, 2H-5,6-dihydro-1,2-oxazin-2-yl, 2H-5,6-dihydro-1,2-thiazin-2-yl, 2H-3,6-dihydro-1,2-oxazin-2-yl, 2H-3,6-dihydro-1,2-thiazin-2-yl, 2H-3,4-dihydro-1,2-oxazin-2-yl, 2H-3,4-dihydro-1,2-thiazin-2-yl, 2,3,4,5-tetrahydropyridazin-2-yl, 1,2,5,6-tetrahydropyridazin-1-yl, 1,2,5,6-tetrahydropyridazin-2-yl, 1,2,3,6-tetrahydropyridazin-1-yl, 3,4,5,6-tetrahydropyridazin-3-yl, 1,2,3,4-tetrahydropyrazin-1-yl, 1,2,3,4-tetrahydropyrimidin-1-yl, 1,2,3,4-tetrahydropyrimidin-3-yl, 2,3-dihydro-1,4-thiazin-4-yl, 2H-1,2-oxazin-2-yl, 2H-1,2-thiazin-2-yl, 4H-1,4-oxazin-4-yl, 4H-1,4-thiazin-4-yl, 1,4-dihydro-pyridazin-1-yl, 1,4-dihydropyrazin-1-yl, 1,2-dihydro-pyrazin-1-yl, 1,4-dihydropyrimidin-1-yl or 3,4-dihydropyrimidin-3-yl;

6-membered aromatic rings which are attached via carbon, such as: pyridin-2-yl, pyridin-3-yl, pyridin-4-yl, pyridazin-3-yl, pyridazin-4-yl, pyrimidin-2-yl, pyrimidin-4-yl, pyrimidin-5-yl, pyrazin-2-yl, 1,3,5-triazin-2-yl, 1,2,4-triazin-3-yl, 1,2,4-triazin-5-yl, 1,2,4-triazin-6-yl, 1,2,4,5-tetrazin-3-yl;

it being possible for a bicyclic ring system to be formed with a fused-on phenyl ring or with a $C_3$-$C_6$-carbocycle or a further 5- or 6-membered heterocycle.

All phenyl rings and heterocyclyl rings and all phenyl components in phenyl-$C_1$-$C_6$-alkyl, phenylcarbonyl, phenylcarbonyl-$C_1$-$C_6$-alkyl, phenoxycarbonyl, phenylaminocarbonyl, phenylsulfonylaminocarbonyl, N—($C_1$-$C_6$-alkyl)-N-phenylaminocarbonyl and phenyl-$C_1$-$C_6$-alkylcarbonyl, and all heterocyclyl components in heterocyclyl-$C_1$-$C_6$-alkyl, heterocyclylcarbonyl, heterocyclylcarbonyl-$C_1$-$C_6$-alkyl, heterocyclyloxycarbonyl, heterocyclylaminocarbonyl, heterocyclylsulfonylaminocarbonyl, N—($C_1$-$C_6$-alkyl)-N-heterocyclylaminocarbonyl and heterocyclyl-$C_1$-$C_6$-alkylcarbonyl are, unless indicated otherwise, preferably unsubstituted or carry one to three halogen atoms and/or one nitro group, one cyano radical and/or one or two methyl, trifluoromethyl, methoxy or trifluoromethoxy substituents.

In a particular embodiment, the variables of the compounds of the formula I have the following meanings which, both on their own and in combination with one another, are particular embodiments of the compounds of the formula I:

Preference is given to the benzoyl-substituted phenylalanineamides of the formula I in which
$R^1$ is halogen, $C_1$-$C_4$-alkyl or $C_1$-$C_6$-haloalkyl;
  particularly preferably halogen or $C_1$-$C_6$-haloalkyl;
  especially preferably halogen or $C_1$-$C_4$-haloalkyl;
  most preferably fluorine, chlorine or $CF_3$.

Preference is also given to the benzoyl-substituted phenylalanineamides of the formula I in which
$R^2$ is hydrogen, halogen, $NO_2$, $C_1$-$C_4$-alkyl or $C_1$-$C_6$-haloalkyl;
  very preferably hydrogen, halogen, $NO_2$ or $C_1$-$C_6$-haloalkyl;
  particularly preferably hydrogen, halogen, $NO_2$ or $C_1$-$C_4$-haloalkyl;
  especially preferably hydrogen, fluorine, chlorine, $NO_2$ or $CF_3$;
  most preferably hydrogen, fluorine, chlorine or $NO_2$;
  with utmost preference hydrogen, fluorine or $NO_2$.

Preference is also given to the benzoyl-substituted phenylalanineamides of the formula I in which
$R^2$ and $R^3$ independently of one another are
  hydrogen, halogen, $C_1$-$C_4$-alkyl or $C_1$-$C_6$-haloalkyl;
  very preferably hydrogen, halogen or $C_1$-$C_6$-haloalkyl;
  particularly preferably hydrogen, halogen or $C_1$-$C_4$-haloalkyl;
  especially preferably hydrogen, fluorine, chlorine or $CF_3$;
  most preferably hydrogen, fluorine or chlorine;
  with utmost preference hydrogen or fluorine.

Preference is also given to the benzoyl-substituted phenylalanineamides of the formula I in which
$R^4$ is hydrogen, halogen, $C_1$-$C_4$-alkyl or $C_1$-$C_4$-haloalkyl;
  particularly preferably hydrogen, halogen or $C_1$-$C_4$-alkyl;
  especially preferably hydrogen or halogen;
  most preferably hydrogen.

Preference is also given to the benzoyl-substituted phenylalanineamides of the formula I in which
$R^5$ is hydrogen, halogen, $C_1$-$C_4$-alkyl or $C_1$-$C_4$-haloalkyl;
  particularly preferably hydrogen, halogen or $C_1$-$C_4$-alkyl;
  especially preferably hydrogen or halogen;
  most preferably hydrogen.

Preference is also given to the benzoyl-substituted phenylalanineamides of the formula I in which
$R^6$ is hydrogen; and
$R^7$ is hydrogen or hydroxyl;
  particularly preferably hydrogen.

Preference is also given to the benzoyl-substituted phenylalanineamides of the formula I in which
$R^8$ is $C_1$-$C_6$-alkyl or $C_1$-$C_6$-haloalkyl;
  particularly preferably $C_1$-$C_6$-alkyl;
  especially preferably $C_1$-$C_4$-alkyl;
  most preferably $CH_3$.

Preference is also given to the benzoyl-substituted phenylalanineamides of the formula I in which
$R^9$ is $OR^{16}$ or $SR^{17}$;
  particularly preferably $OR^{16}$.

Preference is also given to the benzoyl-substituted phenylalanineamides of the formula I in which
$R^9$ is $OR^{16}$ or $NR^{18}R^{19}$;
  particularly preferably $NR^{18}R^{19}$.

Preference is also given to the benzoyl-substituted phenylalanineamides of the formula I in which
$R^9$ is $SR^{16}$ or $NR^{18}R^{19}$;
  particularly preferably $SR^{16}$.

Preference is also given to the benzoyl-substituted phenylalanineamides of the formula I in which
$R^{10}$ is hydrogen or $C_1$-$C_4$-alkyl;
  preferably hydrogen or $CH_3$;
  especially preferably hydrogen.

Preference is also given to the benzoyl-substituted phenylalanineamides of the formula I in which
$R^{11}$ is hydrogen, halogen, $C_1$-$C_6$-alkyl, hydroxyl, $C_1$-$C_6$-alkoxy, hydroxy-$C_1$-$C_4$-alkyl, $C_1$-$C_6$-alkoxy-$C_1$-$C_4$-alkyl, tri($C_1$-$C_6$-alkyl)silyloxy-$C_1$-$C_4$-alkyl, (hydroxycarbonyl)-$C_1$-$C_4$-alkoxy, ($C_1$-$C_4$-alkoxycarbonyl)-$C_1$-$C_4$-alkoxy, (di($C_1$-$C_4$-alkyl)aminocarbonyl]oxy-$C_1$-$C_4$-alkyl, $C_1$-$C_4$-alkylsulfonylamino, $C_1$-$C_4$-haloalkylsulfonylamino, ($C_1$-$C_4$-alkylcarbonyl)amino or phenyl, where the phenyl radical may carry one to three radicals from the following group: halogen, nitro, $C_1$-$C_4$-alkyl, $C_1$-$C_4$-haloalkyl, hydroxycarbonyl and $C_1$-$C_6$-alkoxycarbonyl;
  particularly preferably hydrogen, halogen, $C_1$-$C_6$-alkyl, hydroxy-$C_1$-$C_4$-alkyl, (hydroxycarbonyl)-$C_1$-$C_4$-alkoxy, ($C_1$-$C_4$-alkoxycarbonyl)-$C_1$-$C_4$-alkoxy or ($C_1$-$C_4$-alkylcarbonyl)amino;
  especially preferably hydrogen, halogen, $C_1$-$C_4$-alkyl, hydroxy-$C_1$-$C_4$-alkyl, (hydroxycarbonyl)-$C_1$-$C_4$-alkoxy, ($C_1$-$C_4$-alkoxycarbonyl)-$C_1$-$C_4$-alkoxy or ($C_1$-$C_4$-alkylcarbonyl)amino;
  very preferably hydrogen, fluorine, chlorine, bromine, $CH_3$, hydroxy-$C_1$-$C_4$-alkyl, (hydroxycarbonyl)-$C_1$-$C_4$-alkoxy, ($C_1$-$C_4$-alkoxycarbonyl)-$C_1$-$C_4$-alkoxy or ($C_1$-$C_6$-alkylcarbonyl)amino;
  most preferably hydrogen, fluorine, $CH_3$, hydroxy-$C_1$-$C_4$-alkyl, (hydroxycarbonyl)-$C_1$-$C_4$-alkoxy, ($C_1$-$C_4$-alkoxycarbonyl)-$C_1$-$C_4$-alkoxy or ($C_1$-$C_6$-alkylcarbonyl)amino.

Preference is also given to the benzoyl-substituted phenylalanineamides of the formula I in which
$R^{11}$ is hydrogen, halogen, $C_1$-$C_6$-alkyl, hydroxyl or $C_1$-$C_6$-alkoxy;
  particularly preferably hydrogen, halogen or $C_1$-$C_6$-alkyl;
  especially preferably hydrogen, halogen or $C_1$-$C_4$-alkyl;
  very preferably hydrogen, fluorine, chlorine, bromine or $CH_3$;
  most preferably hydrogen, fluorine or $CH_3$.

Preference is also given to the benzoyl-substituted phenylalanineamides of the formula I in which
$R^{12}$ is hydrogen, halogen, $C_1$-$C_6$-alkyl, $C_1$-$C_6$-haloalkyl or ($C_1$-$C_4$-alkylcarbonyl)-amino;
  particularly preferably hydrogen, halogen, $C_1$-$C_6$-alkyl or ($C_1$-$C_4$-alkylcarbonyl)-amino;
  especially preferably hydrogen, halogen, $C_1$-$C_4$-alkyl or ($C_1$-$C_4$-alkylcarbonyl)-amino.

Preference is also given to the benzoyl-substituted phenylalanineamides of the formula I in which
$R^{12}$ is hydrogen, halogen, $C_1$-$C_6$-alkyl or $C_1$-$C_6$-haloalkyl;
  particularly preferably hydrogen, halogen or $C_1$-$C_6$-alkyl;

especially preferably hydrogen, halogen or $C_1$-$C_4$-alkyl; most preferably hydrogen or halogen;
with utmost preference hydrogen, fluorine or chlorine.

Preference is also given to the benzoyl-substituted phenylalanineamides of the formula I in which
$R^{13}$, $R^{14}$ and $R^{15}$ in each case independently of one another are
hydrogen, halogen, cyano, $C_1$-$C_4$-alkyl or $C_1$-$C_4$-haloalkyl;
particularly preferably hydrogen, halogen or cyano;
especially preferably hydrogen, fluorine or chlorine;
most preferably hydrogen.

Preference is also given to the benzoyl-substituted phenylalanineamides of the formula I in which
$R^{16}$, $R^{17}$ and $R^{18}$ in each case independently of one another are
hydrogen, $C_1$-$C_6$-alkyl, $C_3$-$C_6$-alkenyl, $C_3$-$C_6$-alkynyl, $C_1$-$C_6$-alkylcarbonyl, $C_2$-$C_6$-alkenylcarbonyl, $C_3$-$C_6$-cycloalkylcarbonyl, $C_1$-$C_6$-alkoxycarbonyl, $C_1$-$C_6$-alkylaminocarbonyl, $C_1$-$C_6$-alkylsulfonylaminocarbonyl, di($C_1$-$C_6$-alkyl)aminocarbonyl, N—($C_1$-$C_6$-alkoxy)-N—($C_1$-$C_6$-alkyl)aminocarbonyl, di($C_1$-$C_6$-alkyl)aminothiocarbonyl, $C_1$-$C_6$-alkoxyimino-$C_1$-$C_6$-alkyl,
where the alkyl, cycloalkyl and alkoxy radicals mentioned may be partially or fully halogenated and/or may carry one to three of the following groups: cyano, hydroxyl, $C_3$-$C_6$-cycloalkyl, $C_1$-$C_4$-alkoxy, $C_1$-$C_4$-alkylthio, di($C_1$-$C_4$-alkyl)amino, $C_1$-$C_4$-alkylcarbonyl, hydroxycarbonyl, $C_1$-$C_4$-alkoxycarbonyl, aminocarbonyl, $C_1$-$C_4$-alkylaminocarbonyl, di($C_1$-$C_4$-alkyl)aminocarbonyl, or $C_1$-$C_4$-alkylcarbonyloxy;
phenyl, phenyl-$C_1$-$C_6$-alkyl, phenylcarbonyl, phenylcarbonyl-$C_1$-$C_6$-alkyl, phenylsulfonylaminocarbonyl or phenyl-$C_1$-$C_6$-alkylcarbonyl,
where the phenyl radical of the 6 last-mentioned substituents may be partially or fully halogenated and/or may carry one to three of the following groups: nitro, cyano, $C_1$-$C_4$-alkyl, $C_1$-$C_4$-haloalkyl, $C_1$-$C_4$-alkoxy or $C_1$-$C_4$-haloalkoxy; or
$SO_2R^{20}$;
particularly preferably hydrogen, $C_1$-$C_6$-alkyl, $C_3$-$C_6$-alkenyl, $C_3$-$C_6$-alkynyl, $C_1$-$C_6$-alkylcarbonyl, $C_2$-$C_6$-alkenylcarbonyl, $C_1$-$C_6$-alkoxycarbonyl, $C_1$-$C_6$-alkylsulfonylaminocarbonyl, di($C_1$-$C_6$-alkyl)aminocarbonyl, N—($C_1$-$C_6$-alkoxy)-N—($C_1$-$C_6$-alkyl)aminocarbonyl or di($C_1$-$C_6$-alkyl)aminothiocarbonyl,
where the alkyl or alkoxy radicals mentioned may be partially or fully halogenated and/or may carry one to three of the following groups: cyano, $C_1$-$C_4$-alkoxy, $C_1$-$C_4$-alkoxycarbonyl, $C_1$-$C_4$-alkylaminocarbonyl, di($C_1$-$C_4$-alkyl)aminocarbonyl or $C_1$-$C_4$-alkylcarbonyloxy;
phenyl-$C_1$-$C_6$-alkyl, phenylcarbonyl, phenylcarbonyl-$C_1$-$C_6$-alkyl, phenylsulfonylaminocarbonyl or phenyl-$C_1$-$C_6$-alkylcarbonyl,
where the phenyl ring of the 5 last-mentioned substituents may be partially or fully halogenated and/or may carry one to three of the following groups: nitro, cyano, $C_1$-$C_4$-alkyl, $C_1$-$C_4$-haloalkyl, $C_1$-$C_4$-alkoxy or $C_1$-$C_4$-haloalkoxy; or
$SO_2R^{20}$;
especially preferably hydrogen, $C_1$-$C_6$-alkyl, $C_3$-$C_6$-alkenyl, $C_3$-$C_6$-alkynyl, $C_1$-$C_6$-alkylcarbonyl, $C_2$-$C_6$-alkenylcarbonyl, $C_1$-$C_6$-alkoxycarbonyl, di($C_1$-$C_6$-alkyl)aminocarbonyl, N—($C_1$-$C_6$-alkoxy)-N—($C_1$-$C_6$-alkyl)aminocarbonyl, di($C_1$-$C_6$-alkyl)aminothiocarbonyl, phenyl-$C_1$-$C_6$-alkyl, phenylcarbonyl-$C_1$-$C_6$-alkyl or phenyl-$C_1$-$C_6$-alkylcarbonyl,
where the phenyl ring of the 4 last-mentioned substituents may be partially or fully halogenated and/or may carry one to three of the following groups: nitro, cyano, $C_1$-$C_4$-alkyl, $C_1$-$C_4$-haloalkyl, $C_1$-$C_4$-alkoxy or $C_1$-$C_4$-haloalkoxy; or
$SO_2R^{20}$.

Preference is also given to the benzoyl-substituted phenylalanineamides of the formula I in which
$R^{16}$, $R^{17}$ and $R^{18}$ in each case independently of one another are
hydrogen, $C_1$-$C_6$-alkyl, $C_3$-$C_6$-alkenyl, $C_3$-$C_6$-alkynyl, $C_1$-$C_6$-alkylcarbonyl, $C_2$-$C_6$-alkenylcarbonyl, $C_3$-$C_6$-cycloalkylcarbonyl, $C_1$-$C_6$-alkoxycarbonyl, $C_1$-$C_6$-alkylaminocarbonyl, di($C_1$-$C_6$-alkyl)aminocarbonyl, N—($C_1$-$C_6$-alkoxy)-N—($C_1$-$C_6$-alkyl)aminocarbonyl, di($C_1$-$C_6$-alkyl)aminothiocarbonyl, $C_1$-$C_6$-alkoxyimino-$C_1$-$C_6$-alkyl, where the alkyl, cycloalkyl or alkoxy radicals mentioned may be partially or fully halogenated and/or may carry one to three of the following groups:
cyano, hydroxyl, $C_3$-$C_6$-cycloalkyl, $C_1$-$C_4$-alkoxy, $C_1$-$C_4$-alkylthio, di($C_1$-$C_4$-alkyl)amino, $C_1$-$C_4$-alkylcarbonyl, hydroxycarbonyl, $C_1$-$C_4$-alkoxycarbonyl, aminocarbonyl, $C_1$-$C_4$-alkylaminocarbonyl, di($C_1$-$C_4$-alkyl)aminocarbonyl or $C_1$-$C_4$-alkylcarbonyloxy; or
$SO_2R^{20}$.

Preference is also given to the benzoyl-substituted phenylalanineamides of the formula I in which $R^{16}$ and $R^{18}$ in each case independently of one another are
hydrogen, $C_1$-$C_6$-alkyl, $C_3$-$C_6$-alkenyl, $C_3$-$C_6$-alkynyl, $C_1$-$C_6$-alkylcarbonyl, $C_1$-$C_6$-alkoxycarbonyl, $C_1$-$C_6$-alkylaminocarbonyl, di($C_1$-$C_6$-alkyl)aminocarbonyl, N—($C_1$-$C_6$-alkoxy)-N—($C_1$-$C_6$-alkyl)aminocarbonyl,
where the alkyl and alkoxy radicals mentioned may be partially or fully halogenated and/or may carry one to three of the following groups: cyano, $C_1$-$C_4$-alkoxy, $C_1$-$C_4$-alkylaminocarbonyl or di($C_1$-$C_4$-alkyl)aminocarbonyl;
phenyl-$C_1$-$C_6$-alkyl, phenylcarbonyl, phenylcarbonyl-$C_1$-$C_6$-alkyl, phenylaminocarbonyl, N—($C_1$-$C_6$-alkyl)-N-(phenyl)aminocarbonyl or heterocyclylcarbonyl,
where the phenyl and the heterocyclyl radical of the 6 last-mentioned substituents may be partially or fully halogenated and/or may carry one to three of the following groups: cyano, $C_1$-$C_4$-alkyl or $C_1$-$C_4$-haloalkyl; or
$SO_2R^{20}$;
particularly preferably hydrogen, $C_1$-$C_4$-alkyl, $C_3$-$C_4$-alkenyl, $C_3$-$C_4$-alkynyl, $C_1$-$C_4$-alkylcarbonyl, $C_1$-$C_4$-alkoxycarbonyl, $C_1$-$C_4$-alkylaminocarbonyl, di-($C_1$-$C_4$-alkyl)aminocarbonyl, N—($C_1$-$C_4$-alkoxy)-N—($C_1$-$C_4$-alkyl)aminocarbonyl,
where the alkyl and alkoxy radicals mentioned may be partially or fully halogenated and/or may carry one to three of the following groups: cyano, $C_1$-$C_4$-alkoxy, $C_1$-$C_4$-alkylaminocarbonyl or di($C_1$-$C_4$-alkyl)aminocarbonyl;
phenyl-$C_1$-$C_4$-alkyl, phenylcarbonyl, phenylcarbonyl-$C_1$-$C_4$-alkyl, phenylaminocarbonyl, N—($C_1$-$C_4$-alkyl)-N-(phenyl)aminocarbonyl or heterocyclylcarbonyl, where the phenyl and the heterocyclyl radical of the 6 last-mentioned substituents may be partially or fully halogenated and/or may carry one to three of the following groups: cyano, $C_1$-$C_4$-alkyl or $C_1$-$C_4$-haloalkyl; or $SO_2R^{20}$;

especially preferably hydrogen or $C_1$-$C_4$-alkyl,
where the alkyl radical mentioned may be partially or fully halogenated and/or may carry one to three of the following groups:
cyano, $C_1$-$C_4$-alkoxy, $C_1$-$C_4$-alkylaminocarbonyl or di($C_1$-$C_4$-alkyl)aminocarbonyl;
phenyl-$C_1$-$C_4$-alkyl, phenylcarbonyl, phenylcarbonyl-$C_1$-$C_4$-alkyl, phenylaminocarbonyl, N—($C_1$-$C_4$-alkyl)-N-(phenyl)aminocarbonyl or heterocyclylcarbonyl, or $SO_2R^{20}$;
most preferably hydrogen, $C_1$-$C_4$-alkylcarbonyl, $C_1$-$C_6$-alkylaminocarbonyl, di($C_1$-$C_4$-alkyl)aminocarbonyl, phenylaminocarbonyl, N($C_1$-$C_4$-alkyl)-N-(phenyl)-aminocarbonyl, $SO_2CH_3$, $SO_2CF_3$ or $SO_2(C_6H_5)$.

Preference is also given to the benzoyl-substituted phenylalanineamides of the formula I in which
$R^{17}$ is hydrogen, $C_1$-$C_6$-alkylcarbonyl, $C_1$-$C_6$-alkoxycarbonyl, $C_1$-$C_6$-alkylaminocarbonyl, di($C_1$-$C_6$-alkyl)aminocarbonyl or N—($C_1$-$C_6$-alkoxy)-N—($C_1$-$C_6$-alkyl)aminocarbonyl,
where the alkyl and alkoxy radicals mentioned may be partially or fully halogenated and/or may carry one to three of the following groups: cyano or $C_1$-$C_4$-alkoxy;
particularly preferably hydrogen, $C_1$-$C_4$-alkylcarbonyl, $C_1$-$C_4$-alkoxycarbonyl, $C_1$-$C_4$-alkylaminocarbonyl, di($C_1$-$C_4$-alkyl)aminocarbonyl or N—($C_1$-$C_4$-alkoxy)-N—($C_1$-$C_4$-alkyl)aminocarbonyl,
where the alkyl and alkoxy radicals mentioned may be partially or fully halogenated and/or may carry one to three of the following groups: cyano or $C_1$-$C_4$-alkoxy;
especially preferably hydrogen, $C_1$-$C_4$-alkylcarbonyl, $C_1$-$C_4$-alkoxycarbonyl, $C_1$-$C_4$-alkylaminocarbonyl, di($C_1$-$C_4$-alkyl)aminocarbonyl, N—($C_1$-$C_4$-alkoxy)-N—($C_1$-$C_4$-alkyl)aminocarbonyl.

Preference is likewise given to the benzoyl-substituted phenylalanineamides of the formula I in which
$R^{19}$ is hydrogen, $C_1$-$C_6$-alkyl, $C_3$-$C_6$-cycloalkyl, $C_3$-$C_6$-alkenyl or $C_3$-$C_6$-alkynyl,
where the 4 last-mentioned radicals may be partially or fully halogenated and/or may carry one to three of the following groups: cyano, hydroxyl, $C_3$-$C_6$-cycloalkyl, $C_1$-$C_4$-alkoxy, $C_1$-$C_4$-alkylthio, di($C_1$-$C_4$-alkyl)amino, $C_1$-$C_4$-alkylcarbonyl, hydroxycarbonyl, $C_1$-$C_4$-alkoxycarbonyl, aminocarbonyl, $C_1$-$C_4$-alkylaminocarbonyl, di($C_1$-$C_4$-alkyl)aminocarbonyl or $C_1$-$C_4$-alkylcarbonyloxy;
phenyl or phenyl-$C_1$-$C_6$-alkyl, where the phenyl ring of the 2 last-mentioned substituents may be partially or fully halogenated and/or may carry one to three of the following groups: nitro, cyano, $C_1$-$C_4$-alkyl, $C_1$-$C_4$-haloalkyl, $C_1$-$C_4$-alkoxy or $C_1$-$C_4$-haloalkoxy;
particularly preferably hydrogen, $C_1$-$C_6$-alkyl, $C_3$-$C_6$-alkenyl or $C_3$-$C_6$-alkynyl,
where the 3 radicals mentioned may be partially or fully halogenated and/or may carry one to three of the following groups: cyano, $C_1$-$C_4$-alkoxy, $C_1$-$C_4$-alkoxycarbonyl, $C_1$-$C_4$-alkylaminocarbonyl, di($C_1$-$C_4$-alkyl)aminocarbonyl or $C_1$-$C_4$-alkylcarbonyloxy;
phenyl or phenyl-$C_1$-$C_4$-alkyl, where the phenyl ring of the 2 last-mentioned substituents may be partially or fully halogenated and/or may carry one to three of the following groups: nitro, cyano, $C_1$-$C_4$-alkyl, $C_1$-$C_4$-haloalkyl, $C_1$-$C_4$-alkoxy or $C_1$-$C_4$-haloalkoxy;

especially preferably hydrogen or $C_1$-$C_6$-alkyl, where the alkyl radical may be partially or fully halogenated;
phenyl or phenyl-$C_1$-$C_4$-alkyl, where the phenyl ring of the 2 last-mentioned substituents may be partially or fully halogenated and/or may carry one to three of the following groups: cyano, $C_1$-$C_4$-alkyl or $C_1$-$C_4$-haloalkyl;
most preferably hydrogen or $C_1$-$C_4$-alkyl.

Preference is also given to the benzoyl-substituted phenylalanineamides of the formula I in which
$R^{20}$ is $C_1$-$C_6$-alkyl, $C_1$-$C_6$-haloalkyl or phenyl, where the phenyl radical may be partially or partly halogenated and/or may be substituted by $C_1$-$C_4$-alkyl; particularly preferably $C_1$-$C_4$-alkyl, $C_1$-$C_4$-haloalkyl or phenyl; especially preferably methyl, trifluoromethyl or phenyl.

Preference is also given to the benzoyl-substituted phenylalanineamides of the formula I in which
$R^1$ is fluorine, chlorine or $CF_3$,
$R^2$ and $R^3$ independently of one another are hydrogen, fluorine or chlorine,
$R^4$, $R^5$, $R^6$ and $R^7$ are hydrogen,
$R^8$ is $C_1$-$C_4$-alkyl,
particularly preferably $CH_3$;
$R^9$ is $OR^{16}$, $SR^{17}$ or $NR^{18}R^{19}$,
$R^{10}$ is hydrogen;
$R^{11}$ is hydrogen, halogen, cyano or $C_1$-$C_4$-alkyl, particularly preferably hydrogen, fluorine or $CH_3$;
$R^{12}$ is hydrogen, halogen or cyano, particularly preferably hydrogen, fluorine or chlorine;
$R^{13}$, $R^{14}$ and $R^{15}$ independently of one another are hydrogen, fluorine or chlorine, particularly preferably hydrogen;
$R^{16}$ and $R^{18}$ independently of one another are hydrogen, $C_1$-$C_4$-alkylcarbonyl, $C_1$-$C_4$-alkylaminocarbonyl, di($C_1$-$C_4$-alkyl)aminocarbonyl, phenylaminocarbonyl, N—($C_1$-$C_4$-alkyl)-N-(phenyl)aminocarbonyl, $SO_2CH_3$, $SO_2CF_3$ or $SO_2(C_6H_5)$;
$R^{17}$ is hydrogen, $C_1$-$C_4$-alkylcarbonyl, $C_1$-$C_4$-alkoxycarbonyl, $C_1$-$C_4$-alkylaminocarbonyl, di($C_1$-$C_4$-alkyl)aminocarbonyl, N—($C_1$-$C_4$-alkoxy)-N—($C_1$-$C_4$-alkyl) aminocarbonyl; and
$R^{19}$ is hydrogen or $C_1$-$C_4$-alkyl.

Most preference is given to compounds of the formula I.a.1 (corresponds to formula I where $R^1$=F; $R^2$, $R^3$, $R^4$, $R^5$, $R^6$, $R^7$, $R^{10}$, $R^{14}$, $R^{15}$=H; $R^8$=$CH_3$), in particular to the compounds of the formulae I.a.1.1 to I.a.1.558 of Table 1, where the definitions of the variables $R^1$ to $R^{20}$ are of particular importance for the compounds according to the invention not only in combination with one another but in each case also on their own.

TABLE 1

I.a.1

| No. | $R^9$ | $R^{11}$ | $R^{12}$ | $R^{13}$ |
|---|---|---|---|---|
| I.a.1.1 | OH | H | H | H |
| I.a.1.2 | OH | H | H | F |

TABLE 1-continued

I.a.1

| No. | R⁹ | R¹¹ | R¹² | R¹³ |
|---|---|---|---|---|
| I.a.1.3 | OH | H | F | H |
| I.a.1.4 | OH | H | F | F |
| I.a.1.5 | OH | H | Cl | H |
| I.a.1.6 | OH | H | Cl | F |
| I.a.1.7 | OH | F | H | H |
| I.a.1.8 | OH | F | H | F |
| I.a.1.9 | OH | F | F | H |
| I.a.1.10 | OH | F | F | F |
| I.a.1.11 | OH | F | Cl | H |
| I.a.1.12 | OH | F | Cl | F |
| I.a.1.13 | OH | CH₃ | H | H |
| I.a.1.14 | OH | CH₃ | H | F |
| I.a.1.15 | OH | CH₃ | F | H |
| I.a.1.16 | OH | CH₃ | F | F |
| I.a.1.17 | OH | CH₃ | Cl | H |
| I.a.1.18 | OH | CH₃ | Cl | F |
| I.a.1.19 | OC(O)CH₃ | H | H | H |
| I.a.1.20 | OC(O)CH₃ | H | H | F |
| I.a.1.21 | OC(O)CH₃ | H | F | H |
| I.a.1.22 | OC(O)CH₃ | H | F | F |
| I.a.1.23 | OC(O)CH₃ | H | Cl | H |
| I.a.1.24 | OC(O)CH₃ | H | Cl | F |
| I.a.1.25 | OC(O)CH₃ | F | H | H |
| I.a.1.26 | OC(O)CH₃ | F | H | F |
| I.a.1.27 | OC(O)CH₃ | F | F | H |
| I.a.1.28 | OC(O)CH₃ | F | F | F |
| I.a.1.29 | OC(O)CH₃ | F | Cl | H |
| I.a.1.30 | OC(O)CH₃ | F | Cl | F |
| I.a.1.31 | OC(O)CH₃ | CH₃ | H | H |
| I.a.1.32 | OC(O)CH₃ | CH₃ | H | F |
| I.a.1.33 | OC(O)CH₃ | CH₃ | F | H |
| I.a.1.34 | OC(O)CH₃ | CH₃ | F | F |
| I.a.1.35 | OC(O)CH₃ | CH₃ | Cl | H |
| I.a.1.36 | OC(O)CH₃ | CH₃ | Cl | F |
| I.a.1.37 | OC(O)tertC₄H₉ | H | H | H |
| I.a.1.38 | OC(O)tertC₄H₉ | H | H | F |
| I.a.1.39 | OC(O)tertC₄H₉ | H | F | H |
| I.a.1.40 | OC(O)tertC₄H₉ | H | F | F |
| I.a.1.41 | OC(O)tertC₄H₉ | H | Cl | H |
| I.a.1.42 | OC(O)tertC₄H₉ | H | Cl | F |
| I.a.1.43 | OC(O)tertC₄H₉ | F | H | H |
| I.a.1.44 | OC(O)tertC₄H₉ | F | H | F |
| I.a.1.45 | OC(O)tertC₄H₉ | F | F | H |
| I.a.1.46 | OC(O)tertC₄H₉ | F | F | F |
| I.a.1.47 | OC(O)tertC₄H₉ | F | Cl | H |
| I.a.1.48 | OC(O)tertC₄H₉ | F | Cl | F |
| I.a.1.49 | OC(O)tertC₄H₉ | CH₃ | H | H |
| I.a.1.50 | OC(O)tertC₄H₉ | CH₃ | H | F |
| I.a.1.51 | OC(O)tertC₄H₉ | CH₃ | F | H |
| I.a.1.52 | OC(O)tertC₄H₉ | CH₃ | F | F |
| I.a.1.53 | OC(O)tertC₄H₉ | CH₃ | Cl | H |
| I.a.1.54 | OC(O)tertC₄H₉ | CH₃ | Cl | F |
| I.a.1.55 | OC(O)NH(CH₃) | H | H | H |
| I.a.1.56 | OC(O)NH(CH₃) | H | H | F |
| I.a.1.57 | OC(O)NH(CH₃) | H | F | H |
| I.a.1.58 | OC(O)NH(CH₃) | H | F | F |
| I.a.1.59 | OC(O)NH(CH₃) | H | Cl | H |
| I.a.1.60 | OC(O)NH(CH₃) | H | Cl | F |
| I.a.1.61 | OC(O)NH(CH₃) | F | H | H |
| I.a.1.62 | OC(O)NH(CH₃) | F | H | F |
| I.a.1.63 | OC(O)NH(CH₃) | F | F | H |
| I.a.1.64 | OC(O)NH(CH₃) | F | F | F |
| I.a.1.65 | OC(O)NH(CH₃) | F | Cl | H |
| I.a.1.66 | OC(O)NH(CH₃) | F | Cl | F |
| I.a.1.67 | OC(O)NH(CH₃) | CH₃ | H | H |
| I.a.1.68 | OC(O)NH(CH₃) | CH₃ | H | F |
| I.a.1.69 | OC(O)NH(CH₃) | CH₃ | F | H |
| I.a.1.70 | OC(O)NH(CH₃) | CH₃ | F | F |
| I.a.1.71 | OC(O)NH(CH₃) | CH₃ | Cl | H |
| I.a.1.72 | OC(O)NH(CH₃) | CH₃ | Cl | F |
| I.a.1.73 | OC(O)NH(C₆H₅) | H | H | H |
| I.a.1.74 | OC(O)NH(C₆H₅) | H | H | F |
| I.a.1.75 | OC(O)NH(C₆H₅) | H | F | H |
| I.a.1.76 | OC(O)NH(C₆H₅) | H | F | F |
| I.a.1.77 | OC(O)NH(C₆H₅) | H | Cl | H |
| I.a.1.78 | OC(O)NH(C₆H₅) | H | Cl | F |
| I.a.1.79 | OC(O)NH(C₆H₅) | F | H | H |
| I.a.1.80 | OC(O)NH(C₆H₅) | F | H | F |
| I.a.1.81 | OC(O)NH(C₆H₅) | F | F | H |
| I.a.1.82 | OC(O)NH(C₆H₅) | F | F | F |
| I.a.1.83 | OC(O)NH(C₆H₅) | F | Cl | H |
| I.a.1.84 | OC(O)NH(C₆H₅) | F | Cl | F |
| I.a.1.85 | OC(O)NH(C₆H₅) | CH₃ | H | H |
| I.a.1.86 | OC(O)NH(C₆H₅) | CH₃ | H | F |
| I.a.1.87 | OC(O)NH(C₆H₅) | CH₃ | F | H |
| I.a.1.88 | OC(O)NH(C₆H₅) | CH₃ | F | F |
| I.a.1.89 | OC(O)NH(C₆H₅) | CH₃ | Cl | H |
| I.a.1.90 | OC(O)NH(C₆H₅) | CH₃ | Cl | F |
| I.a.1.91 | OC(O)N(CH₃)₂ | H | H | H |
| I.a.1.92 | OC(O)N(CH₃)₂ | H | H | F |
| I.a.1.93 | OC(O)N(CH₃)₂ | H | F | H |
| I.a.1.94 | OC(O)N(CH₃)₂ | H | F | F |
| I.a.1.95 | OC(O)N(CH₃)₂ | H | Cl | H |
| I.a.1.96 | OC(O)N(CH₃)₂ | H | Cl | F |
| I.a.1.97 | OC(O)N(CH₃)₂ | F | H | H |
| I.a.1.98 | OC(O)N(CH₃)₂ | F | H | F |
| I.a.1.99 | OC(O)N(CH₃)₂ | F | F | H |
| I.a.1.100 | OC(O)N(CH₃)₂ | F | F | F |
| I.a.1.101 | OC(O)N(CH₃)₂ | F | Cl | H |
| I.a.1.102 | OC(O)N(CH₃)₂ | F | Cl | F |
| I.a.1.103 | OC(O)N(CH₃)₂ | CH₃ | H | H |
| I.a.1.104 | OC(O)N(CH₃)₂ | CH₃ | H | F |
| I.a.1.105 | OC(O)N(CH₃)₂ | CH₃ | F | H |
| I.a.1.106 | OC(O)N(CH₃)₂ | CH₃ | F | F |
| I.a.1.107 | OC(O)N(CH₃)₂ | CH₃ | Cl | H |
| I.a.1.108 | OC(O)N(CH₃)₂ | CH₃ | Cl | F |
| I.a.1.109 | OC(O)N(CH₃)(C₆H₅) | H | H | H |
| I.a.1.110 | OC(O)N(CH₃)(C₆H₅) | H | H | F |
| I.a.1.111 | OC(O)N(CH₃)(C₆H₅) | H | F | H |
| I.a.1.112 | OC(O)N(CH₃)(C₆H₅) | H | F | F |
| I.a.1.113 | OC(O)N(CH₃)(C₆H₅) | H | Cl | H |
| I.a.1.114 | OC(O)N(CH₃)(C₆H₅) | H | Cl | F |
| I.a.1.115 | OC(O)N(CH₃)(C₆H₅) | F | H | H |
| I.a.1.116 | OC(O)N(CH₃)(C₆H₅) | F | H | F |
| I.a.1.117 | OC(O)N(CH₃)(C₆H₅) | F | F | H |
| I.a.1.118 | OC(O)N(CH₃)(C₆H₅) | F | F | F |
| I.a.1.119 | OC(O)N(CH₃)(C₆H₅) | F | Cl | H |
| I.a.1.120 | OC(O)N(CH₃)(C₆H₅) | F | Cl | F |
| I.a.1.121 | OC(O)N(CH₃)(C₆H₅) | CH₃ | H | H |
| I.a.1.122 | OC(O)N(CH₃)(C₆H₅) | CH₃ | H | F |
| I.a.1.123 | OC(O)N(CH₃)(C₆H₅) | CH₃ | F | H |
| I.a.1.124 | OC(O)N(CH₃)(C₆H₅) | CH₃ | F | F |

TABLE 1-continued

I.a.1

| No. | R⁹ | R¹¹ | R¹² | R¹³ |
|---|---|---|---|---|
| I.a.1.125 | OC(O)N(CH$_3$)(C$_6$H$_5$) | CH$_3$ | Cl | H |
| I.a.1.126 | OC(O)N(CH$_3$)(C$_6$H$_5$) | CH$_3$ | Cl | F |
| I.a.1.127 | OSO$_2$CH$_3$ | H | H | H |
| I.a.1.128 | OSO$_2$CH$_3$ | H | H | F |
| I.a.1.129 | OSO$_2$CH$_3$ | H | F | H |
| I.a.1.130 | OSO$_2$CH$_3$ | H | F | F |
| I.a.1.131 | OSO$_2$CH$_3$ | H | Cl | H |
| I.a.1.132 | OSO$_2$CH$_3$ | H | Cl | F |
| I.a.1.133 | OSO$_2$CH$_3$ | F | H | H |
| I.a.1.134 | OSO$_2$CH$_3$ | F | H | F |
| I.a.1.135 | OSO$_2$CH$_3$ | F | F | H |
| I.a.1.136 | OSO$_2$CH$_3$ | F | F | F |
| I.a.1.137 | OSO$_2$CH$_3$ | F | Cl | H |
| I.a.1.138 | OSO$_2$CH$_3$ | F | Cl | F |
| I.a.1.139 | OSO$_2$CH$_3$ | CH$_3$ | H | H |
| I.a.1.140 | OSO$_2$CH$_3$ | CH$_3$ | H | F |
| I.a.1.141 | OSO$_2$CH$_3$ | CH$_3$ | F | H |
| I.a.1.142 | OSO$_2$CH$_3$ | CH$_3$ | F | F |
| I.a.1.143 | OSO$_2$CH$_3$ | CH$_3$ | Cl | H |
| I.a.1.144 | OSO$_2$CH$_3$ | CH$_3$ | Cl | F |
| I.a.1.145 | SH | H | H | H |
| I.a.1.146 | SH | H | H | F |
| I.a.1.147 | SH | H | F | H |
| I.a.1.148 | SH | H | F | F |
| I.a.1.149 | SH | H | Cl | H |
| I.a.1.150 | SH | H | Cl | F |
| I.a.1.151 | SH | F | H | H |
| I.a.1.152 | SH | F | H | F |
| I.a.1.153 | SH | F | F | H |
| I.a.1.154 | SH | F | F | F |
| I.a.1.155 | SH | F | Cl | H |
| I.a.1.156 | SH | F | Cl | F |
| I.a.1.157 | SH | CH$_3$ | H | H |
| I.a.1.158 | SH | CH$_3$ | H | F |
| I.a.1.159 | SH | CH$_3$ | F | H |
| I.a.1.160 | SH | CH$_3$ | F | F |
| I.a.1.161 | SH | CH$_3$ | Cl | H |
| I.a.1.162 | SH | CH$_3$ | Cl | F |
| I.a.1.163 | SC(O)CH$_3$ | H | H | H |
| I.a.1.164 | SC(O)CH$_3$ | H | H | F |
| I.a.1.165 | SC(O)CH$_3$ | H | F | H |
| I.a.1.166 | SC(O)CH$_3$ | H | F | F |
| I.a.1.167 | SC(O)CH$_3$ | H | Cl | H |
| I.a.1.168 | SC(O)CH$_3$ | H | Cl | F |
| I.a.1.169 | SC(O)CH$_3$ | F | H | H |
| I.a.1.170 | SC(O)CH$_3$ | F | H | F |
| I.a.1.171 | SC(O)CH$_3$ | F | F | H |
| I.a.1.172 | SC(O)CH$_3$ | F | F | F |
| I.a.1.173 | SC(O)CH$_3$ | F | Cl | H |
| I.a.1.174 | SC(O)CH$_3$ | F | Cl | F |
| I.a.1.175 | SC(O)CH$_3$ | CH$_3$ | H | H |
| I.a.1.176 | SC(O)CH$_3$ | CH$_3$ | H | F |
| I.a.1.177 | SC(O)CH$_3$ | CH$_3$ | F | H |
| I.a.1.178 | SC(O)CH$_3$ | CH$_3$ | F | F |
| I.a.1.179 | SC(O)CH$_3$ | CH$_3$ | Cl | H |
| I.a.1.180 | SC(O)CH$_3$ | CH$_3$ | Cl | F |
| I.a.1.181 | SC(O)tertC$_4$H$_9$ | H | H | H |
| I.a.1.182 | SC(O)tertC$_4$H$_9$ | H | H | F |
| I.a.1.183 | SC(O)tertC$_4$H$_9$ | H | F | H |
| I.a.1.184 | SC(O)tertC$_4$H$_9$ | H | F | F |
| I.a.1.185 | SC(O)tertC$_4$H$_9$ | H | Cl | H |
| I.a.1.186 | SC(O)tertC$_4$H$_9$ | H | Cl | F |
| I.a.1.187 | SC(O)tertC$_4$H$_9$ | F | H | H |
| I.a.1.188 | SC(O)tertC$_4$H$_9$ | F | H | F |
| I.a.1.189 | SC(O)tertC$_4$H$_9$ | F | F | H |
| I.a.1.190 | SC(O)tertC$_4$H$_9$ | F | F | F |
| I.a.1.191 | SC(O)tertC$_4$H$_9$ | F | Cl | H |
| I.a.1.192 | SC(O)tertC$_4$H$_9$ | F | Cl | F |
| I.a.1.193 | SC(O)tertC$_4$H$_9$ | CH$_3$ | H | H |
| I.a.1.194 | SC(O)tertC$_4$H$_9$ | CH$_3$ | H | F |
| I.a.1.195 | SC(O)tertC$_4$H$_9$ | CH$_3$ | F | H |
| I.a.1.196 | SC(O)tertC$_4$H$_9$ | CH$_3$ | F | F |
| I.a.1.197 | SC(O)tertC$_4$H$_9$ | CH$_3$ | Cl | H |
| I.a.1.198 | SC(O)tertC$_4$H$_9$ | CH$_3$ | Cl | F |
| I.a.1.199 | SC(O)NH(CH$_3$) | H | H | H |
| I.a.1.200 | SC(O)NH(CH$_3$) | H | H | F |
| I.a.1.201 | SC(O)NH(CH$_3$) | H | F | H |
| I.a.1.202 | SC(O)NH(CH$_3$) | H | F | F |
| I.a.1.203 | SC(O)NH(CH$_3$) | H | Cl | H |
| I.a.1.204 | SC(O)NH(CH$_3$) | H | Cl | F |
| I.a.1.205 | SC(O)NH(CH$_3$) | F | H | H |
| I.a.1.206 | SC(O)NH(CH$_3$) | F | H | F |
| I.a.1.207 | SC(O)NH(CH$_3$) | F | F | H |
| I.a.1.208 | SC(O)NH(CH$_3$) | F | F | F |
| I.a.1.209 | SC(O)NH(CH$_3$) | F | Cl | H |
| I.a.1.210 | SC(O)NH(CH$_3$) | F | Cl | F |
| I.a.1.211 | SC(O)NH(CH$_3$) | CH$_3$ | H | H |
| I.a.1.212 | SC(O)NH(CH$_3$) | CH$_3$ | H | F |
| I.a.1.213 | SC(O)NH(CH$_3$) | CH$_3$ | F | H |
| I.a.1.214 | SC(O)NH(CH$_3$) | CH$_3$ | F | F |
| I.a.1.215 | SC(O)NH(CH$_3$) | CH$_3$ | Cl | H |
| I.a.1.216 | SC(O)NH(CH$_3$) | CH$_3$ | Cl | F |
| I.a.1.217 | SC(O)NH(C$_6$H$_5$) | H | H | H |
| I.a.1.218 | SC(O)NH(C$_6$H$_5$) | H | H | F |
| I.a.1.219 | SC(O)NH(C$_6$H$_5$) | H | F | H |
| I.a.1.220 | SC(O)NH(C$_6$H$_5$) | H | F | F |
| I.a.1.221 | SC(O)NH(C$_6$H$_5$) | H | Cl | H |
| I.a.1.222 | SC(O)NH(C$_6$H$_5$) | H | Cl | F |
| I.a.1.223 | SC(O)NH(C$_6$H$_5$) | F | H | H |
| I.a.1.224 | SC(O)NH(C$_6$H$_5$) | F | H | F |
| I.a.1.225 | SC(O)NH(C$_6$H$_5$) | F | F | H |
| I.a.1.226 | SC(O)NH(C$_6$H$_5$) | F | F | F |
| I.a.1.227 | SC(O)NH(C$_6$H$_5$) | F | Cl | H |
| I.a.1.228 | SC(O)NH(C$_6$H$_5$) | F | Cl | F |
| I.a.1.229 | SC(O)NH(C$_6$H$_5$) | CH$_3$ | H | H |
| I.a.1.230 | SC(O)NH(C$_6$H$_5$) | CH$_3$ | H | F |
| I.a.1.231 | SC(O)NH(C$_6$H$_5$) | CH$_3$ | F | H |
| I.a.1.232 | SC(O)NH(C$_6$H$_5$) | CH$_3$ | F | F |
| I.a.1.233 | SC(O)NH(C$_6$H$_5$) | CH$_3$ | Cl | H |
| I.a.1.234 | SC(O)NH(C$_6$H$_5$) | CH$_3$ | Cl | F |
| I.a.1.235 | SC(O)N(CH$_3$)$_2$ | H | H | H |
| I.a.1.236 | SC(O)N(CH$_3$)$_2$ | H | H | F |
| I.a.1.237 | SC(O)N(CH$_3$)$_2$ | H | F | H |
| I.a.1.238 | SC(O)N(CH$_3$)$_2$ | H | F | F |
| I.a.1.239 | SC(O)N(CH$_3$)$_2$ | H | Cl | H |
| I.a.1.240 | SC(O)N(CH$_3$)$_2$ | H | Cl | F |
| I.a.1.241 | SC(O)N(CH$_3$)$_2$ | F | H | H |
| I.a.1.242 | SC(O)N(CH$_3$)$_2$ | F | H | F |
| I.a.1.243 | SC(O)N(CH$_3$)$_2$ | F | F | H |
| I.a.1.244 | SC(O)N(CH$_3$)$_2$ | F | F | F |
| I.a.1.245 | SC(O)N(CH$_3$)$_2$ | F | Cl | H |
| I.a.1.246 | SC(O)N(CH$_3$)$_2$ | F | Cl | F |

TABLE 1-continued

I.a.1

| No. | R⁹ | R¹¹ | R¹² | R¹³ |
|---|---|---|---|---|
| I.a.1.247 | SC(O)N(CH₃)₂ | CH₃ | H | H |
| I.a.1.248 | SC(O)N(CH₃)₂ | CH₃ | H | F |
| I.a.1.249 | SC(O)N(CH₃)₂ | CH₃ | F | H |
| I.a.1.250 | SC(O)N(CH₃)₂ | CH₃ | F | F |
| I.a.1.251 | SC(O)N(CH₃)₂ | CH₃ | Cl | H |
| I.a.1.252 | SC(O)N(CH₃)₂ | CH₃ | Cl | F |
| I.a.1.253 | SC(O)N(CH₃)(C₆H₅) | H | H | H |
| I.a.1.254 | SC(O)N(CH₃)(C₆H₅) | H | H | F |
| I.a.1.255 | SC(O)N(CH₃)(C₆H₅) | H | F | H |
| I.a.1.256 | SC(O)N(CH₃)(C₆H₅) | H | F | F |
| I.a.1.257 | SC(O)N(CH₃)(C₆H₅) | H | Cl | H |
| I.a.1.258 | SC(O)N(CH₃)(C₆H₅) | H | Cl | F |
| I.a.1.259 | SC(O)N(CH₃)(C₆H₅) | F | H | H |
| I.a.1.260 | SC(O)N(CH₃)(C₆H₅) | F | H | F |
| I.a.1.261 | SC(O)N(CH₃)(C₆H₅) | F | F | H |
| I.a.1.262 | SC(O)N(CH₃)(C₆H₅) | F | F | F |
| I.a.1.263 | SC(O)N(CH₃)(C₆H₅) | F | Cl | H |
| I.a.1.264 | SC(O)N(CH₃)(C₆H₅) | F | Cl | F |
| I.a.1.265 | SC(O)N(CH₃)(C₆H₅) | CH₃ | H | H |
| I.a.1.266 | SC(O)N(CH₃)(C₆H₅) | CH₃ | H | F |
| I.a.1.267 | SC(O)N(CH₃)(C₆H₅) | CH₃ | F | H |
| I.a.1.268 | SC(O)N(CH₃)(C₆H₅) | CH₃ | F | F |
| I.a.1.269 | SC(O)N(CH₃)(C₆H₅) | CH₃ | Cl | H |
| I.a.1.270 | SC(O)N(CH₃)(C₆H₅) | CH₃ | Cl | F |
| I.a.1.271 | NH₂ | H | H | H |
| I.a.1.272 | NH₂ | H | H | F |
| I.a.1.273 | NH₂ | H | F | H |
| I.a.1.274 | NH₂ | H | F | F |
| I.a.1.275 | NH₂ | H | Cl | H |
| I.a.1.276 | NH₂ | H | Cl | F |
| I.a.1.277 | NH₂ | F | H | H |
| I.a.1.278 | NH₂ | F | H | F |
| I.a.1.279 | NH₂ | F | F | H |
| I.a.1.280 | NH₂ | F | F | F |
| I.a.1.281 | NH₂ | F | Cl | H |
| I.a.1.282 | NH₂ | F | Cl | F |
| I.a.1.283 | NH₂ | CH₃ | H | H |
| I.a.1.284 | NH₂ | CH₃ | H | F |
| I.a.1.285 | NH₂ | CH₃ | F | H |
| I.a.1.286 | NH₂ | CH₃ | F | F |
| I.a.1.287 | NH₂ | CH₃ | Cl | H |
| I.a.1.288 | NH₂ | CH₃ | Cl | F |
| I.a.1.289 | NHC(O)CH₃ | H | H | H |
| I.a.1.290 | NHC(O)CH₃ | H | H | F |
| I.a.1.291 | NHC(O)CH₃ | H | F | H |
| I.a.1.292 | NHC(O)CH₃ | H | F | F |
| I.a.1.293 | NHC(O)CH₃ | H | Cl | H |
| I.a.1.294 | NHC(O)CH₃ | H | Cl | F |
| I.a.1.295 | NHC(O)CH₃ | F | H | H |
| I.a.1.296 | NHC(O)CH₃ | F | H | F |
| I.a.1.297 | NHC(O)CH₃ | F | F | H |
| I.a.1.298 | NHC(O)CH₃ | F | F | F |
| I.a.1.299 | NHC(O)CH₃ | F | Cl | H |
| I.a.1.300 | NHC(O)CH₃ | F | Cl | F |
| I.a.1.301 | NHC(O)CH₃ | CH₃ | H | H |
| I.a.1.302 | NHC(O)CH₃ | CH₃ | H | F |
| I.a.1.303 | NHC(O)CH₃ | CH₃ | F | H |
| I.a.1.304 | NHC(O)CH₃ | CH₃ | F | F |
| I.a.1.305 | NHC(O)CH₃ | CH₃ | Cl | H |
| I.a.1.306 | NHC(O)CH₃ | CH₃ | Cl | F |
| I.a.1.307 | NHC(O)tertC₄H₉ | H | H | H |
| I.a.1.308 | NHC(O)tertC₄H₉ | H | H | F |
| I.a.1.309 | NHC(O)tertC₄H₉ | H | F | H |
| I.a.1.310 | NHC(O)tertC₄H₉ | H | F | F |
| I.a.1.311 | NHC(O)tertC₄H₉ | H | Cl | H |
| I.a.1.312 | NHC(O)tertC₄H₉ | H | Cl | F |
| I.a.1.313 | NHC(O)tertC₄H₉ | F | H | H |
| I.a.1.314 | NHC(O)tertC₄H₉ | F | H | F |
| I.a.1.315 | NHC(O)tertC₄H₉ | F | F | H |
| I.a.1.316 | NHC(O)tertC₄H₉ | F | F | F |
| I.a.1.317 | NHC(O)tertC₄H₉ | F | Cl | H |
| I.a.1.318 | NHC(O)tertC₄H₉ | F | Cl | F |
| I.a.1.319 | NHC(O)tertC₄H₉ | CH₃ | H | H |
| I.a.1.320 | NHC(O)tertC₄H₉ | CH₃ | H | F |
| I.a.1.321 | NHC(O)tertC₄H₉ | CH₃ | F | H |
| I.a.1.322 | NHC(O)tertC₄H₉ | CH₃ | F | F |
| I.a.1.323 | NHC(O)tertC₄H₉ | CH₃ | Cl | H |
| I.a.1.324 | NHC(O)tertC₄H₉ | CH₃ | Cl | F |
| I.a.1.325 | NHC(O)NH(CH₃) | H | H | H |
| I.a.1.326 | NHC(O)NH(CH₃) | H | H | F |
| I.a.1.327 | NHC(O)NH(CH₃) | H | F | H |
| I.a.1.328 | NHC(O)NH(CH₃) | H | F | F |
| I.a.1.329 | NHC(O)NH(CH₃) | H | Cl | H |
| I.a.1.330 | NHC(O)NH(CH₃) | H | Cl | F |
| I.a.1.331 | NHC(O)NH(CH₃) | F | H | H |
| I.a.1.332 | NHC(O)NH(CH₃) | F | H | F |
| I.a.1.333 | NHC(O)NH(CH₃) | F | F | H |
| I.a.1.334 | NHC(O)NH(CH₃) | F | F | F |
| I.a.1.335 | NHC(O)NH(CH₃) | F | Cl | H |
| I.a.1.336 | NHC(O)NH(CH₃) | F | Cl | F |
| I.a.1.337 | NHC(O)NH(CH₃) | CH₃ | H | H |
| I.a.1.338 | NHC(O)NH(CH₃) | CH₃ | H | F |
| I.a.1.339 | NHC(O)NH(CH₃) | CH₃ | F | H |
| I.a.1.340 | NHC(O)NH(CH₃) | CH₃ | F | F |
| I.a.1.341 | NHC(O)NH(CH₃) | CH₃ | Cl | H |
| I.a.1.342 | NHC(O)NH(CH₃) | CH₃ | Cl | F |
| I.a.1.343 | NHC(O)NH(C₆H₅) | H | H | H |
| I.a.1.344 | NHC(O)NH(C₆H₅) | H | H | F |
| I.a.1.345 | NHC(O)NH(C₆H₅) | H | F | H |
| I.a.1.346 | NHC(O)NH(C₆H₅) | H | F | F |
| I.a.1.347 | NHC(O)NH(C₆H₅) | H | Cl | H |
| I.a.1.348 | NHC(O)NH(C₆H₅) | H | Cl | F |
| I.a.1.349 | NHC(O)NH(C₆H₅) | F | H | H |
| I.a.1.350 | NHC(O)NH(C₆H₅) | F | H | F |
| I.a.1.351 | NHC(O)NH(C₆H₅) | F | F | H |
| I.a.1.352 | NHC(O)NH(C₆H₅) | F | F | F |
| I.a.1.353 | NHC(O)NH(C₆H₅) | F | Cl | H |
| I.a.1.354 | NHC(O)NH(C₆H₅) | F | Cl | F |
| I.a.1.355 | NHC(O)NH(C₆H₅) | CH₃ | H | H |
| I.a.1.356 | NHC(O)NH(C₆H₅) | CH₃ | H | F |
| I.a.1.357 | NHC(O)NH(C₆H₅) | CH₃ | F | H |
| I.a.1.358 | NHC(O)NH(C₆H₅) | CH₃ | F | F |
| I.a.1.359 | NHC(O)NH(C₆H₅) | CH₃ | Cl | H |
| I.a.1.360 | NHC(O)NH(C₆H₅) | CH₃ | Cl | F |
| I.a.1.361 | NHC(O)N(CH₃)₂ | H | H | H |
| I.a.1.362 | NHC(O)N(CH₃)₂ | H | H | F |
| I.a.1.363 | NHC(O)N(CH₃)₂ | H | F | H |
| I.a.1.364 | NHC(O)N(CH₃)₂ | H | F | F |
| I.a.1.365 | NHC(O)N(CH₃)₂ | H | Cl | H |
| I.a.1.366 | NHC(O)N(CH₃)₂ | H | Cl | F |
| I.a.1.367 | NHC(O)N(CH₃)₂ | F | H | H |
| I.a.1.368 | NHC(O)N(CH₃)₂ | F | H | F |

TABLE 1-continued

I.a.1

| No. | R⁹ | R¹¹ | R¹² | R¹³ |
|---|---|---|---|---|
| I.a.1.369 | NHC(O)N(CH₃)₂ | F | F | H |
| I.a.1.370 | NHC(O)N(CH₃)₂ | F | F | F |
| I.a.1.371 | NHC(O)N(CH₃)₂ | F | Cl | H |
| I.a.1.372 | NHC(O)N(CH₃)₂ | F | Cl | F |
| I.a.1.373 | NHC(O)N(CH₃)₂ | CH₃ | H | H |
| I.a.1.374 | NHC(O)N(CH₃)₂ | CH₃ | H | F |
| I.a.1.375 | NHC(O)N(CH₃)₂ | CH₃ | F | H |
| I.a.1.376 | NHC(O)N(CH₃)₂ | CH₃ | F | F |
| I.a.1.377 | NHC(O)N(CH₃)₂ | CH₃ | Cl | H |
| I.a.1.378 | NHC(O)N(CH₃)₂ | CH₃ | Cl | F |
| I.a.1.379 | NHC(O)N(CH₃)(C₆H₅) | H | H | H |
| I.a.1.380 | NHC(O)N(CH₃)(C₆H₅) | H | H | F |
| I.a.1.381 | NHC(O)N(CH₃)(C₆H₅) | H | F | H |
| I.a.1.382 | NHC(O)N(CH₃)(C₆H₅) | H | F | F |
| I.a.1.383 | NHC(O)N(CH₃)(C₆H₅) | H | Cl | H |
| I.a.1.384 | NHC(O)N(CH₃)(C₆H₅) | H | Cl | F |
| I.a.1.385 | NHC(O)N(CH₃)(C₆H₅) | F | H | H |
| I.a.1.386 | NHC(O)N(CH₃)(C₆H₅) | F | H | F |
| I.a.1.387 | NHC(O)N(CH₃)(C₆H₅) | F | F | H |
| I.a.1.388 | NHC(O)N(CH₃)(C₆H₅) | F | F | F |
| I.a.1.389 | NHC(O)N(CH₃)(C₆H₅) | F | Cl | H |
| I.a.1.390 | NHC(O)N(CH₃)(C₆H₅) | F | Cl | F |
| I.a.1.391 | NHC(O)N(CH₃)(C₆H₅) | CH₃ | H | H |
| I.a.1.392 | NHC(O)N(CH₃)(C₆H₅) | CH₃ | H | F |
| I.a.1.393 | NHC(O)N(CH₃)(C₆H₅) | CH₃ | F | H |
| I.a.1.394 | NHC(O)N(CH₃)(C₆H₅) | CH₃ | F | F |
| I.a.1.395 | NHC(O)N(CH₃)(C₆H₅) | CH₃ | Cl | H |
| I.a.1.396 | NHC(O)N(CH₃)(C₆H₅) | CH₃ | Cl | F |
| I.a.1.397 | NHSO₂CH₃ | H | H | H |
| I.a.1.398 | NHSO₂CH₃ | H | H | F |
| I.a.1.399 | NHSO₂CH₃ | H | F | H |
| I.a.1.400 | NHSO₂CH₃ | H | F | F |
| I.a.1.401 | NHSO₂CH₃ | H | Cl | H |
| I.a.1.402 | NHSO₂CH₃ | H | Cl | F |
| I.a.1.403 | NHSO₂CH₃ | F | H | H |
| I.a.1.404 | NHSO₂CH₃ | F | H | F |
| I.a.1.405 | NHSO₂CH₃ | F | F | H |
| I.a.1.406 | NHSO₂CH₃ | F | F | F |
| I.a.1.407 | NHSO₂CH₃ | F | Cl | H |
| I.a.1.408 | NHSO₂CH₃ | F | Cl | F |
| I.a.1.409 | NHSO₂CH₃ | CH₃ | H | H |
| I.a.1.410 | NHSO₂CH₃ | CH₃ | H | F |
| I.a.1.411 | NHSO₂CH₃ | CH₃ | F | H |
| I.a.1.412 | NHSO₂CH₃ | CH₃ | F | F |
| I.a.1.413 | NHSO₂CH₃ | CH₃ | Cl | H |
| I.a.1.414 | NHSO₂CH₃ | CH₃ | Cl | F |
| I.a.1.415 | NH(CH₃) | H | H | H |
| I.a.1.416 | NH(CH₃) | H | H | F |
| I.a.1.417 | NH(CH₃) | H | F | H |
| I.a.1.418 | NH(CH₃) | H | F | F |
| I.a.1.419 | NH(CH₃) | H | Cl | H |
| I.a.1.420 | NH(CH₃) | H | Cl | F |
| I.a.1.421 | NH(CH₃) | F | H | H |
| I.a.1.422 | NH(CH₃) | F | H | F |
| I.a.1.423 | NH(CH₃) | F | F | H |
| I.a.1.424 | NH(CH₃) | F | F | F |
| I.a.1.425 | NH(CH₃) | F | Cl | H |
| I.a.1.426 | NH(CH₃) | F | Cl | F |
| I.a.1.427 | NH(CH₃) | CH₃ | H | H |
| I.a.1.428 | NH(CH₃) | CH₃ | H | F |
| I.a.1.429 | NH(CH₃) | CH₃ | F | H |
| I.a.1.430 | NH(CH₃) | CH₃ | F | F |
| I.a.1.431 | NH(CH₃) | CH₃ | Cl | H |
| I.a.1.432 | NH(CH₃) | CH₃ | Cl | F |
| I.a.1.433 | N(CH₃)C(O)CH₃ | H | H | H |
| I.a.1.434 | N(CH₃)C(O)CH₃ | H | H | F |
| I.a.1.435 | N(CH₃)C(O)CH₃ | H | F | H |
| I.a.1.436 | N(CH₃)C(O)CH₃ | H | F | F |
| I.a.1.437 | N(CH₃)C(O)CH₃ | H | Cl | H |
| I.a.1.438 | N(CH₃)C(O)CH₃ | H | Cl | F |
| I.a.1.439 | N(CH₃)C(O)CH₃ | F | H | H |
| I.a.1.440 | N(CH₃)C(O)CH₃ | F | H | F |
| I.a.1.441 | N(CH₃)C(O)CH₃ | F | F | H |
| I.a.1.442 | N(CH₃)C(O)CH₃ | F | F | F |
| I.a.1.443 | N(CH₃)C(O)CH₃ | F | Cl | H |
| I.a.1.444 | N(CH₃)C(O)CH₃ | F | Cl | F |
| I.a.1.445 | N(CH₃)C(O)CH₃ | CH₃ | H | H |
| I.a.1.446 | N(CH₃)C(O)CH₃ | CH₃ | H | F |
| I.a.1.447 | N(CH₃)C(O)CH₃ | CH₃ | F | H |
| I.a.1.448 | N(CH₃)C(O)CH₃ | CH₃ | F | F |
| I.a.1.449 | N(CH₃)C(O)CH₃ | CH₃ | Cl | H |
| I.a.1.450 | N(CH₃)C(O)CH₃ | CH₃ | Cl | F |
| I.a.1.451 | N(CH₃)C(O)tertC₄H₉ | H | H | H |
| I.a.1.452 | N(CH₃)C(O)tertC₄H₉ | H | H | F |
| I.a.1.453 | N(CH₃)C(O)tertC₄H₉ | H | F | H |
| I.a.1.454 | N(CH₃)C(O)tertC₄H₉ | H | F | F |
| I.a.1.455 | N(CH₃)C(O)tertC₄H₉ | H | Cl | H |
| I.a.1.456 | N(CH₃)C(O)tertC₄H₉ | H | Cl | F |
| I.a.1.457 | N(CH₃)C(O)tertC₄H₉ | F | H | H |
| I.a.1.458 | N(CH₃)C(O)tertC₄H₉ | F | H | F |
| I.a.1.459 | N(CH₃)C(O)tertC₄H₉ | F | F | H |
| I.a.1.460 | N(CH₃)C(O)tertC₄H₉ | F | F | F |
| I.a.1.461 | N(CH₃)C(O)tertC₄H₉ | F | Cl | H |
| I.a.1.462 | N(CH₃)C(O)tertC₄H₉ | F | Cl | F |
| I.a.1.463 | N(CH₃)C(O)tertC₄H₉ | CH₃ | H | H |
| I.a.1.464 | N(CH₃)C(O)tertC₄H₉ | CH₃ | H | F |
| I.a.1.465 | N(CH₃)C(O)tertC₄H₉ | CH₃ | F | H |
| I.a.1.466 | N(CH₃)C(O)tertC₄H₉ | CH₃ | F | F |
| I.a.1.467 | N(CH₃)C(O)tertC₄H₉ | CH₃ | Cl | H |
| I.a.1.468 | N(CH₃)C(O)tertC₄H₉ | CH₃ | Cl | F |
| I.a.1.469 | N(CH₃)C(O)NH(CH₃) | H | H | H |
| I.a.1.470 | N(CH₃)C(O)NH(CH₃) | H | H | F |
| I.a.1.471 | N(CH₃)C(O)NH(CH₃) | H | F | H |
| I.a.1.472 | N(CH₃)C(O)NH(CH₃) | H | F | F |
| I.a.1.473 | N(CH₃)C(O)NH(CH₃) | H | Cl | H |
| I.a.1.474 | N(CH₃)C(O)NH(CH₃) | H | Cl | F |
| I.a.1.475 | N(CH₃)C(O)NH(CH₃) | F | H | H |
| I.a.1.476 | N(CH₃)C(O)NH(CH₃) | F | H | F |
| I.a.1.477 | N(CH₃)C(O)NH(CH₃) | F | F | H |
| I.a.1.478 | N(CH₃)C(O)NH(CH₃) | F | F | F |
| I.a.1.479 | N(CH₃)C(O)NH(CH₃) | F | Cl | H |
| I.a.1.480 | N(CH₃)C(O)NH(CH₃) | F | Cl | F |
| I.a.1.481 | N(CH₃)C(O)NH(CH₃) | CH₃ | H | H |
| I.a.1.482 | N(CH₃)C(O)NH(CH₃) | CH₃ | H | F |
| I.a.1.483 | N(CH₃)C(O)NH(CH₃) | CH₃ | F | H |
| I.a.1.484 | N(CH₃)C(O)NH(CH₃) | CH₃ | F | F |
| I.a.1.485 | N(CH₃)C(O)NH(CH₃) | CH₃ | Cl | H |
| I.a.1.486 | N(CH₃)C(O)NH(CH₃) | CH₃ | Cl | F |
| I.a.1.487 | N(CH₃)C(O)NH(C₆H₅) | H | H | H |
| I.a.1.488 | N(CH₃)C(O)NH(C₆H₅) | H | H | F |
| I.a.1.489 | N(CH₃)C(O)NH(C₆H₅) | H | F | H |
| I.a.1.490 | N(CH₃)C(O)NH(C₆H₅) | H | F | F |

TABLE 1-continued

I.a.1

| No. | R⁹ | R¹¹ | R¹² | R¹³ |
|---|---|---|---|---|
| I.a.1.491 | N(CH₃)C(O)NH(C₆H₅) | H | Cl | H |
| I.a.1.492 | N(CH₃)C(O)NH(C₆H₅) | H | Cl | F |
| I.a.1.493 | N(CH₃)C(O)NH(C₆H₅) | F | H | H |
| I.a.1.494 | N(CH₃)C(O)NH(C₆H₅) | F | H | F |
| I.a.1.495 | N(CH₃)C(O)NH(C₆H₅) | F | F | H |
| I.a.1.496 | N(CH₃)C(O)NH(C₆H₅) | F | F | F |
| I.a.1.497 | N(CH₃)C(O)NH(C₆H₅) | F | Cl | H |
| I.a.1.498 | N(CH₃)C(O)NH(C₆H₅) | F | Cl | F |
| I.a.1.499 | N(CH₃)C(O)NH(C₆H₅) | CH₃ | H | H |
| I.a.1.500 | N(CH₃)C(O)NH(C₆H₅) | CH₃ | H | F |
| I.a.1.501 | N(CH₃)C(O)NH(C₆H₅) | CH₃ | F | H |
| I.a.1.502 | N(CH₃)C(O)NH(C₆H₅) | CH₃ | F | F |
| I.a.1.503 | N(CH₃)C(O)NH(C₆H₅) | CH₃ | Cl | H |
| I.a.1.504 | N(CH₃)C(O)NH(C₆H₅) | CH₃ | Cl | F |
| I.a.1.505 | N(CH₃)C(O)N(CH₃)₂ | H | H | H |
| I.a.1.506 | N(CH₃)C(O)N(CH₃)₂ | H | H | F |
| I.a.1.507 | N(CH₃)C(O)N(CH₃)₂ | H | F | H |
| I.a.1.508 | N(CH₃)C(O)N(CH₃)₂ | H | F | F |
| I.a.1.509 | N(CH₃)C(O)N(CH₃)₂ | H | Cl | H |
| I.a.1.510 | N(CH₃)C(O)N(CH₃)₂ | H | Cl | F |
| I.a.1.511 | N(CH₃)C(O)N(CH₃)₂ | F | H | H |
| I.a.1.512 | N(CH₃)C(O)N(CH₃)₂ | F | H | F |
| I.a.1.513 | N(CH₃)C(O)N(CH₃)₂ | F | F | H |
| I.a.1.514 | N(CH₃)C(O)N(CH₃)₂ | F | F | F |
| I.a.1.515 | N(CH₃)C(O)N(CH₃)₂ | F | Cl | H |
| I.a.1.516 | N(CH₃)C(O)N(CH₃)₂ | F | Cl | F |
| I.a.1.517 | N(CH₃)C(O)N(CH₃)₂ | CH₃ | H | H |
| I.a.1.518 | N(CH₃)C(O)N(CH₃)₂ | CH₃ | H | F |
| I.a.1.519 | N(CH₃)C(O)N(CH₃)₂ | CH₃ | F | H |
| I.a.1.520 | N(CH₃)C(O)N(CH₃)₂ | CH₃ | F | F |
| I.a.1.521 | N(CH₃)C(O)N(CH₃)₂ | CH₃ | Cl | H |
| I.a.1.522 | N(CH₃)C(O)N(CH₃)₂ | CH₃ | Cl | F |
| I.a.1.523 | N(CH₃)C(O)N(CH₃)(C₆H₅) | H | H | H |
| I.a.1.524 | N(CH₃)C(O)N(CH₃)(C₆H₅) | H | H | F |
| I.a.1.525 | N(CH₃)C(O)N(CH₃)(C₆H₅) | H | F | H |
| I.a.1.526 | N(CH₃)C(O)N(CH₃)(C₆H₅) | H | F | F |
| I.a.1.527 | N(CH₃)C(O)N(CH₃)(C₆H₅) | H | Cl | H |
| I.a.1.528 | N(CH₃)C(O)N(CH₃)(C₆H₅) | H | Cl | F |
| I.a.1.529 | N(CH₃)C(O)N(CH₃)(C₆H₅) | F | H | H |
| I.a.1.530 | N(CH₃)C(O)N(CH₃)(C₆H₅) | F | H | F |
| I.a.1.531 | N(CH₃)C(O)N(CH₃)(C₆H₅) | F | F | H |
| I.a.1.532 | N(CH₃)C(O)N(CH₃)(C₆H₅) | F | F | F |
| I.a.1.533 | N(CH₃)C(O)N(CH₃)(C₆H₅) | F | Cl | H |
| I.a.1.534 | N(CH₃)C(O)N(CH₃)(C₆H₅) | F | Cl | F |
| I.a.1.535 | N(CH₃)C(O)N(CH₃)(C₆H₅) | CH₃ | H | H |
| I.a.1.536 | N(CH₃)C(O)N(CH₃)(C₆H₅) | CH₃ | H | F |
| I.a.1.537 | N(CH₃)C(O)N(CH₃)(C₆H₅) | CH₃ | F | H |
| I.a.1.538 | N(CH₃)C(O)N(CH₃)(C₆H₅) | CH₃ | F | F |
| I.a.1.539 | N(CH₃)C(O)N(CH₃)(C₆H₅) | CH₃ | Cl | H |
| I.a.1.540 | N(CH₃)C(O)N(CH₃)(C₆H₅) | CH₃ | Cl | F |
| I.a.1.541 | N(CH₃)SO₂CH₃ | H | H | H |
| I.a.1.542 | N(CH₃)SO₂CH₃ | H | H | F |
| I.a.1.543 | N(CH₃)SO₂CH₃ | H | F | H |
| I.a.1.544 | N(CH₃)SO₂CH₃ | H | F | F |
| I.a.1.545 | N(CH₃)SO₂CH₃ | H | Cl | H |
| I.a.1.546 | N(CH₃)SO₂CH₃ | H | Cl | F |
| I.a.1.547 | N(CH₃)SO₂CH₃ | F | H | H |
| I.a.1.548 | N(CH₃)SO₂CH₃ | F | H | F |
| I.a.1.549 | N(CH₃)SO₂CH₃ | F | F | H |
| I.a.1.550 | N(CH₃)SO₂CH₃ | F | F | F |
| I.a.1.551 | N(CH₃)SO₂CH₃ | F | Cl | H |
| I.a.1.552 | N(CH₃)SO₂CH₃ | F | Cl | F |
| I.a.1.553 | N(CH₃)SO₂CH₃ | CH₃ | H | H |
| I.a.1.554 | N(CH₃)SO₂CH₃ | CH₃ | H | F |
| I.a.1.555 | N(CH₃)SO₂CH₃ | CH₃ | F | H |
| I.a.1.556 | N(CH₃)SO₂CH₃ | CH₃ | F | F |
| I.a.1.557 | N(CH₃)SO₂CH₃ | CH₃ | Cl | H |
| I.a.1.558 | N(CH₃)SO₂CH₃ | CH₃ | Cl | F |

Most preference is also given to the compounds of the formula I.a.2, in particular to the compounds of the formulae I.a.2.1 to I.a.2.558 which differ from the corresponding compounds of the formulae I.a.1.1 to I.a.1.558 in that $R^2$ is $CF_3$.

I.a.2

Most preference is also given to the compounds of the formula I.a.3, in particular to the compounds of the formulae I.a.3.1 to I.a.3.558 which differ from the corresponding compounds of the formulae I.a.1.1 to I.a.1.558 in that $R^2$ is $CF_3$ and $R^3$ is fluorine.

I.a.3

Most preference is also given to the compounds of the formula I.a.4, in particular to the compounds of the formulae I.a.4.1 to I.a.4.558 which differ from the corresponding compounds of the formulae I.a.1.1 to I.a.1.558 in that $R^2$ is $CF_3$ and $R^3$ is chlorine.

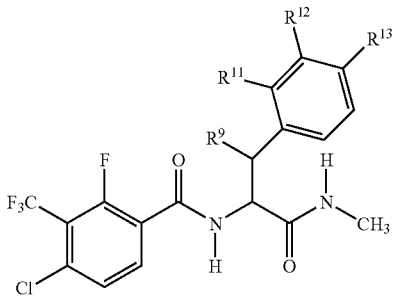

I.a.4

Most preference is also given to the compounds of the formula I.a.5, in particular to the compounds of the formulae I.a.5.1 to I.a.5.558 which differ from the corresponding compounds of the formulae I.a.1.1 to I.a.1.558 in that $R^1$ is chlorine and $R^3$ is fluorine.

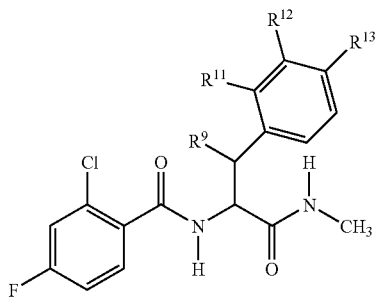

I.a.5

Most preference is also given to the compounds of the formula I.a.6, in particular to the compounds of the formulae I.a.6.1 to I.a.6.558 which differ from the corresponding compounds of the formulae I.a.1.1 to I.a.1.558 in that $R^1$ and $R^3$ are chlorine.

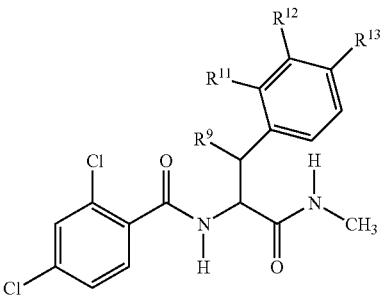

I.a.6

Most preference is also given to the compounds of the formula I.a.7, in particular to the compounds of the formulae I.a.7.1 to I.a.7.558 which differ from the corresponding compounds of the formulae I.a.1.1 to I.a.1.558 in that $R^1$ is chlorine and $R^2$ is fluorine.

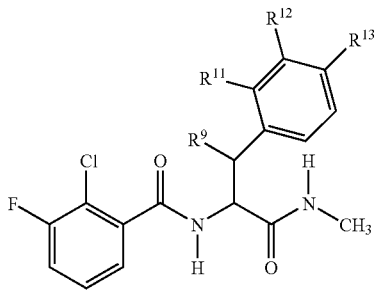

I.a.7

Most preference is also given to the compounds of the formula I.a.8, in particular to the compounds of the formulae I.a.8.1 to I.a.8.558 which differ from the corresponding compounds of the formulae I.a.1.1 to I.a.1.558 in that $R^1$ is chlorine and $R^2$ and $R^3$ are fluorine.

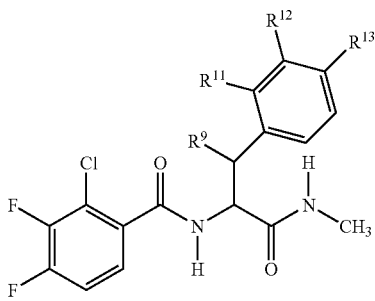

I.a.8

Most preference is also given to the compounds of the formula I.a.9, in particular to the compounds of the formulae I.a.9.1 to I.a.9.558 which differ from the corresponding compounds of the formulae I.a.1.1 to I.a.1.558 in that $R^1$ and $R^3$ are chlorine and $R^2$ is fluorine.

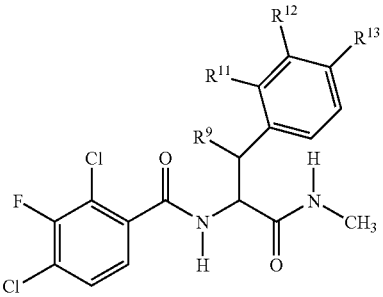

I.a.9

Most preference is also given to the compounds of the formula I.a.10, in particular to the compounds of the formulae I.a.10.1 to I.a.10.558 which differ from the corresponding compounds of the formulae I.a.1.1 to I.a.1.558 in that $R^1$ and $R^2$ are chlorine.

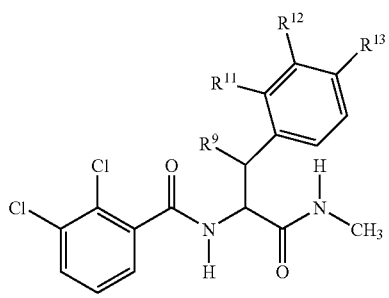

I.a.10

Most preference is also given to the compounds of the formula I.a.11, in particular to the compounds of the formulae I.a.11.1 to I.a.11.558 which differ from the corresponding compounds of the formulae I.a.1.1 to I.a.1.558 in that $R^1$ and $R^2$ are chlorine and $R^3$ is fluorine.

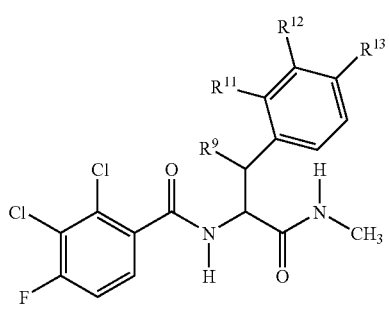

I.a.11

Most preference is also given to the compounds of the formula I.a.12, in particular to the compounds of the formulae I.a.12.1 to I.a.12.558 which differ from the corresponding compounds of the formulae I.a.1.1 to I.a.1.558 in that $R^1$, $R^2$ and $R^3$ are chlorine.

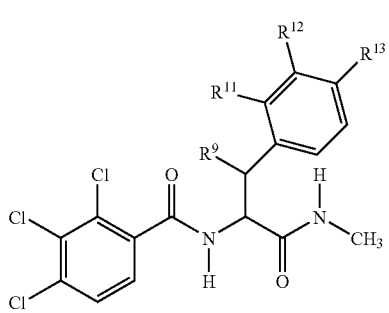

I.a.12

Most preference is also given to the compounds of the formula I.a.13, in particular to the compounds of the formulae I.a.13.1 to I.a.13.558 which differ from the corresponding compounds of the formulae I.a.1.1 to I.a.1.558 in that $R^1$ is chlorine and $R^2$ is $CF_3$.

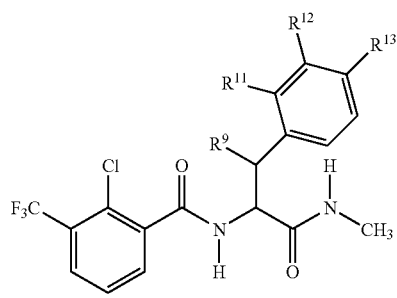

I.a.13

Most preference is also given to the compounds of the formula I.a.14, in particular to the compounds of the formulae I.a.14.1 to I.a.14.558 which differ from the corresponding compounds of the formulae I.a.1.1 to I.a.1.558 in that $R^1$ is chlorine, $R^2$ is $CF_3$ and $R^3$ is fluorine.

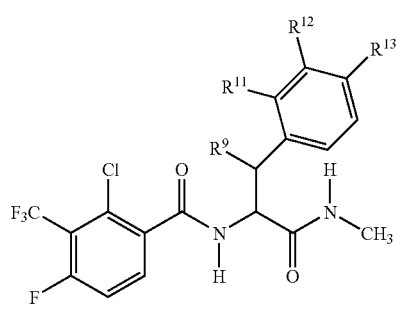

I.a.14

Most preference is also given to the compounds of the formula I.a.15, in particular to the compounds of the formulae I.a.15.1 to I.a.15.558 which differ from the corresponding compounds of the formulae I.a.1.1 to I.a.1.558 in that $R^1$ and $R^3$ are chlorine and $R^2$ is $CF_3$.

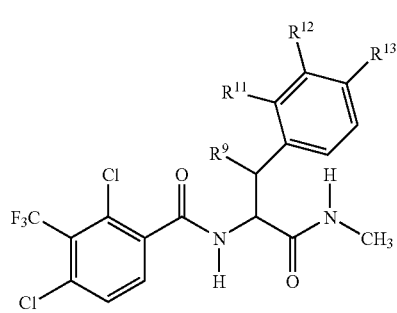

I.a.15

Most preference is also given to the compounds of the formulae I.a.16, in particular to the compounds of the formulae I.a.16.1 to I.a.16.558 which differ from the corresponding compounds of the formulae I.a.1.1 to I.a.1.558 in that $R^1$ is $CF_3$.

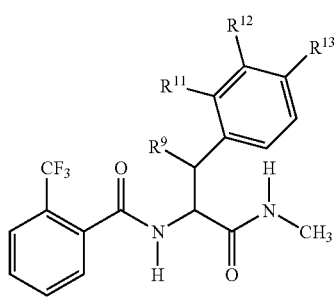

I.a.16

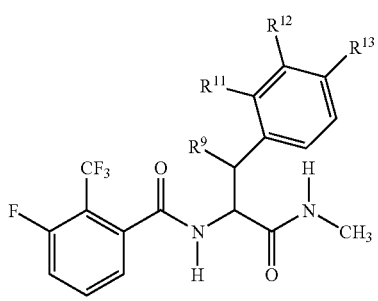

I.a.19

Most preference is also given to the compounds of the formula I.a.17, in particular to the compounds of the formulae I.a.17.1 to I.a.17.558 which differ from the corresponding compounds of the formulae I.a.1.1 to I.a.1.558 in that $R^1$ is $CF_3$ and $R^3$ is fluorine.

Most preference is also given to the compounds of the formula I.a.20, in particular to the compounds of the formulae I.a.20.1 to I.a.20.558 which differ from the corresponding compounds of the formulae I.a.1.1 to I.a.1.558 in that $R^1$ is $CF_3$ and $R^2$ and $R^3$ are fluorine.

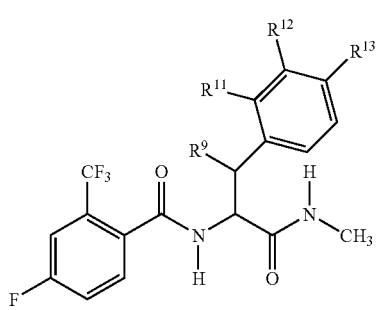

I.a.17

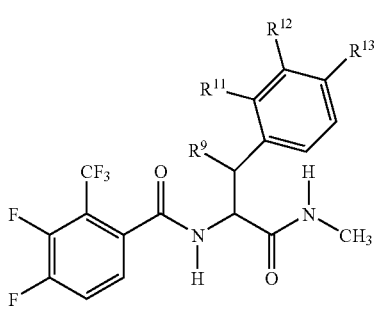

I.a.20

Most preference is also given to the compounds of the formula I.a.18, in particular to the compounds of the formulae I.a.18.1 to I.a.18.558 which differ from the corresponding compounds of the formulae I.a.1.1 to I.a.1.558 in that $R^1$ is $CF_3$ and $R^3$ is chlorine.

Most preference is also given to the compounds of the formula I.a.21, in particular to the compounds of the formulae I.a.21.1 to I.a.21.558 which differ from the corresponding compounds of the formulae I.a.1.1 to I.a.1.558 in that $R^1$ is $CF_3$, $R^2$ is fluorine and $R^3$ is chlorine.

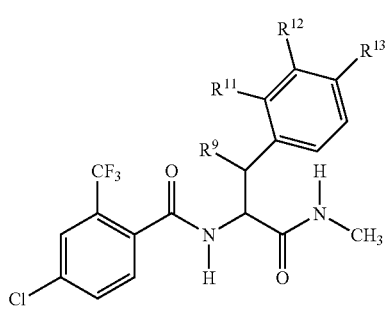

I.a.18

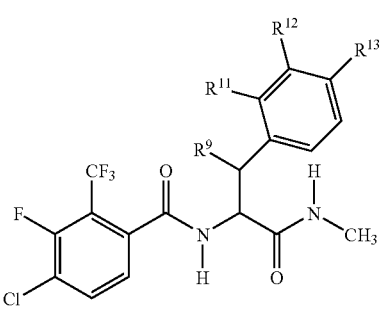

I.a.21

Most preference is also given to the compounds of the formula I.a.19, in particular to the compounds of the formulae I.a.19.1 to I.a.19.558 which differ from the corresponding compounds of the formulae I.a.1.1 to I.a.1.558 in that $R^1$ is $CF_3$ and $R^2$ is fluorine.

Most preference is also given to the compounds of the formula I.a.22, in particular to the compounds of the formulae I.a.22.1 to I.a.22.558 which differ from the corresponding compounds of the formulae I.a.1.1 to I.a.1.558 in that $R^1$ is $CF_3$ and $R^2$ is chlorine.

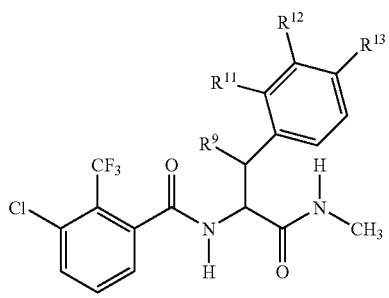

I.a.22

Most preference is also given to the compounds of the formula I.a.23, in particular to the compounds of the formulae I.a.23.1 to I.a.23.558 which differ from the corresponding compounds of the formulae I.a.1.1 to I.a.1.558 in that $R^1$ is $CF_3$, $R^2$ is chlorine and $R^3$ is fluorine.

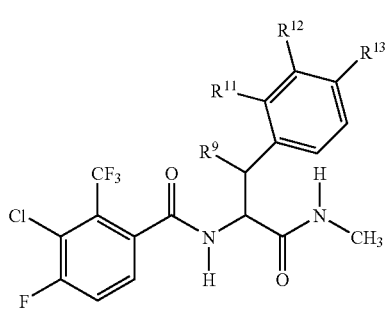

I.a.23

Most preference is also given to the compounds of the formula I.a.24, in particular to the compounds of the formulae I.a.24.1 to I.a.24.558 which differ from the corresponding compounds of the formulae I.a.1.1 to I.a.1.558 in that $R^1$ is $CF_3$ and $R^2$ and $R^3$ are chlorine.

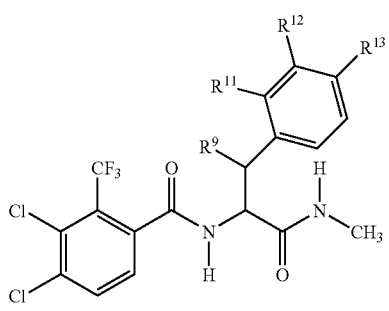

I.a.24

Most preference is also given to the compounds of the formula I.a.25, in particular to the compounds of the formulae I.a.25.1 to I.a.25.558 which differ from the corresponding compounds of the formulae I.a.1.1 to I.a.1.558 in that $R^1$ and $R^2$ are $CF_3$.

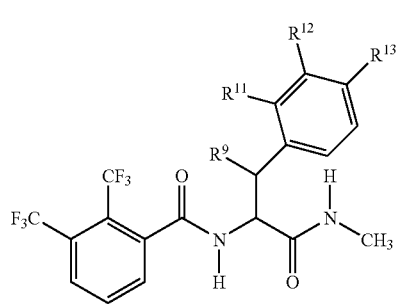

I.a.25

Most preference is also given to the compounds of the formula I.a.26, in particular to the compounds of the formulae I.a.26.1 to I.a.26.558 which differ from the corresponding compounds of the formulae I.a.1.1 to I.a.1.558 in that $R^1$ and $R^2$ are $CF_3$ and $R^3$ is fluorine.

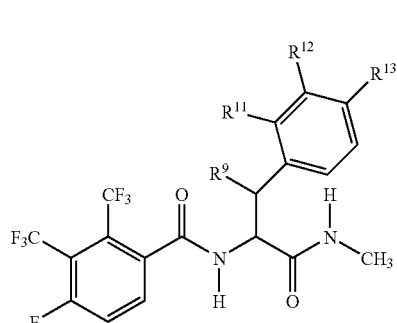

I.a.26

Most preference is also given to the compounds of the formula I.a.27, in particular to the compounds of the formulae I.a.27.1 to I.a.27.558 which differ from the corresponding compounds of the formulae I.a.1.1 to I.a.1.558 in that $R^1$ and $R^2$ are $CF_3$ and $R^3$ is chlorine.

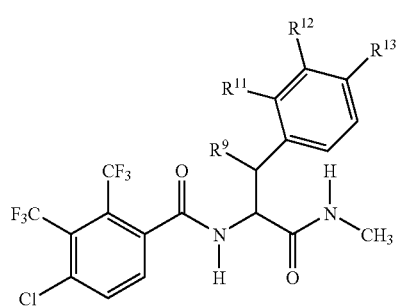

I.a.27

Most preference is also given to the compounds of the formula I.a.28, in particular to the compounds of the formulae I.a.28.1 to I.a.28.558 which differ from the corresponding compounds of the formulae I.a.1.1 to I.a.1.558 in that $R^1$ is $CF_3$ and $R^4$ is fluorine.

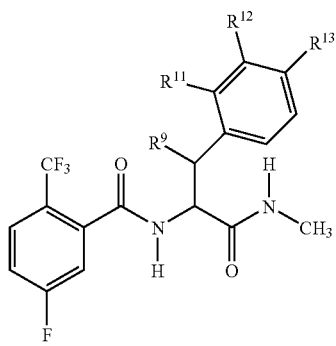

I.a.28

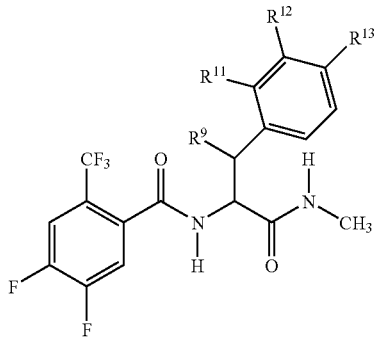

I.a.29

Most preference is also given to the compounds of the formula I.a.29, in particular to the compounds of the formulae I.a.29.1 to I.a.29.558 which differ from the corresponding compounds of the formulae I.a.1.1 to I.a.1.558 in that $R^1$ is $CF_3$ and $R^3$ and $R^4$ are fluorine.

The benzoyl-substituted phenylalanineamides of the formula I can be obtained by different routes, for example by the following processes:

Process A

A phenylalanine of the formula V is initially reacted with benzoic acids or benzoic acid derivatives of the formula IV to give the corresponding benzoyl derivative of the formula III which is then reacted with an amine of the formula II to give the desired benzoyl-substituted phenylalanineamide of the formula I:

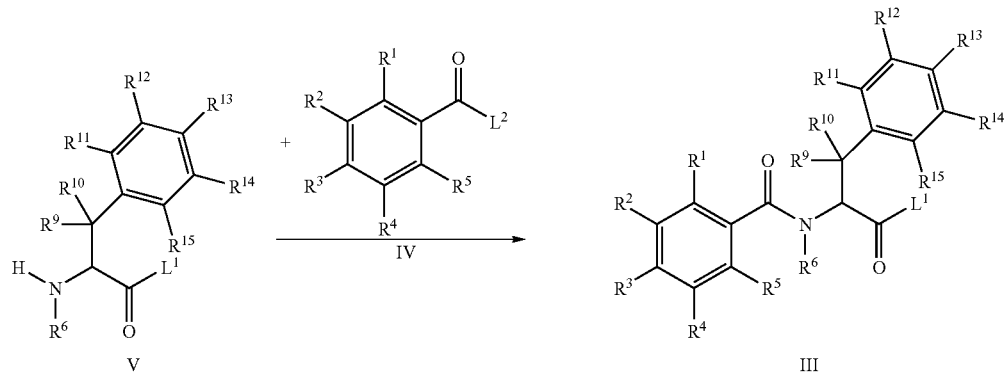

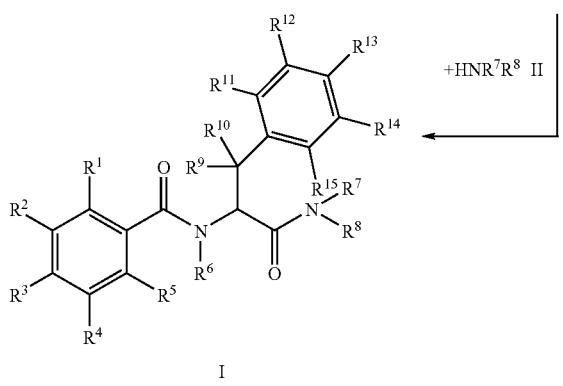

$L^1$ is a nucleophilically displaceable leaving group, for example hydroxyl or $C_1$-$C_6$-alkoxy.

$L^2$ is a nucleophilically displaceable leaving group, for example hydroxyl, halogen, $C_1$-$C_6$-alkylcarbonyl, $C_1$-$C_6$-alkoxycarbonyl, $C_1$-$C_4$-alkylsulfonyl, phosphoryl or isoureyl.

The reaction of the phenylalanines of the formula V with benzoic acids or benzoic acid derivatives of the formula IV in which $L^2$ is hydroxyl to give benzoyl derivatives of the formula III is carried out in the presence of an activating agent and a base, usually at temperatures of from 0° C. to the boiling point of the reaction mixture, preferably from 0° C. to 110° C., particularly preferably at room temperature, in an inert organic solvent [cf. Bergmann, E. D. et al., J. Chem. Soc. (1951), 2673; Zhdankin, V. V. et al., Tetrahedron Lett. 41 (28) (2000), 5299-5302; Martin, S. F. et al., Tetrahedron Lett. 39 (12) (1998), 1517-1520; Jursic, B. S. et al., Synth. Commun. 31 (4) (2001), 555-564; Albrecht, M. et al., Synthesis (3) (2001), 468-472; Yadav, L. D. S. et al., Indian J. Chem. B. 41(3) (2002), 593-595; Clark, J. E. et al., Synthesis (10) (1991), 891-894].

Suitable activating agents are condensing agents, such as, for example, polystyrene-bound dicyclohexylcarbodiimide, diisopropylcarbodiimide, carbonyldiimidazole, chloroformates, such as methyl chloroformate, ethyl chloroformate, isopropyl chloroformate, isobutyl chloroformate, sec-butyl chloroformate or allyl chloroformate, pivaloyl chloride, polyphosphoric acid, propanephosphonic anhydride, bis(2-oxo-3-oxazolidinyl)phosphoryl chloride (BOPCI) or sulfonyl chlorides, such as methanesulfonyl chloride, toluenesulfonyl chloride or benzenesulfonyl chloride.

Suitable solvents are aliphatic hydrocarbons, such as pentane, hexane, cyclohexane and mixtures of $C_5$-$C_8$-alkanes, aromatic hydrocarbons, such as benzene, toluene, o-, m- and p-xylene, halogenated hydrocarbons, such as methylene chloride, chloroform and chlorobenzene, ethers, such as diethyl ether, diisopropyl ether, tert-butyl methyl ether, dioxane, anisole and tetrahydrofuran (THF), nitriles, such as acetonitrile and propionitrile, ketones, such as acetone, methyl ethyl ketone, diethyl ketone and tert-butyl methyl ketone, and also dimethyl sulfoxide, dimethylformamide (DMF), dimethylacetamide (DMA) and N-methylpyrrolidone (NMP), or else water; particular preference is given to methylene chloride, THF and water.

It is also possible to use mixtures of the solvents mentioned.

Suitable bases are, in general, inorganic compounds, such as alkali metal and alkaline earth metal hydroxides, such as lithium hydroxide, sodium hydroxide, potassium hydroxide and calcium hydroxide, alkali metal and alkaline earth metal oxides, such as lithium oxide, sodium oxide, calcium oxide and magnesium oxide, alkali metal and alkaline earth metal hydrides, such as lithium hydride, sodium hydride, potassium hydride and calcium hydride, alkali metal and alkaline earth metal carbonates, such as lithium carbonate, potassium carbonate and calcium carbonate, and also alkali metal bicarbonates, such as sodium bicarbonate, moreover organic bases, for example tertiary amines, such as trimethylamine, triethylamine, diisopropylethylamine, N-methylmorpholine and N-methylpiperidine, pyridine, substituted pyridines, such as collidine, lutidine and 4-dimethylaminopyridine, and also bicyclic amines. Particular preference is given to sodium hydroxide, triethylamine and pyridine.

The bases are generally employed in equimolar amounts. However, they can also be used in excess or, if appropriate, as solvent.

The starting materials are generally reacted with one another in equimolar amounts. It may be advantageous to use an excess of IV, based on V.

The reaction mixtures are worked up in a customary manner, for example by mixing with water, separating the phases and, if appropriate, chromatographic purification of the crude products. Some of the intermediates and end products are obtained in the form of viscous oils which can be purified or freed from volatile components under reduced pressure and at moderately elevated temperature. If the intermediates and end products are obtained as solids, purification can also be carried out by recrystallization or digestion.

The reaction of the phenylalanines of the formula V with benzoic acids or benzoic acid derivatives of the formula IV in which $L^2$ is halogen or $C_1$-$C_6$-alkoxy to give benzoyl derivatives of the formula III is carried out in the presence of a base, usually at temperatures of from 0° C. to the boiling point of the reaction mixture, preferably from 0° C. to 100° C., particularly preferably at room temperature, in an inert organic solvent [cf. Bergmann, E. D. et al., J. Chem. Soc. (1951), 2673; Zhdankin, V. V. et al., Tetrahedron Lett. 41 (28) (2000), 5299-5302; Martin, S. F. et al., Tetrahedron Lett. 39 (12) (1998), 1517-1520; Jursic, B. S. et al., Synth. Commun. 31 (4) (2001), 555-564; Albrecht, M. et al., Synthesis (3) (2001), 468472; Yadav, L. D. S. et al., Indian J. Chem. B. 41(3) (2002), 593-595; Clark, J. E. et al., Synthesis (10) (1991), 891-894].

Suitable solvents are aliphatic hydrocarbons, such as pentane, hexane, cyclohexane and mixtures of $C_5$-$C_8$-alkanes, aromatic hydrocarbons, such as benzene, toluene, o-, m- and p-xylene, halogenated hydrocarbons, such as methylene chloride, chloroform and chlorobenzene, ethers, such as diethyl ether, diisopropyl ether, tert-butyl methyl ether, dioxane, anisole and tetrahydrofuran (THF), nitriles, such as acetonitrile and propionitrile, ketones, such as acetone, methyl ethyl ketone, diethyl ketone and tert-butyl methyl ketone, and also dimethyl sulfoxide, dimethylformamide (DMF), dimethylacetamide (DMA) and N-methylpyrrolidone (NMP), or else water; particular preference is given to methylene chloride, THF and water.

It is also possible to use mixtures of the solvents mentioned.

Suitable bases are, in general, inorganic compounds, such as alkali metal and alkaline earth metal hydroxides, such as lithium hydroxide, sodium hydroxide, potassium hydroxide and calcium hydroxide, alkali metal and alkaline earth metal oxides, such as lithium oxide, sodium oxide, calcium oxide and magnesium oxide, alkali metal and alkaline earth metal hydrides, such as lithium hydride, sodium hydride, potassium hydride and calcium hydride, alkali metal and alkaline earth metal carbonates, such as lithium carbonate, potassium carbonate and calcium carbonate, and also alkali metal bicarbonates, such as sodium bicarbonate, moreover organic bases, for example tertiary amines, such as trimethylamine, triethylamine, diisopropylethylamine, N-methylmorpholine and N-methylpiperidine, pyridine, substituted pyridines, such as collidine, lutidine and 4-dimethylaminopyridine, and also bicyclic amines. Particular preference is given to sodium hydroxide, triethylamine and pyridine.

The bases are generally employed in equimolar amounts. However, they can also be used in excess or, if appropriate, as solvent.

The starting materials are generally reacted with one another in equimolar amounts. It may be advantageous to use an excess of IV, based on V.

Work-up and isolation of the products can be carried out in a manner known per se.

It is, of course, also possible to initially react, in an analogous manner, the phenylalanines of the formula V with amines of the formula II to give the corresponding amides which are then reacted with benzoic acids/benzoic acid derivatives of the formula IV to give the desired benzoyl-substituted phenylalanineamides of the formula I.

The phenylalanines, required for preparing the benzoyl derivatives of the formula III, of the formula V where $L^1$=hydroxyl are, also in enantiomerically and diastereomerically pure form, known from the literature or can be prepared in accordance with the literature cited:

$R^9$=$OR^{16}$:
by condensation of glycine enolate equivalents with benzaldehydes
(Hvidt, T. et al., Tetrahedron Lett. 27 (33) (1986), 3807-3810; Saeed, A. et al., Tetrahedron 48 (12) (1992), 2507-2514; Kikuchi, J. et al., Chem. Lett. (3) (1993), 553-556; Soloshonok, V. A. et al., Tetrahedron Lett. 35 (17) (1994), 2713-2716; Soloshonok, V. A. et al., Tetrahedron 52 (1) (1996), 245-254; Rozenberg, V. et al., Angew. Chem. 106 (1) (1994), 106-108; U.S. Pat. No. 4,605,759; Alker, D. et al., Tetrahedron 54 (22) (1998), 6089-6098; Shengde, W. et al., Synth. Commun. 16 (12) (1986), 1479; JP 2001046076; Herbert, R. B. et al., Can. J. Chem. 72 (1) (1994), 114-117);
by cleaving 2-N-phthaloyl-3-hydroxyphenylalanines
(Hutton, C. A., Org. Lett. 1 (2) (1999), 295-297);
by oxidative aminohydroxylation and subsequent deprotection of cinnamic acid derivatives
(Kim, I. H. et al., Tetrahedron Lett. 42 (48) (2001), 8401-8403);
by cleaving substituted oxazolidines
(Wu, S. D. et al., Synthetic Commun. 16 (12) (1986), 1479-1484);
by cleaving substituted oxazolines
(Soloshonok, V. A. et al., Tetrahedron 52 (1) (1996), 245-254; Lown, J. W. et al., Can. J. Chem. 51 (1973), 856);
by cleaving substituted 2-oxazolidinones
(Jung, M. E. et al., Tetrahedron Lett. 30 (48) (1989), 6637-6640);
by cleaving substituted 5-oxazolidinones
(Blaser, D. et al., Liebigs Ann. Chem. (10) (1991), 1067-1078);
by hydrolysis of phenylserinenitrile derivatives
(Iriuchijima, S. et al., J. Am. Chem. Soc. 96 (1974), 4280);
by cleaving substituted imidazolin-4-ones
(Davis, C. et al., J. Chem. Soc. 3479 (1951));
$R^9$=$SR^{17}$:
by cleaving 2-acylamino-3-thioalkylphenylalanine derivatives
(Villeneuve, G. et al., J. Chem. Soc. Perkin Trans 1 (16) (1993), 1897-1904)
by ring opening of thiazolidinethiones
(Cook, A. H. et al., J. Chem. Soc. (1948) 1337);
$R^9$=$NR^{18}R^{19}$:
by ring opening of substituted imidazolinones
(Kavrakova, I. K. et al., Org. Prep. Proced. Int. 28 (3) (1996), 333-338);
by ring opening of substituted imidazolines
(Meyer R., Liebigs Ann. Chem., 1183 (1977); Hayashi, T. et al., Tetrahedron Lett. 37 (28) (1996), 4969-4972; Lin, Y. R. et al., J. Org. Chem. 62 (6) (1997), 1799-1803; Zhou, X. T. et al., Tetrahedron Assym. 10 (5) (1999), 855-862);
by reducing 2-azido-3-aminophenylalanine derivatives
(Moyna, G. et al., Synthetic Commun. 27 (9) (1997), 1561-1567);
by hydrogenation of substituted imidazolidines
(Alker, D. et al., Tetrahedron Lett. 39 (5-6) (1998), 475-478).

The phenylalanines, required for preparing the benzoyl derivatives of the formula III, of the formula V where $L^1$=$C_1$-$C_6$-alkoxy are, also in enantiomerically and diastereomerically pure form, known from the literature or can be prepared in accordance with the literature cited:

$R^9$=$OR^{16}$:
by condensation of glycine enolate equivalents with aldehydes:
(Nicolaou, K. C. et al., J. Am. Chem. Soc. 124 (35) (2002), 10451-10455; Carrara, G. et al., Gazz. Chim. Ital. 82 (1952), 325; Fuganti, C. et al., J. Org. Chem. 51 (7) (1986), 1126-1128; Boger, D. L. et al., J. Org. Chem. 62 (14) (1997), 4721-4736; Honig, H. et al., Tetrahedron (46) (1990), 3841; Kanemasa, S. et al., Tetrahedron Lett. 34 (4) (1993), 677-680; U.S. Pat. No. 4,873,359);
by cleaving dihydropyrazines
(Li, Y. Q. et al., Tetrahedron Lett. 40 (51) (1999), 9097-9100; Beulshausen, T. et al., Liebigs Ann. Chem. (11) (1991), 1207-1209);
by reducing N-aminophenylserine derivatives
(Poupardin, O. et al., Tetrahedron Lett. 42 (8) (2001), 1523-1526);
by cleaving N-carbamoylphenylserine derivatives
(Park, H. et al., J. Org. Chem. 66 (21) (2001), 7223-7226; U.S. Pat. No. 6,057,473; Kim, I. H. et al., Tetrahedron Lett. 42 (48) (2001), 8401-8403; Nicolaou, K. C. et al., Angew. Chem. Int. Edit. 37 (19) (1998), 2714-2716);
by cleaving substituted oxazolidines
(Zhou, C. Y. et al., Synthetic Commun. 17 (11) (1987), 1377-1382);
by reducing 2-azido-3-hydroxyphenylpropionic acid derivatives
(Corey, E. J. et al., Tetrahedron Lett. 32 (25) (1991), 2857-2860);
by ring opening of aziridines with oxygen nucleophiles
(Davis, F. A. et al., J. Org. Chem. 59 (12) (1994), 3243-3245);
by cleaving substituted 2-oxazolidinones
(Jung, M. E. et al., Synlett (1995) 563-564);
by reducing 2-hydroxyimino-3-ketophenylpropionic acid derivatives
(Inoue, H. et al., Chem. Phar. Bull. 41 (9) (1993), 1521-1523; Chang, Y.-T. et al., J. Am. Chem. Soc. 75 (1953), 89; U.S. Pat. No. 4,810,817);
by hydrolysis of phenylserineimino derivatives (Solladiecavallo, A. et al., Gazz. Chim. Ital. 126 (3) (1996), 173-178; Solladiecavallo, A. et al., Tetrahedron Lett. 39 (15) (1998), 2191-2194);
by cleaving N-acylphenylserine derivatives
(Girard, A. et al., Tetrahedron Lett. 37 (44) (1996), 7967-7970);
by reducing 2-hydroxyimino-3-hydroxyphenylpropionic acid derivatives (Boukhris, S. et al., Tetrahedron Lett. 40 (9) (1999), 1669-1672);
by cleaving N-benzylphenylserine derivatives
(Caddick, S., Tetrahedron, 57 (30) (2001), 6615-6626);
by reducing 2-diazo-3-ketophenylpropionic acid derivatives
(Looker, et al., J. Org. Chem. 22 (1957), 1233);
by cleaving substituted imidazolidinones
(Davis, A. C. et al., J. Chem. Soc. 3479 (1951));
$R^9$=$SR^{17}$:
by ring opening of substituted thiazolidines
(Nagai, U. et al., Heterocycles 28 (2) (1989), 589-592);

by ring opening of substituted aziridines with thiols
(Legters, J. et al., Recl. Trav. Chim. Pays-Bas 111 (1) (1992), 16-21);
by reducing 3-ketophenylalanine derivatives (U.S. Pat. No. 4,810,817);
$R^9$=$NR^{18}R^{19}$:
by reducing substituted 2-azido-3-aminophenylalanine derivatives
(Lee S. H., Tetrahedron 57(11) (2001), 2139-2145);
by ring opening of substituted imidazolines
(Zhou, X. T. et al., Tetrahedron Asymmetr. 10 (5) (1999), 855-862; Hayashi, T. et al., Tetrahedron Lett. 37 (28) (1996), 4969-4972).

The benzoic acids/benzoic acid derivatives of the formula IV required for preparing the benzoyl derivatives of the formula III are commercially available or can be prepared analogously to procedures known from the literature via a Grignard reaction from the corresponding halide [for example A. Mannschuk et al., Angew. Chem. 100 (1988), 299].

The reaction of the benzoyl derivatives of the formula III where $L^1$=hydroxyl or salts thereof with an amine of the formula II to give the desired benzoyl-substituted phenylalanineamides of the formula I is carried out in the presence of an activating agent and, if appropriate, in the presence of a base, usually at temperatures of from 0° C. to the boiling point of the reaction mixture, preferably from 0° C. to 100° C., particularly preferably at room temperature, in an inert organic solvent [cf. Perich, J. W., Johns, R. B., J. Org. Chem. 53 (17) (1988), 4103-4105; Somlai, C. et al., Synthesis (3) (1992), 285-287; Gupta, A. et al., J. Chem. Soc. Perkin Trans. 2 (1990), 1911; Guan et al., J. Comb. Chem. 2 (2000), 297].

Suitable activating agents are condensing agents, such as, for example, polystyrene-bound dicyclohexylcarbodiimide, diisopropylcarbodiimide, carbonyldiimidazole, chloroformates, such as methyl chloroformate, ethyl chloroformate, isopropyl chloroformate, isobutyl chloroformate, sec-butyl chloroformate or allyl chloroformate, pivaloyl chloride, polyphosphoric acid, propanephosphonic anhydride, bis(2-oxo-3-oxazolidinyl)phosphoryl chloride (BOPCl) or sulfonyl chlorides, such as methanesulfonyl chloride, toluenesulfonyl chloride or benzenesulfonyl chloride.

Suitable solvents are aliphatic hydrocarbons, such as pentane, hexane, cyclohexane and mixtures of $C_5$-$C_8$-alkanes, aromatic hydrocarbons, such as benzene, toluene, o-, m- and p-xylene, halogenated hydrocarbons, such as methylene chloride, chloroform and chlorobenzene, ethers, such as diethyl ether, diisopropyl ether, tert-butyl methyl ether, dioxane, anisole and tetrahydrofuran (THF), nitriles, such as acetonitrile and propionitrile, ketones, such as acetone, methyl ethyl ketone, diethyl ketone and tert-butyl methyl ketone, alcohols, such as methanol, ethanol, n-propanol, isopropanol, n-butanol and tert-butanol, and also dimethyl sulfoxide, dimethylformamide (DMF), dimethylacetamide (DMA) and N-methylpyrrolidone (NMP), or else water; particular preference is given to methylene chloride, THF, methanol, ethanol and water.

It is also possible to use mixtures of the solvents mentioned.

Suitable bases are, in general, inorganic compounds, such as alkali metal and alkaline earth metal hydroxides, such as lithium hydroxide, sodium hydroxide, potassium hydroxide and calcium hydroxide, alkali metal and alkaline earth metal oxides, such as lithium oxide, sodium oxide, calcium oxide and magnesium oxide, alkali metal and alkaline earth metal hydrides, such as lithium hydride, sodium hydride, potassium hydride and calcium hydride, alkali metal and alkaline earth metal carbonates, such as lithium carbonate, potassium carbonate and calcium carbonate, and also alkali metal bicarbonates, such as sodium bicarbonate, moreover organic bases, for example tertiary amines, such as trimethylamine, triethylamine, diisopropylethylamine, N-methylmorpholine and N-methylpiperidine, pyridine, substituted pyridines, such as collidine, lutidine and 4-dimethylaminopyridine, and also bicyclic amines. Particular preference is given to sodium hydroxide, triethylamine, ethyidiisopropylamine, N-methylmorpholine and pyridine.

The bases are generally employed in catalytic amounts; however, they can also be employed in equimolar amounts, in excess or, if appropriate, as solvent.

The starting materials are generally reacted with one another in equimolar amounts. It may be advantageous to use an excess of II, based on III.

Work-up and isolation of the products can be carried out in a manner known per se.

The reaction of the benzoyl derivatives of the formula III where $L^1$=$C_1$-$C_6$-alkoxy with an amine of the formula II to give the desired benzoyl-substituted phenylalanineamides of the formula I is usually carried out at temperatures of from 0° C. to the boiling point of the reaction mixture, preferably from 0° C. to 100° C., particularly preferably at room temperature, in an inert organic solvent, if appropriate in the presence of a base [cf. Kawahata, N. H. et al., Tetrahedron Lett. 43 (40) (2002), 7221-7223; Takahashi, K. et al., J. Org. Chem. 50 (18) (1985), 3414-3415; Lee, Y. et al., J. Am. Chem. Soc. 121 (36) (1999), 8407-8408].

Suitable solvents are aliphatic hydrocarbons, such as pentane, hexane, cyclohexane and mixtures of $C_5$-$C_8$-alkanes, aromatic hydrocarbons, such as benzene, toluene, o-, m- and p-xylene, halogenated hydrocarbons, such as methylene chloride, chloroform and chlorobenzene, ethers, such as diethyl ether, diisopropyl ether, tert-butyl methyl ether, dioxane, anisole and tetrahydrofuran (THF), nitriles, such as acetonitrile and propionitrile, ketones, such as acetone, methyl ethyl ketone, diethyl ketone and tert-butyl methyl ketone, alcohols, such as methanol, ethanol, n-propanol, isopropanol, n-butanol and tert-butanol, and also dimethyl sulfoxide, dimethylformamide (DMF), dimethylacetamide (DMA) and N-methylpyrrolidone (NMP) or else water; particular preference is given to methylene chloride, THF, methanol, ethanol and water.

It is also possible to use mixtures of the solvents mentioned.

The reaction can, if appropriate, be carried out in the presence of a base. Suitable bases are, in general, inorganic compounds, such as alkali metal and alkaline earth metal hydroxides, such as lithium hydroxide, sodium hydroxide, potassium hydroxide and calcium hydroxide, alkali metal and alkaline earth metal oxides, such as lithium oxide, sodium oxide, calcium oxide and magnesium oxide, alkali metal and alkaline earth metal hydrides, such as lithium hydride, sodium hydride, potassium hydride and calcium hydride, alkali metal and alkaline earth metal carbonates, such as lithium carbonate, potassium carbonate and calcium carbonate, and also alkali metal bicarbonates, such as sodium bicarbonate, moreover organic bases, for example tertiary amines, such as trimethylamine, triethylamine, diisopropylethylamine, N-methylmorpholine, and N-methylpiperidine, pyridine, substituted pyridines, such as collidine, lutidine and 4-dimethylaminopyridine, and also bicyclic amines. Particular preference is given to sodium hydroxide, triethylamine, ethyldiisopropylamine, N-methylmorpholine and pyridine.

The bases are generally employed in catalytic amounts; however, they can also be employed in equimolar amounts, in excess or, if appropriate, as solvent.

The starting materials are generally reacted with one another in equimolar amounts. It may be advantageous to employ an excess of II, based on III.

Work-up and isolation of the products can be carried out in a manner known per se.

The amines of the formula II required for preparing the benzoyl-substituted phenylalanineamides of the formula I are commercially available.

Process B

Benzoyl derivatives of the formula III where $R^9$=hydroxyl can also be obtained by condensing acylated glycine derivatives of the formula VIII where the acyl group is a cleavable protective group, such as benzyloxycarbonyl (cf. VIIIa where Σ=benzyl) or tert-butyloxycarbonyl (cf. VIIIa where Σ=tert-butyl) with heterocyclylcarbonyl compounds VII to give the corresponding aldol products VI. The protective group is then removed, and the resulting phenylalanines of the formula V where $R^9$=hydroxyl are acylated with benzoic acids/benzoic acid derivatives of the formula IV.

Analogously, it is also possible to react an acylated glycine derivative of the formula VIII where the acyl group is a substituted benzoyl radical (cf. VIIIb) under action of bases with a heterocyclylcarbonyl compound VII to give the benzoyl derivative III where $R^9$=hydroxyl:

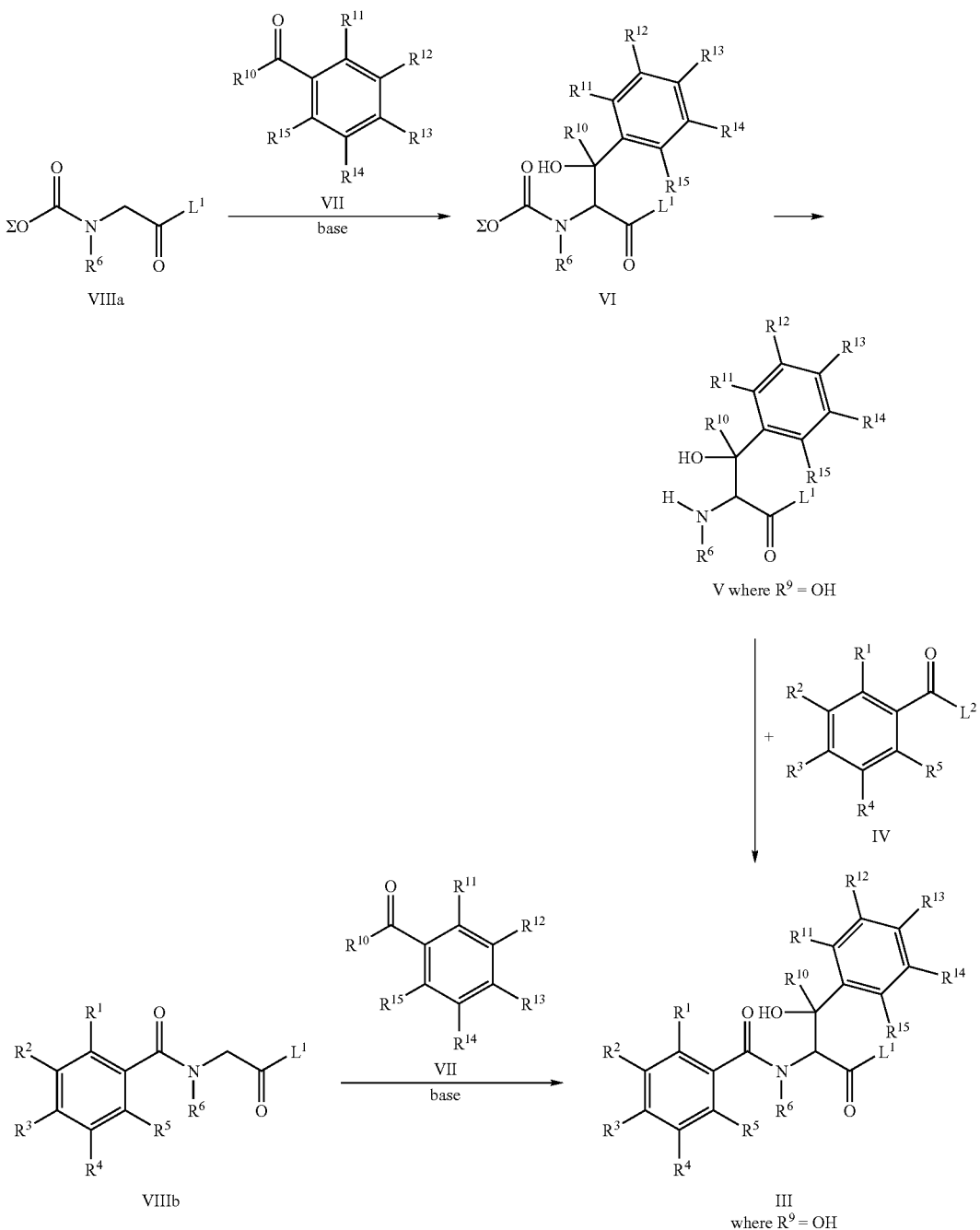

$L^1$ is a nucleophilically displaceable leaving group, for example hydroxyl or $C_1$-$C_6$-alkoxy.

$L^2$ is a nucleophilically displaceable leaving group, for example hydroxyl, halogen, $C_1$-$C_6$-alkylcarbonyl, $C_1$-$C_6$-alkoxycarbonyl, $C_1$-$C_4$-alkylsulfonyl, phosphoryl or isoureyl.

The reaction of the glycine derivatives VIII with heterocyclyl compounds VII to give the corresponding aldol product VI or benzoyl derivative III where $R^9$=hydroxyl is usually carried out at temperatures of from −100° C. to the boiling point of the reaction mixture, preferably from −80° C. to 20° C., particularly preferably from −80° C. to −20° C., in an inert organic solvent in the presence of a base [cf. J.-F. Rousseau et al., J. Org. Chem. 63 (1998), 2731-2737].

Suitable solvents are aliphatic hydrocarbons, such as pentane, hexane, cyclohexane and mixtures of $C_5$-$C_8$-alkanes, aromatic hydrocarbons, such as toluene, o-, m- and p-xylene, ethers, such as diethyl ether, diisopropyl ether, tert-butyl methyl ether, dioxane, anisole and tetrahydrofuran, and also dimethyl sulfoxide, dimethylformamide and dimethylacetamide, particularly preferably diethyl ether, dioxane and tetrahydrofuran.

It is also possible to use mixtures of the solvents mentioned.

Suitable bases are, in general, inorganic compounds, such as alkali metal and alkaline earth metal anhydrides, such as lithium hydride, sodium hydride, potassium hydride and calcium hydride, alkali metal azides, such as lithium hexamethyidisilazide, organometallic compounds, in particular alkali metal alkyls, such as methyllithium, butyllithium and phenyllithium, and also alkali metal and alkaline earth metal alkoxides, such as sodium methoxide, sodium ethoxide, potassium ethoxide, potassium tert-butoxide, potassium tert-pentoxide and dimethoxymagnesium, moreover organic bases, for example tertiary amines, such as trimethylamine, triethylamine, diisopropylethylamine and N-methylpiperidine, pyridine, substituted pyridines, such as collidine, lutidine and 4-dimethylaminpyridine, and also bicyclic amines. Particular preference is given to sodium hydride, lithium hexamethyldisilazide and lithium diisopropylamide.

The bases are generally employed in equimolar amounts; however, they can also be employed in catalytic amounts, in excess or, if appropriate, as solvents.

The starting materials are generally reacted with one another in equimolar amounts. It may be advantageous to employ an excess of base and/or the heterocyclylcarbonyl compounds VII, based on the glycine derivatives VIII.

Work-up and isolation of the products can be carried out in a manner known per se. The glycine derivatives of the formula VIII required for preparing the compounds I are commercially available, known from the literature [for example H. Pessoa-Mahana et al., Synth. Comm. 32 (2002), 1437] or can be prepared in accordance with the literature cited.

The removal of the protective group to give phenylalanines of the formula V where $R^9$=hydroxyl is carried out by methods known from the literature (cf. J.-F. Rousseau et al., J. Org. Chem. 63 (1998), 2731-2737; J. M. Andres, Tetrahedron 56 (2000), 1523]; in the case of Σ=benzyl by hydrogenolysis, preferably using hydrogen and Pd/C in methanol, in the case of Σ=tert-butyl by using an acid, preferably hydrochloric acid in dioxane.

The reaction of the phenylalanines V where $R^9$=hydroxyl with benzoic acids/benzoic acid derivatives IV to give benzoyl derivatives III where $R^9$=hydroxyl is usually carried out analogously to the reaction, mentioned in process A, of the phenylalanines of the formula V with benzoic acids/benzoic acid derivatives of the formula IV to give benzoyl derivatives III.

The benzoyl derivatives of the formula III where $R^9$=hydroxyl can then be reacted analogously to process A with amines of the formula II to give the desired benzoyl-substituted phenylalanineamides of the formula I where $R^9$=hydroxyl, which can then be derivatized with compounds of the formula IX to give benzoyl-substituted phenylalanineamides of the formula I where $R^9$=$OR^{16}$ [cf., for example, Yokokawa, F. et al., Tetrahedron Lett. 42 (34) (2001), 5903-5908; Arrault, A. et al., Tetrahedron Lett. 43 (22) (2002), 4041-4044].

It is also possible to initially derivatize the benzoyl derivatives of the formula III where $R^9$=hydroxyl with compounds of the formula IX to give further benzoyl derivatives of the formula III [cf., for example, Troast, D. et al., Org. Lett. 4 (6) (2002), 991-994: Ewing W. et al., Tetrahedron Lett. 30 (29) (1989), 3757-3760; Paulsen, H. et al., Liebigs Ann. Chem. (1987), 565], followed by reaction, analogously to process A, with amines of the formula II to give the desired benzoyl-substituted phenylalanineamides of the formula I where $R^9$=$OR^{16}$:

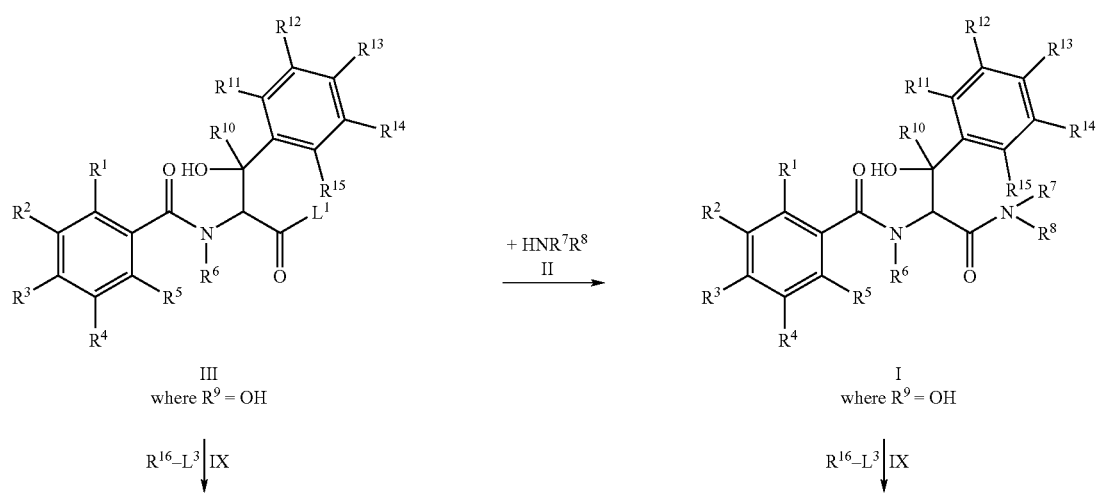

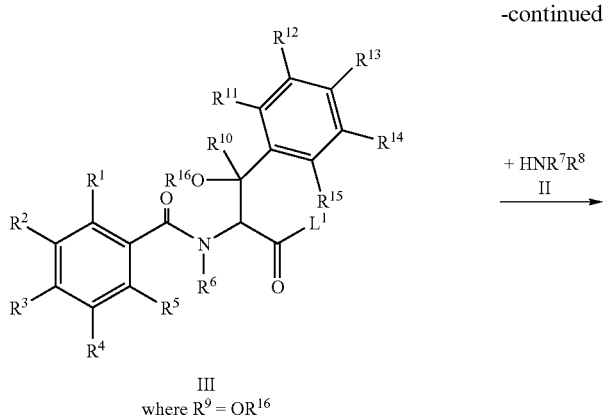

III
where $R^9 = OR^{16}$

+ $HNR^7R^8$
II

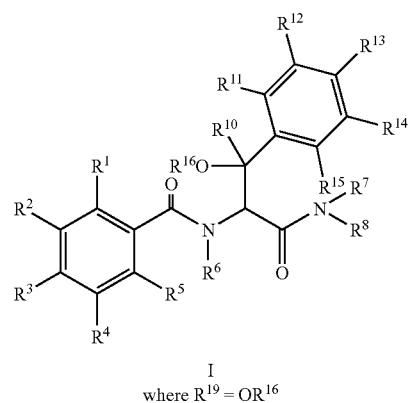

I
where $R^{19} = OR^{16}$ $L^1$ is a nucleophilically displaceable leaving group, for example hydroxyl or $C_1$-$C_6$-alkoxy.

$L^3$ is a nucleophilically displaceable leaving group, for example halogen, hydroxyl or $C_1$-$C_6$-alkoxy.

The reaction of the benzoyl derivatives of the formula III where $R^9$=hydroxyl or $OR^{16}$ with amines of the formula II to give benzoyl-substituted phenylalanineamides of the formula I where $R^9$=hydroxyl or $OR^{16}$ is usually carried out analogously to the reaction, outlined in process A, of the benzoyl derivatives of the formula III with amines of the formula II.

The reaction of the benzoyl derivatives of the formula III where $R^9$=hydroxyl or of the benzoyl-substituted phenylalanineamides of the formula I where $R^9$=hydroxyl with compounds of the formula IX to give benzoyl derivatives of the formula III where $R^9$=$OR^{16}$ and benzoyl-substituted phenylalanineamides of the formula I where $R^9$=$OR^{16}$, respectively, is usually carried out at temperatures of from 0° C. to 100° C., preferably 10° C. to 50° C., in an inert organic solvent in the presence of a base [cf., for example, Troast, D. et al., Org. Lett. 4 (6), (2002), 991-994; Ewing W. et al., Tetrahedron Lett. 30 (29) (1989), 3757-3760; Paulsen, H. et al., Liebigs Ann. Chem. (1987), 565].

Suitable solvents are aliphatic hydrocarbons, such as pentane, hexane, cyclohexane and mixtures of $C_5$-$C_8$-alkanes, aromatic hydrocarbons, such as toluene, o-, m- and p-xylene, halogenated hydrocarbons, such as methylene chloride, chloroform and chlorobenzene, ethers, such as diethyl ether, diisopropyl ether, tert-butyl methyl ether, dioxane, anisole and tetrahydrofuran, nitriles, such as acetonitrile and propionitrile, ketones, such as acetone, methyl ethyl ketone, diethyl ketone and tert-butyl methyl ketone, alcohols, such as methanol, ethanol, n-propanol, isopropanol, n-butanol and tert-butanol, and also dimethyl sulfoxide, dimethylformamide and dimethylacetamide, particularly preferably dichloromethane, tert-butyl methyl ether, dioxane and tetrahydrofuran.

It is also possible to use mixtures of the solvents mentioned.

Suitable bases are, in general, inorganic compounds, such as alkali metal and alkaline earth metal hydroxides, such as lithium hydroxide, sodium hydroxide, potassium hydroxide and calcium hydroxide, alkali metal and alkaline earth metal oxides, such as lithium oxide, sodium oxide, calcium oxide and magnesium oxide, alkali metal and alkaline earth metal hydrides, such as lithium hydride, sodium hydride, potassium hydride and calcium hydride, alkali metal amides, such as lithium amide, sodium amide and potassium amide, alkali metal and alkaline earth metal carbonates, such as lithium carbonate, potassium carbonate and calcium carbonate, and also alkali metal bicarbonates, such as sodium bicarbonate, organometallic compounds, in particular alkali metal alkyls, such as methyllithium, butyllithium and phenyllithium, alkylmagnesium halides, such as methylmagnesium chloride, and also alkali metal and alkaline earth metal alkoxides, such as sodium methoxide, sodium ethoxide, potassium ethoxide, potassium tert-butoxide, potassium tert-pentoxide and dimethoxymagnesium, moreover organic bases, for example tertiary amines, such as trimethylamine, triethylamine, diisopropylethylamine and N-methylpiperidine, pyridine, substituted pyridines, such as collidine, lutidine and 4-dimethylaminopyridine, and also bicyclic amines. Particular preference is given to sodium hydroxide, sodium hydride and triethylamine.

The bases are generally employed in equimolar amounts; however, they can also be used in catalytic amounts, in excess or, if appropriate, as solvent.

The starting materials are generally reacted with one another in equimolar amounts. It may be advantageous to employ an excess of base and/or IX, based on III or I.

Work-up and isolation of the products can be carried out in a manner known per se.

The required compounds of the formula VIII are commercially available.

Process C

Benzoyl derivatives of the formula III where $R^9$=hydroxyl can also be obtained by initially acylating aminomalonyl compounds of the formula XI with benzoic acids/benzoic acid derivatives of the formula IV to give the corresponding N-acylaminomalonyl compounds of the formula X, followed by condensation with a heterocyclylcarbonyl compound of the formula VII with decarboxylation:

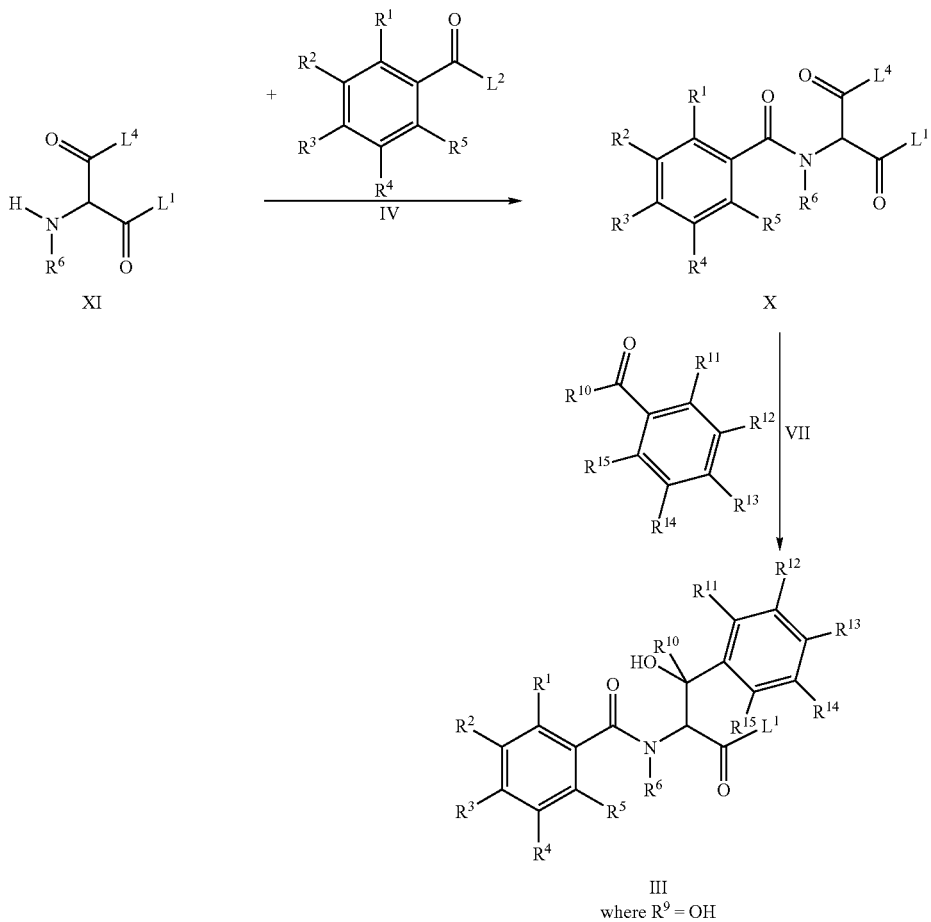

$L^1$ is a nucleophilically displaceable leaving group, for example hydroxyl or $C_1$-$C_6$-alkoxy.

$L^2$ is a nucleophilically displaceable leaving group, for example hydroxyl, halogen, $C_1$-$C_6$-alkylcarbonyl, $C_1$-$C_6$-alkoxycarbonyl, $C_1$-$C_6$-alkylsulfonyl, phosphoryl or isoureyl.

$L^4$ is a nucleophilically displaceable leaving group, for example hydroxyl or $C_1$-$C_6$-alkoxy.

The acylation of the aminomalonyl compounds of the formula XI with benzoic acid/benzoic acid derivatives of the formula IV to give the corresponding N-acylaminomalonyl compounds of the formula X is usually carried out analogously to the reaction, mentioned in process A, of the phenylalanines of the formula V with benzoic acids/benzoic acid derivatives of the formula IV to give the corresponding benzoyl derivatives of the formula III.

The reaction of the N-acylaminomalonyl compounds of the formula X with heterocyclylcarbonyl compounds of the formula VII to give benzoyl derivatives of the formula III where $R^9$=hydroxyl is usually carried out at temperatures of from 0° C. to 100° C., preferably from 10° C. to 50° C., in an inert organic solvent in the presence of a base [cf., for example, U.S. Pat. No. 4,904,674; Hellmann, H. et al., Liebigs Ann. Chem. 631 (1960), 175-179].

If $L^4$ in the N-acylaminomalonyl compounds of the formula X is $C_1$-$C_6$-alkoxy, it is advantageous to initially convert $L^4$ by ester hydrolysis [for example Hellmann, H. et al., Liebigs Ann. Chem. 631 (1960), 175-179] into a hydroxyl group.

Suitable solvents are aliphatic hydrocarbons, such as pentane, hexane, cyclohexane and mixtures of $C_5$-$C_8$-alkanes, aromatic hydrocarbons, such as toluene, o-, m- and p-xylene, halogenated hydrocarbons, such as methylene chloride, chloroform and chlorobenzene, ethers, such as diethyl ether, diisopropyl ether, tert-butyl methyl ether, dioxane, anisole and tetrahydrofuran, nitriles, such as acetonitrile and propionitrile, ketones, such as acetone, methyl ethyl ketone, diethyl ketone and tert-butyl methyl ketone, alcohols, such as methanol, ethanol, n-propanol, isopropanol, n-butanol and tert-butanol, and also dimethyl sulfoxide, dimethylformamide and dimethylacetamide, particularly preferably diethyl ether, dioxane and tetrahydrofuran.

It is also possible to use mixtures of the solvents mentioned.

Suitable bases are, in general, inorganic compounds, such as alkali metal and alkaline earth metal hydroxides, such as lithium hydroxide, sodium hydroxide, potassium hydroxide and calcium hydroxide, alkali metal and alkaline earth metal oxides, such as lithium oxide, sodium oxide, calcium oxide and magnesium oxide, alkali metal and alkaline earth metal hydrides, such as lithium hydride, sodium hydride, potassium hydride and calcium hydride, alkali metal amides, such as lithium amide, sodium amide and potassium amide, alkali metal and alkaline earth metal carbonates, such as lithium carbonate, potassium carbonate and calcium carbonate, and also alkali metal bicarbonates, such as sodium bicarbonate, organometallic compounds, in particular alkali metal alkyls, such as methyllithium, butyllithium and phenyllithium, alkylmagnesium halides, such as methylmagnesium chloride, and also alkali metal and alkaline earth metal alkoxides, such as sodium methoxide, sodium ethoxide, potassium ethoxide, potassium tert-butoxide, potassium tert-pentoxide and dimethoxymagnesium, moreover organic bases, for example tertiary amines, such as trimethylamine, triethylamine, diisopropylethylamine and N-methylpiperidine, pyridine, substituted pyridines, such as collidine, lutidine and 4-dimethylaminopyridine, and also bicyclic amines. Particular preference is given to triethylamine and diisopropylethylamine.

The bases are generally employed in catalytic amounts; however, they can also be used in equimolar amounts, in excess or, if appropriate, as solvent.

Ann. Chem. 631 (1960), 175-179], or they can be prepared in accordance with the literature cited.

The required heterocyclic compounds of the formula VII are commercially available.

Process D

Benzoyl derivatives of the formula III where $R^9$=hydroxyl and $R^{10}$=hydrogen can also be obtained by initially acylating keto compounds of the formula XIII with benzoic acids/benzoic acid derivatives of the formula IV to give the corresponding N-acyl keto compounds of the formula XII, followed by reduction of the keto group [Girard A., Tetrahedron Lett. 37(44) (1996), 7967-7970; Nojori R., J. Am. Chem. Soc. 111(25) (1989), 9134-9135; Schmidt U., Synthesis (12) (1992), 1248-1254; Bolhofer, A., J. Am. Soc. 75 (1953), 4469]:

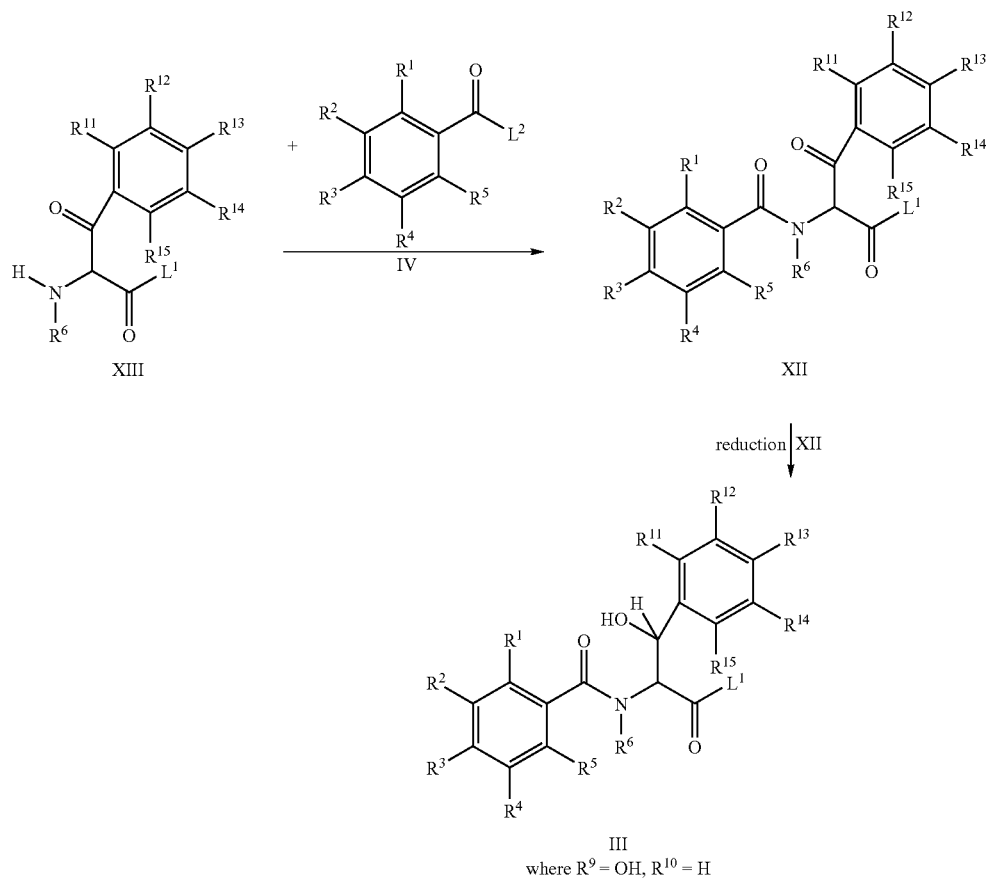

The starting materials are generally reacted with one another in equimolar amounts. It may be advantageous to employ an excess of base, based on X.

Work-up and isolation of the products can be carried out in a manner known per se.

The resulting benzoyl derivatives of the formula III where $R^9$=hydroxyl can then, in accordance with the processes A and B mentioned above, be converted into the desired benzoyl-substituted phenylalanineamides of the formula I where $R^9$=$OR^{16}$.

The required aminomalonyl compounds of the formula XI are commercially available or known from the literature [for example U.S. Pat. No. 4,904,674; Hellmann, H. et al., Liebigs $L^1$ is a nucleophilically displaceable leaving group, for example hydroxyl or $C_1$-$C_6$-alkoxy.

$L^2$ is a nucleophilically displaceable leaving group, for example hydroxyl, halogen, $C_1$-$C_6$-alkylcarbonyl, $C_1$-$C_6$-alkoxycarbonyl, $C_1$-$C_6$-alkylsulfonyl, phosphoryl or isoureyl.

The acylation of the keto compounds of the formula XIII with benzoic acids/benzoic acid derivatives of the formula IV give N-acyl keto compounds of the formula XII is usually carried out analogously to the reaction, mentioned in process A, of phenylalanines of the formula V with benzoic acids/benzoic acid derivatives of the formula IV to give the corresponding benzoyl derivatives of the formula III.

The keto compounds of the formula XIII required for preparing the benzoyl derivatives of the formula III where $R^9$=hydroxyl and $R^{10}$=hydrogen are known from the literature [WO 02/083111; Boto, A. et al., Tetrahedron Letters 39 (44) (1988), 8167-8170; von Geldern, T. et al., J. Med. Chem. 39(4) (1996), 957-967; Singh, J. et al., Tetrahedron Letters 34 (2) (1993), 211-214; ES 2021557; Maeda, S. et al., Chem. Pharm. Bull. 32 (7) (1984), 2536-2543; Ito, S. et al., J. Biol. Chem. 256 (15) (1981), 7834-4783; Vinograd, L. et al., Zhurnal Organischeskoi Khimii 16 (12) (1980), 2594-2599; Castro, A. et al., J. Org. Chem. 35 (8) (1970), 2815-2816; JP 02-172956; Suzuki, M. et al., J. Org. Chem. 38 (20) (1973), 3571-3575; Suzuki, M. et al., Synthetic Communications 2 (4) (1972), 237-242], or they can be prepared in accordance with the literature cited.

The reduction of the N-acyl keto compounds of the formula XII to benzoyl derivatives of the formula III where $R^9$=hydroxyl and $R^{10}$=hydrogen is usually carried out at temperatures of from 0° C. to 100° C., preferably from 20° C. to 80° C., in an inert organic solvent in the presence of a reducing agent.

Suitable solvents are aliphatic hydrocarbons, such as pentane, hexane, cyclohexane and mixtures of $C_5$-$C_8$-alkanes, aromatic hydrocarbons, such as toluene, o-, m- and p-xylene, halogenated hydrocarbons, such as methylene chloride, chloroform and chlorobenzene, ethers, such as diethyl ether, diisopropyl ether, tert-butyl methyl ether, dioxane, anisole and tetrahydrofuran, nitriles, such as acetonitrile and propionitrile, ketones, such as acetone, methyl ethyl ketone, diethyl ketone and tert-butyl methyl ketone, alcohols, such as methanol, ethanol, n-propanol, isopropanol, n-butanol and tert-butanol, and also dimethyl sulfoxide, dimethylformamide and dimethylacetamide, particularly preferably toluene, methylene chloride or tert-butyl methyl ether.

It is also possible to use mixtures of the solvents mentioned.

Suitable reducing agents are, for example, sodium borohydride, zinc borohydride, sodium cyanoborohydride, lithium triethylborohydride (Superhydrid®)), lithium tri-sec-butylborohydride (L-Selectrid®)), lithium aluminum hydride or borane [cf. for example, WO 00/20424; Marchi, C. et al., Tetrahedron 58 (28) (2002), 5699; Blank, S. et al., Liebigs Ann. Chem. (8) (1993), 889-896; Kuwano, R. et al., J. Org Chem. 63 (10) (1998), 3499-3503; Clariana, J. et al., Tetrahedron 55 (23) (1999), 7331-7344].

It is furthermore also possible to carry out the reduction in the presence of hydrogen and a catalyst. Suitable catalysts are, for example, [Ru(BINAP)Cl$_2$] or Pd/C [cf. Noyori, R. et al., J. Am. Chem. Soc. 111 (25) (1989), 9134-9135; Bolhofer, A. et al., J. Am. Chem. Soc. 75 (1953), 4469].

In addition, the reduction can also be carried out in the presence of a microorganism. A suitable microorganism is, for example, *Saccharomyces Rouxii* [cf. Soukup, M. et al., Helv. Chim. Acta 70 (1987), 232].

The N-acyl keto compounds of the formula XII and the respective reducing agent are generally reacted with one another in equimolar amounts. It may be advantageous to employ an excess of reducing agent, based on XII.

Work-up and isolation of the products can be carried out in a manner known per se.

The resulting benzoyl derivatives of the formula III where $R^9$=hydroxyl and $R^{10}$=hydrogen can then be reacted in accordance with the processes A and B mentioned above to give the desired benzoyl-substituted phenylalanineamides of the formula I where $R^9$=$OR^{16}$.

The present invention also provides benzoyl derivatives of the formula III

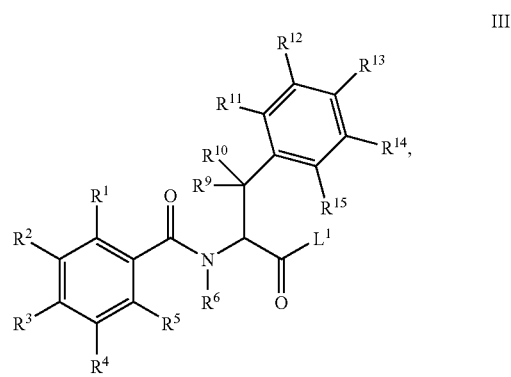

where $R^1$ to $R^6$ and $R^9$ to $R^{15}$ are as defined in claim 1 and $L^1$ is a nucleophilically displaceable leaving group, such as hydroxyl or $C_1$-$C_6$-alkoxy.

The particularly preferred embodiments of the benzoyl derivatives of the formula III with respect to the variables correspond to those of the radicals $R^1$ to $R^6$ and $R^9$ to $R^{15}$ of the formula I.

Particular preference is given to benzoyl derivatives of the formula III in which $R^1$ is fluorine, chlorine or $CF_3$, $R^2$ and $R^3$ independently of one another are hydrogen, fluorine or chlorine, $R^4$, $R^5$ and $R^6$ are hydrogen, $R^9$ is $OR^{16}$, $SR^{17}$ or $NR^{18}R^{19}$;

$R^{10}$ is hydrogen;

$R^{11}$ is hydrogen, fluorine or $CH_3$;

$R^{12}$ is hydrogen, fluorine or chlorine;

$R^{13}$, $R^{14}$ and $R^{15}$ are hydrogen;

$R^{16}$ and $R^{18}$ independently of one another are hydrogen, $C_1$-$C_4$-alkylcarbonyl, $C_1$-$C_4$-alkylaminocarbonyl, di($C_1$-$C_4$-alkyl)aminocarbonyl, phenylaminocarbonyl, N—($C_1$-$C_4$-alkyl)-N-(phenyl)aminocarbonyl, $SO_2CH_3$, $SO_2CF_3$ or $SO_2(C_6H_5)$;

$R^{17}$ is hydrogen, $C_1$-$C_4$-alkylcarbonyl, $C_1$-$C_4$-alkoxycarbonyl, $C_1$-$C_4$-alkylaminocarbonyl, di($C_1$-$C_4$-alkyl)aminocarbonyl, N—($C_1$-$C_4$-alkoxy-N—$C_1$-$C_4$-alkyl)aminocarbonyl; and $R^{19}$ is hydrogen or $C_1$-$C_4$-alkyl.

EXAMPLE 1

(2S,3R)-2-(4-Fluoro-2-trifluoromethylbenzoylamino)-2-methylcarbamoyl-1-o-tolylethyl methylphenylcarbamate (Tab. 3. No. 3.34)

1.1) Ethyl 2-amino-3-oxo-3-o-tolylpropionate hydrochloride

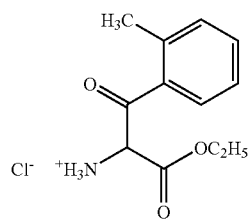

Under nitrogen, 4.2 g (0.038 mol) of potassium tert-butoxide were suspended in THF. The mixture was cooled to −78° C., and 10.0 g (0.037 mol) of ethyl N-(diphenylmethylene)glycinate, dissolved in THF, were added dropwise. After 40 min at −78° C., the solution was transferred into a cooled dropping funnel (−78° C.) and added dropwise to a solution, cooled to −78° C., of 2-methylbenzoyl chloride in THF. After 1 h of stirring at −78° C., the reaction mixture was allowed to warm to 0° C. over a period of 2 h. The mixture was hydrolyzed using 10% strength hydrochloric acid, and stirring was continued. The solvents were removed and the residue was taken up in water and washed with MTBE. The aqueous phase was concentrated, methanol was added to the residue and the mixture was filtered. Concentration of the filtrate gave 6.2 g of the title compound as a colorless oil.

$^1$H-NMR (DMSO): δ=9.3 (br, 3H, NH); 7.3-7.6 (m, 4H), 4.1 (m, 2H); 3.7 (m, 1H); 2.40 (s, 3H); 0.95 (t, 3H).

1.2) Ethyl 2-(4-fluoro-2-trifluoromethylbenzoylamino)-3-oxo-3-o-tolylpropionate

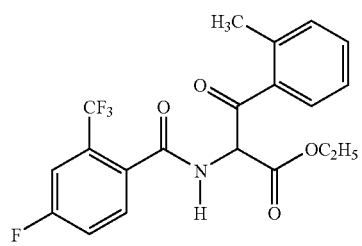

6.2 g (0.024 mol) of ethyl 2-amino-3-oxo-3-o-tolylpropionate hydrochloride were dissolved in methylene chloride, and 9.7 g (0.096 mol) of triethylamine were added. At 0° C., 5.4 g (0.024 mol) of 4-fluoro-2-trifluoromethylbenzoyl chloride, dissolved in methylene chloride, were added dropwise. The mixture was stirred at room temperature (RT) for 1 h, and 5% strength hydrochloric acid was then added. The organic phase was separated off, washed and dried, and the solvent was removed. Chromatographic purification (silica gel column, cyclohexane/ethyl acetate) gave 4.7 g of the title compound as colorless crystals.

$^1$H-NMR (DMSO): δ=9.61 (d, 1H); 7.3-7.9 (m, 7H); 6.18 (d, 1H); 4.1-4.3 (m, 2H); 2.40 (s, 3H); 1.15 (t, 3H).

1.3) Ethyl (2S,3R)-2-(4-fluoro-2-trifluoromethylbenzoylamino)-3-hydroxy-3-o-tolylpropionate

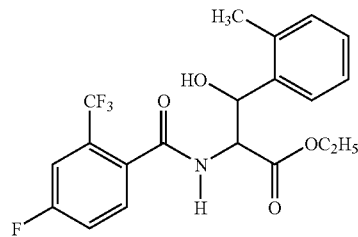

4.7 g (0.0114 mol) of ethyl 2-(4-fluoro-2-trifluoromethylbenzoylamino)-3-oxo-3-o-tolylpropionate were dissolved in methylene chloride, the solution was degassed in an ultrasonic bath and 200 mg of catalyst mix were added. The catalyst mix had been prepared beforehand by heating 78 mg of dichloro(p-cymene)ruthenium(II) dimer (RuCl$_2$Cy) and 138 mg of BINAP in methylene chloride and ethanol at 50° C. for 1 h, followed by removal of the solvents.

The solution was heated under a hydrogen pressure of 80 bar at 50° C. for 90 h. Removal of the solvents and chromatographic purification (silica gel column, cyclohexane/ethyl acetate) gave 3.4 g of the title compound as colorless crystals.

$^1$H-NMR (DMSO): δ=8.95 (d, 1H); 7.0-8.7 (m, 7H); 5.80 (d, 1H); 5.40 (t, 1H); 4.75 (dd, 1H); 4.10 (m, 2H); 2.30 (s, 3H); 1.20 (t, 3H).

1.4) (2S,3R)—N-Methyl-2-(4-fluoro-2-trifluoromethylbenzoylamino)-3-hydroxy-3-o-tolylpropionamide

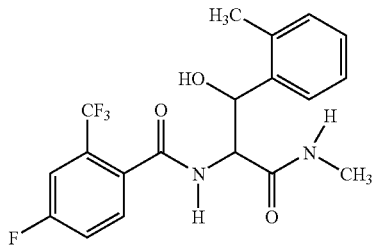

3.4 g (0.0082 mol) of ethyl (2S,3R)-2-(4-fluoro-2-trifluoromethylbenzoylamino)-3-hydroxy-3-o-tolylpropionate were dissolved in ethanol. Methylamine gas was introduced at room temperature. After 1.5 h, the mixture was warmed to 30-35° C. for 1 h. Removal of the solvents gave 3.1 g of the title compound as colorless crystals.

$^1$H-NMR (DMSO): δ=8.45 (d, 1H); 7.0-7.7 (m, 7H); 5.70 (d, 1H); 5.30 (t, 1H); 4.65 (dd, 1H); 2.65 (d, 3H); 2.40 (s, 3H); 1.10 (t, 3H).

1.5) (2S,3R)—N-Methyl-2-(4-fluoro-2-trifluoromethylbenzoylamino)-3-(N-phenyl-N-methylaminocarbonyloxy)-3-o-tolylpropionamide (Tab. 3, No. 3.34)

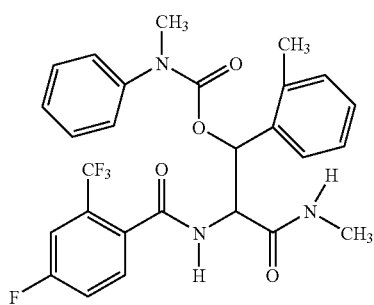

0.4 g (0.001 mol) of (2S,3R)—N-methyl-2-(4-fluoro-2-trifluoromethylbenzoylamino)-3-hydroxy-3-o-tolylpropionamide was dissolved in methylene chloride, 0.13 g (0.0013 mol) of triethylamine and a spatula-tip of 4-dimethylaminopyridine were added, and 0.22 g of N-phenyl-N-methylcarbamoyl chloride in methylene chloride was added dropwise. The suspension was stirred for 15 hours and then extracted with 5% strength hydrochloric acid and NaHCO$_3$ solution and dried. Chromatographic purification (silica gel column, cyclohexane/ethyl acetate) gave 0.28 g of the title compound as a colorless oil.

$^1$H-NMR (DMSO): δ=8.8 (br, 1H); 7.0-7.6 (m, 12H); 5.70 (d, 1H); 5.30 (br, 1H); 4.85 (dd, 1H); 2.75 (d, 3H); 2.55 (d, 3H); 2.40 (s, 3H).

EXAMPLE 2

N-[2-(Benzylformylamino)-1-methylcarbamoyl-2-phenylethyl]-4-fluoro-2-trifluoromethylbenzamide (Tab. 3. No. 3.43)

2.1) Ethyl 1-benzyl-5-phenyl-4,5-dihydro-1H-imidazole-4-carboxylate

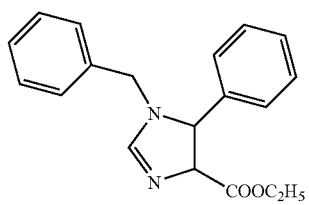

25.7 g (0.1305 mol) of benzylidenebenzylamine were dissolved in ethanol, and 15.2 g (0.1305 mol) of ethyl isocyanoacetate were added dropwise. The solution was heated under reflux for 16 h. Removal of the solvents and drying gave 40.2 g of the title compound as a colorless oil.

$^1$H-NMR (DMSO): δ=7.1-7.4 (m, 10H); 4.6 (d, 1H); 4.5 (d, 1H); 4.3 (d, 1H); 4.1 (q, 2H); 3.8 (d, 1H); 1.1 (t, 3H).

2.2) 2-Amino-3-(N-benzyl-N-formylamino)-3-phenylpropionic acid

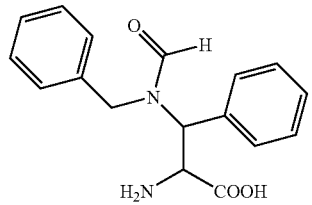

14.8 g (0.048 mol) of ethyl 1-benzyl-5-phenyl-4,5-dihydro-1H-imidazole-4-carboxylate were heated under reflux in 100 ml of 47% strength HBr solution for 3 h. The solvents were removed and the residue was stirred with water and filtered. The solvents were removed and the residue was taken up in ethanol and diluted with diethyl ether. The resulting suspension was filtered and the solvents were removed. This gave 14.0 g of the title compound as a crude product which was used in the next step without purification.

2.3) Methyl 2-amino-3-(N-benzyl-N-formylamino)-3-phenylpropionate

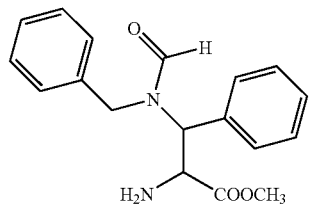

13.5 g (0.04 mol) of 2-amino-3-(N-benzyl-N-formylamino)-3-phenylpropionic acid were dissolved in methanol, and 7.1 g (0.06 mol) of thionyl chloride and 1 drop of DMF were added dropwise. After 20 hours, the solvents were removed, the residue was suspended in diethyl ether and 5% strength NaHCO$_3$ solution was added with stirring. The ether phase was separated off, washed and dried. Removal of the solvents gave 4.0 g of the title compound as a colorless oil which was used without further purification.

2.4) Methyl 3-(N-benzyl-N-formylamino)-2-(4-fluoro-2-trifluoromethylbenzoylamino)-3-phenylpropionate

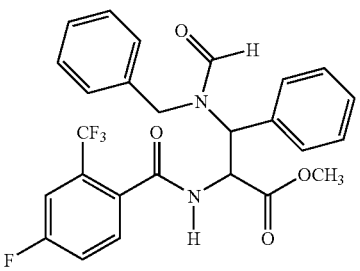

1.4 g (0.0052 mol) of methyl 2-amino-3-(N-benzyl-N-formylamino)-3-phenylpropionate were dissolved in methylene chloride, and 1.0 g (0.0052 mol) of 4-fluoro-2-trifluoromethylbenzoic acid and 1.0 g (0.010 mol) of triethylamine in THF were added. At 0-5° C., 1.3 g (0.0052 mol) of bis(2-oxo-3-oxazolidinyl)phosphoryl chloride were added. After 2 h at 0° C., the mixture was stirred at room temperature for 15 h. The solvents were removed and the residue was taken up in ethyl acetate, washed and dried. Chromatographic purification (silica gel column, cyclohexane/ethyl acetate) gave 0.65 g of the title compound as a colorless oil.

$^1$H-NMR (DMSO): δ=8.45 (s, 1H); 7.95 (d 1H); 7.00-7.40 (m. 13H); 5.40-5.55 (m, 2H); 4.38 (q, 2H); 3.60 (s, 3H).

2.5) N-[2-(N-Benzyl-N-formylamino)-1-methylcarbamoyl-2-phenylethyl]-4-fluoro-2-trifluoromethylbenzamide (Tab. 3, No. 3.43)

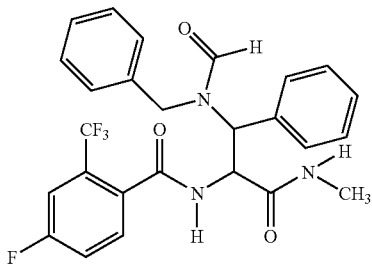

0.65 g (0.00129 mol) of methyl 3-(N-benzyl-N-formylamino)-2-(4-fluoro-2-trifluoromethylbenzoylamino)-3-phenylpropionate was dissolved in 1 methanol. Methylamine gas was introduced at 0° C., and after 1 h, the mixture was warmed to room temperature for 18 h. Removal of the solvents and customary purification methods gave 550 mg of the title compound as colorless crystals.

$^1$H-NMR (DMSO): δ=9.20 (d, 1H); 8.51 (s, 1H); 8.30 (m, 1H); 6.75-7.75 (m, 12H); 5.52 (t, 1H); 5.07 (d, 1H); 4.52 (d, 1H); 4.20 (d, 1H); 2.40 (d, 3H).

EXAMPLE 3

3-Chloro-2-trifluoromethylbenzoic acid

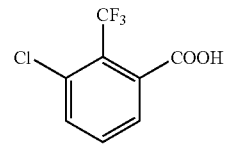

1.03 g (42.4 mmol) of magnesium turnings were dissolved in THF. 2 drops of 1,2-dibromomethane were added, and the reaction mixture was, after the exothermal reaction had set in, stirred at 32-35° C. with ice cooling. 10.0 g (38.5 mmol) of 1-bromo-3-chloro-2-trifluoromethylbenzene in THF were then added dropwise such that the temperature did not exceed 32° C. The mixture was stirred for another 30 min and cooled to 0° C., and carbon dioxide was introduced for 2 h. The mixture was then warmed to room temperature, and $CO_2$ was introduced for another hour.

The solution was poured into a mixture of 1M hydrochloric acid and ice and extracted with methyl tert-butyl ether. The organic phase was then extracted with 1M NaOH and the aqueous phase was acidified with conc. hydrochloric acid and extracted with methylene chloride. Drying and distillative removal of the solvent gave 7.7 g (84% of theory) of the title compound as colorless crystals (m.p. 110° C.).

Further benzoyl derivatives of the formula III and benzoyl-substituted phenylalanineamides of the formula I which were prepared or are preparable analogously to the processes described above are, in addition to the compounds above, listed in Tables 2 and 3 below.

TABLE 2

III

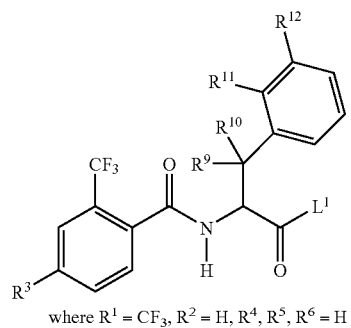

where $R^1 = CF_3$, $R^2 = H$, $R^4$, $R^5$, $R^6 = H$
$R^{10} = H$, $R^{15} = H$

| No. | $R^3$ | $R^9$ | $R^{11}$ | $R^{12}$ | $R^{13}$ | $R^{14}$ | $L^1$ | erythro/threo | Configuration | m.p. or m/z |
|---|---|---|---|---|---|---|---|---|---|---|
| 2.1 | H | OH | H | H | H | H | $OCH_3$ | erythro | rac | 115 |
| 2.2 | H | OH | H | H | H | H | OH | threo | rac | 110 |
| 2.3 | F | OH | H | H | H | H | $OC_2H_5$ | erythro | rac | 93 |
| 2.4 | F | OH | H | F | H | H | $OC_2H_5$ | threo | 2-S, 3-R | 96 |
| 2.5 | F | OH | $CH_3$ | F | H | H | $OC_2H_5$ | threo | 2-S, 3-R | 141 |
| 2.6 | H | OH | H | H | H | H | $OC_2H_5$ | erythro | rac | 93 |
| 2.7 | H | OH | H | H | H | H | $OCH_3$ | threo | rac | 114 |
| 2.8 | H | $OCOC(CH_3)_3$ | H | H | H | H | $OCH_3$ | threo | rac | 157 |
| 2.9 | F | OH | H | $CF_3$ | H | H | OH | threo | rac | 33 |

TABLE 2-continued

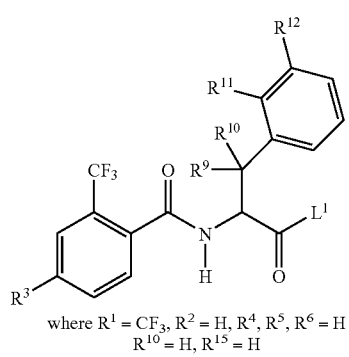

where $R^1 = CF_3$, $R^2 = H$, $R^4$, $R^5$, $R^6 = H$
$R^{10} = H$, $R^{15} = H$

| No. | $R^3$ | $R^9$ | $R^{11}$ | $R^{12}$ | $R^{13}$ | $R^{14}$ | $L^1$ | erythro/threo | Config-uration | m.p. or m/z |
|---|---|---|---|---|---|---|---|---|---|---|
| 2.10 | F | OH | H | OCH$_3$ | H | H | OC$_2$H$_5$ | threo | 2-S, 3-R | 128 |
| 2.11 | F | OH | H | NO$_2$ | H | H | OCH$_3$ | erythro | rac | 119 |
| 2.12 | F | OH | H | NO$_2$ | H | H | OCH$_3$ | threo | rac | 130 |
| 2.13 | F | OH | H | H | CF$_3$ | H | OH | threo | rac | 145 |
| 2.14 | F | OH | Cl | H | H | H | OH | threo | rac | 188 |
| 2.15 | F | OH | Cl | CF$_3$ | H | H | OH | threo | rac | 155 |
| 2.16 | F | OH | Cl | Cl | H | H | OH | threo | rac | 192 |
| 2.17 | F | OH | Cl | H | Cl | H | OH | threo | rac | 190 |
| 2.18 | F | OH | Cl | H | H | Cl | OH | threo | rac | 202 |
| 2.19 | F | OH | OCH$_2$C$_6$H$_5$ | H | H | H | OC$_2$H$_5$ | threo | 2-S, 3-R | 164 |
| 2.20 | F | OCOCH$_3$ | Cl | H | H | H | OH | threo | rac | 188 |
| 2.21 | F | OCON(CH$_3$)$_2$ | H | NO$_2$ | H | H | OCH$_3$ | threo | rac | 133 |
| 2.22 | F | OSi(CH$_3$)$_2$C(CH$_3$)$_3$ | H | H | H | H | OH | threo | rac | m/z 485 |
| 2.23 | F | OSi(CH$_3$)$_2$C(CH$_3$)$_3$ | H | H | H | H | OCH$_3$ | threo | rac | 114 |
| 2.24 | F | NHCH$_2$C$_6$H$_5$ | H | H | H | H | OCH$_3$ | 4:1 | rac | oil |

TABLE 3

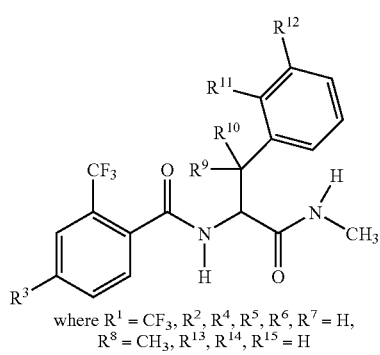

where $R^1 = CF_3$, $R^2$, $R^4$, $R^5$, $R^6$, $R^7 = H$,
$R^8 = CH_3$, $R^{13}$, $R^{14}$, $R^{15} = H$

| No. | $R^3$ | $R^9$ | $R^{10}$ | $R^{11}$ | $R^{12}$ | erthro/threo | Config. | m.p. or m/z |
|---|---|---|---|---|---|---|---|---|
| 3.1 | H | OH | H | H | H | erythro | rac | oil |
| 3.2 | H | OH | H | H | H | threo | rac | 154 |
| 3.3 | H | OH | CH$_3$ | H | H | threo | rac | 206 |
| 3.4 | H | OH | H | CH$_3$ | H | threo | rac | 209 |
| 3.5 | F | OH | H | H | H | erythro | rac | 225 |
| 3.6 | F | OH | H | H | H | threo | rac | 155 |
| 3.7 | F | OH | H | H | F | threo | 2-S, 3-R | 90 |
| 3.8 | F | OH | CH$_3$ | H | H | threo | rac | 167 |
| 3.9 | F | OH | H | CH$_3$ | H | threo | 2-S, 3-R | 62 |
| 3.10 | F | OH | H | CH$_3$ | F | threo | 2-S, 3-R | 41 |
| 3.11 | F | OH | H | CH$_3$ | Cl | threo | 2-S, 3-R | oil |
| 3.12 | F | OCH$_3$ | H | H | H | threo | rac | 155 |
| 3.13 | F | O—CH$_2$—C$_6$H$_5$ | H | H | H | threo | rac | 168 |
| 3.14 | H | O—CH$_2$—(o-CF$_3$—C$_6$H$_4$) | H | H | H | threo | rac | 137 |
| 3.15 | H | O—CH$_2$—(o-CF$_3$—C$_6$H$_4$) | CH$_3$ | H | H | threo | rac | oil |
| 3.16 | F | O—CH$_2$—(2,4,6-Cl$_3$—C$_6$H$_2$) | H | H | H | threo | rac | 180 |

TABLE 3-continued

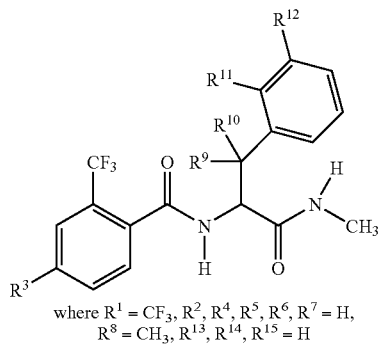

where $R^1$ = $CF_3$, $R^2$, $R^4$, $R^5$, $R^6$, $R^7$ = H,
$R^8$ = $CH_3$, $R^{13}$, $R^{14}$, $R^{15}$ = H

| No. | $R^3$ | $R^9$ | $R^{10}$ | $R^{11}$ | $R^{12}$ | erthro/threo | Config. | m.p. or m/z |
|---|---|---|---|---|---|---|---|---|
| 3.17 | H | OCOCH$_3$ | H | H | H | threo | rac | 196 |
| 3.18 | F | OCOCH$_3$ | H | H | H | threo | rac | 218 |
| 3.19 | F | OCOCH$_3$ | H | CH$_3$ | H | threo | 2-S, 3-R | 165 |
| 3.20 | F | OCOCH(CH$_3$)$_2$ | H | H | H | threo | rac | 181 |
| 3.21 | H | OCOC(CH$_3$)$_3$ | H | H | H | erythro | rac | 190 |
| 3.22 | H | OCOC(CH$_3$)$_3$ | H | H | H | threo | rac | 140 |
| 3.23 | F | OCOC(CH$_3$)$_3$ | H | H | H | threo | rac | oil |
| 3.24 | F | OCOC(CH$_3$)$_3$ | H | CH$_3$ | H | threo | 2-S, 3-R | 183 |
| 3.25 | F | OCOC(CH$_3$)$_3$ | H | CH$_3$ | F | threo | 2-S, 3-R | 189 |
| 3.26 | H | OCON(CH$_3$)$_2$ | H | H | H | erythro | rac | oil |
| 3.27 | F | OCON(CH$_3$)$_2$ | H | H | H | threo | rac | 120 |
| 3.28 | F | OCON(CH$_3$)$_2$ | H | CH$_3$ | H | threo | 2-S, 3-R | oil |
| 3.29 | F | OCON(CH$_3$)$_2$ | H | CH$_3$ | F | threo | 2-S, 3-R | 170 |
| 3.30 | F | OCON(CH$_3$)$_2$ | H | CH$_3$ | Cl | threo | 2-S, 3-R | oil |
| 3.31 | F | OCONH(C$_6$H$_5$) | H | H | H | threo | rac | 207 |
| 3.32 | F | OCONH(m-Cl—C$_6$H$_4$) | H | H | H | threo | rac | 200 |
| 3.33 | F | OCONH(m-CN—C$_6$H$_4$) | H | H | H | threo | rac | 140 |
| 3.34 | F | OCON(CH$_3$)(C$_6$H$_5$) | H | CH$_3$ | H | threo | 2-S, 3-R | oil |
| 3.35 | F | OCO—N-morpholinyl | H | CH$_3$ | H | threo | 2-S, 3-R | oil |
| 3.36 | H | OCOOCH$_2$CH(CH$_3$)$_2$ | H | H | H | threo | rac | 142 |
| 3.37 | F | OCOOCH$_2$CH(CH$_3$)$_2$ | H | H | H | threo | rac | 136 |
| 3.38 | H | OSO$_2$CH$_3$ | H | H | H | threo | rac | 141 |
| 3.39 | F | OSO$_2$CH$_3$ | H | H | H | threo | rac | 135 |
| 3.40 | F | OSO$_2$CH$_3$ | H | CH$_3$ | H | threo | 2-S, 3-R | 90 |
| 3.41 | F | S—CH$_2$—C$_6$H$_5$ | H | CH$_3$ | H | 1:1 | rac | 162 |
| 3.42 | H | NH—C$_6$H$_5$ | H | H | H | 1:1 | rac | oil |
| 3.43 | F | N—(CH$_2$—C$_6$H$_5$)(CHO) | H | H | H | erythro | rac | 212 |
| 3.44 | F | NHSO$_2$CH$_3$ | H | H | H | 4:1 | rac | 217 |
| 3.45 | F | OH | H | H | H | threo | rac | 203 |
| 3.46 | F | OH | H | H | F | threo | 2-S, 3-R | 90 |
| 3.47 | F | OH | H | H | Br | threo | 2-S, 3-R | 165 |
| 3.48 | F | OH | H | H | CF$_3$ | threo | rac | 161 |
| 3.49 | F | OH | H | H | OCH$_3$ | threo | 2-S, 3-R | 188 |
| 3.50 | F | OH | H | H | NO$_2$ | erythro | rac | m/z 429 |
| 3.51 | F | OH | H | H | NO$_2$ | threo | rac | 207 |
| 3.52 | F | OH | H | H | C$_6$H$_5$ | threo | rac | 198 |
| 3.53 | F | OH | H | H | 4-Cl—C$_6$H$_4$ | threo | rac | 183 |
| 3.54 | F | OH | H | H | 3,5-Cl$_2$—C$_6$H$_3$ | threo | rac | 202 |
| 3.55 | F | OH | H | H | 4-CH$_3$—C$_6$H$_4$ | threo | rac | 198 |
| 3.56 | F | OH | H | H | 3-CF$_3$—C$_6$H$_4$ | threo | rac | 177 |
| 3.57 | F | OH | H | H | 3-NO$_2$—C$_6$H$_4$ | threo | rac | 185 |
| 3.58 | F | OH | H | H | 4-Cl-2-thienyl | threo | rac | 133 |
| 3.59 | F | OH | H | Cl | H | threo | rac | 172 |
| 3.60 | F | OH | H | CF$_3$ | H | threo | rac | 142 |
| 3.61 | F | OH | H | CH$_2$OH | H | threo | 2-S, 3-R | 152 |
| 3.62 | F | OH | H | CH$_2$OCOCH$_3$ | H | threo | 2-S, 3-R | m/z 456 |
| 3.63 | F | OH | H | CH$_2$OCH$_2$COOH | H | threo | 2-S, 3-R | m/z 472 |
| 3.64 | F | OH | H | CH$_2$OCONHSO$_2$CF$_3$ | H | threo | 2-S, 3-R | m/z 589 |
| 3.65 | F | OH | H | CH$_2$OSO$_2$CH$_3$ | H | threo | 2-S, 3-R | 97 |
| 3.66 | F | OH | H | OCH$_2$C$_6$H$_5$ | H | threo | 2-S, 3-R | 150 |
| 3.67 | F | OH | H | NO$_2$ | H | threo | rac | m/z 429 |
| 3.68 | F | OH | H | NH$_2$ | H | threo | 2-S, 3-R | m/z 399 |
| 3.69 | F | OH | H | NHCOCH$_3$ | H | threo | 2-S, 3-R | m/z 441 |
| 3.70 | F | OH | H | NHSO$_2$CH$_3$ | H | threo | 2-S, 3-R | m/z 477 |
| 3.71 | F | OH | H | NHSO$_2$CF$_3$ | H | threo | 2-S, 3-R | m/z 531 |
| 3.72 | F | OH | H | Cl | CF$_3$ | threo | rac | 172 |
| 3.73 | NHCH$_3$ | OH | H | CH$_3$ | F | threo | 2-S, 3-R | 131 |
| 3.74 | F | OCOCH$_3$ | H | Cl | H | threo | rac | 145 |

TABLE 3-continued

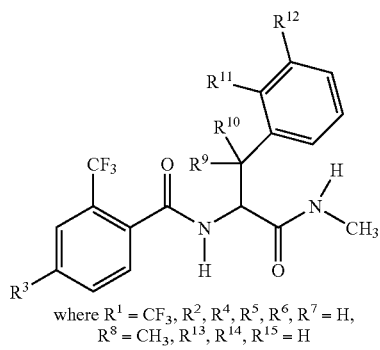

where $R^1 = CF_3$, $R^2$, $R^4$, $R^5$, $R^6$, $R^7 = H$,
$R^8 = CH_3$, $R^{13}$, $R^{14}$, $R^{15} = H$

| No. | $R^3$ | $R^9$ | $R^{10}$ | $R^{11}$ | $R^{12}$ | erthro/threo | Config. | m.p. or m/z |
|---|---|---|---|---|---|---|---|---|
| 3.75 | F | OCOCH$_3$ | H | H | F | threo | rac | 161 |
| 3.76 | F | OCOCH$_3$ | H | H | CF$_3$ | threo | rac | 176 |
| 3.77 | F | OCOCH$_3$ | H | Cl | Cl | threo | rac | 200 |
| 3.78 | F | OCOCH$_3$ | H | CH$_3$ | F | threo | 2-S, 3-R | 138 |
| 3.79 | F | OCOCH$_3$ | H | Cl | CF$_3$ | threo | rac | 215 |
| 3.80 | F | OCOC(CH$_3$)$_3$ | H | H | H | erythro | rac | m/z 468 |
| 3.81 | F | OCOC(CH$_3$)$_3$ | H | H | F | threo | 2-S, 3-R | 185 |
| 3.82 | F | OCOC(CH$_3$)$_3$ | H | H | Br | threo | 2-S, 3-R | 142 |
| 3.83 | F | OCOC(CH$_3$)$_3$ | H | Cl | Cl | threo | rac | 185 |
| 3.84 | F | OCOCH=CH$_2$ | H | CH$_3$ | F | threo | 2-S, 3-R | 187 |
| 3.85 | F | OCO(C$_3$H$_5$) | H | H | H | threo | rac | m/z 452 |
| 3.86 | F | OCO(C$_4$H$_7$) | H | H | H | threo | rac | m/z 466 |
| 3.87 | F | OCOCH$_2$Cl | H | CH$_3$ | F | threo | 2-S, 3-R | 158 |
| 3.88 | F | OCOCH$_2$OCH$_3$ | H | H | H | threo | rac | m/z 456 |
| 3.89 | F | OCOCH$_2$OCH$_3$ | H | H | F | threo | 2-S, 3-R | 185 |
| 3.90 | F | OCOCH$_2$SCH$_3$ | H | H | H | threo | rac | 160 |
| 3.91 | F | OCOCH$_2$SCH$_3$ | H | CH$_3$ | F | threo | 2-S, 3-R | 134 |
| 3.92 | F | OCOCH$_2$CH(OH)COCH | H | CH$_3$ | F | threo | 2-S, 3-R | m/z 532 |
| 3.93 | F | OCOCH$_2$CH$_2$COOCH$_3$ | H | H | H | threo | rac | m/z 512 |
| 3.94 | F | OCOCH$_2$OCH$_2$CH$_2$OCH$_2$CH$_2$OCH$_3$ | H | H | H | threo | rac | m/z 544 |
| 3.95 | F | OCOCH$_2$OCH$_2$CH$_2$OCH$_2$CH$_2$OCH$_3$ | H | Cl | Cl | threo | rac | m/z 613 |
| 3.96 | F | OCOCH$_2$OCH$_2$CH$_2$OCH$_2$CH$_2$OCH$_3$ | H | CH$_2$OCOCH$_2$OCH$_2$—CH$_2$OCH$_2$CH$_2$OCH$_3$ | H | threo | 2-S, 3-R | m/z 734 |
| 3.97 | F | OCO(4-CN—C$_6$H$_4$) | H | H | H | threo | rac | 212 |
| 3.98 | F | OCO(2,5-Cl$_2$-6-OCH$_3$—C$_6$H$_2$) | H | H | H | threo | rac | 220 |
| 3.99 | F | OCOCH$_2$C$_6$H$_5$ | H | H | H | threo | rac | m/z 502 |
| 3.100 | F | OCOCH$_2$(2-F—C$_6$H$_4$) | H | H | H | threo | rac | m/z 520 |
| 3.101 | F | OCOCH$_2$(4-F—C$_6$H$_4$) | H | H | H | threo | rac | m/z 520 |
| 3.102 | F | OCOCH$_2$(2,4-Cl$_2$—C$_6$H$_3$) | H | H | H | threo | rac | m/z 571 |
| 3.103 | F | OCOCH$_2$(2,6-Cl$_2$—C$_6$H$_3$) | H | H | H | threo | rac | m/z 571 |
| 3.104 | F | OCOCH(OCH$_3$)C$_6$H$_5$ | H | H | H | threo | rac | m/z 532 |
| 3.105 | F | OCOCH$_2$CH$_2$C$_6$H$_5$ | H | H | H | threo | rac | m/z 516 |
| 3.106 | F | OCOCH(CH$_3$)O(2,4-Cl$_2$—C$_6$H$_3$) | H | H | H | threo | rac | 182 |
| 3.107 | F | OCOCH$_2$CH$_2$CH$_2$O(2,4-Cl$_2$—C$_6$H$_3$) | H | H | H | threo | rac | m/z 615 |
| 3.108 | F | OCOCH$_2$CH$_2$CH$_2$O(2-CH$_3$—4-Cl—C$_6$H$_3$) | H | H | H | threo | rac | m/z 595 |
| 3.109 | F | OCOCH$_2$NH$_2$*HCl | H | H | H | threo | rac | 210 |
| 3.110 | F | OCOCH$_2$NHCHO | H | H | H | threo | rac | m/z 469 |
| 3.111 | F | OCOCH$_2$NHCOCH$_2$Cl | H | H | H | threo | rac | m/z 517 |
| 3.112 | F | OCONH(CH$_3$)$_2$ | H | H | OCH$_3$ | threo | 2-S, 3-R | 160 |
| 3.113 | F | OCONH(CH$_3$)$_2$ | H | H | NHCON(CH$_3$)$_2$ | erythro | rac | m/z 541 |
| 3.114 | F | OCONH(CH$_3$)$_2$ | H | OCH$_2$C$_6$H$_5$ | H | threo | 2-S, 3-R | 192 |
| 3.115 | F | OCONH(CH$_3$)$_2$ | H | Cl | Cl | threo | rac | 206 |
| 3.116 | F | OCONH(CH$_3$)$_2$ | H | Cl | CF$_3$ | threo | rac | 230 |
| 3.117 | F | OCON(CH$_3$)$_2$ | H | H | H | erythro | rac | 220 |
| 3.118 | F | OCON(CH$_3$)$_2$ | H | H | F | threo | 2-S, 3-R | 187 |
| 3.119 | F | OCON(CH$_3$)$_2$ | H | H | CF$_3$ | threo | rac | 135 |
| 3.120 | F | OCON(CH$_3$)$_2$ | H | H | NO$_2$ | erythro | rac | m/z 430 |
| 3.121 | F | OCON(CH$_3$)$_2$ | H | H | NO$_2$ | threo | rac | 216 |
| 3.122 | F | OCON(CH$_3$)$_2$ | H | H | NH$_2$ | erythro | rac | 216 |
| 3.123 | F | OCON(CH$_3$)$_2$ | H | H | NH$_2$ | threo | rac | 213 |
| 3.124 | F | OCON(CH$_3$)$_2$ | H | H | NHCOCH$_3$ | erythro | rac | m/Z 512 |
| 3.125 | F | OCON(CH$_3$)$_2$ | H | H | NHCONHSO$_2$CF$_3$ | erythro | rac | 166 |
| 3.126 | F | OCON(CH$_3$)$_2$ | H | H | NHCONHSO$_2$CF$_3$ | threo | rac | 168 |
| 3.127 | F | OCON(CH$_3$)$_2$ | H | H | NHSO$_2$CH$_3$ | erythro | rac | 212 |
| 3.128 | F | OCON(CH$_3$)$_2$ | H | H | NHSO$_2$CH$_3$ | threo | rac | m/z 548 |

TABLE 3-continued

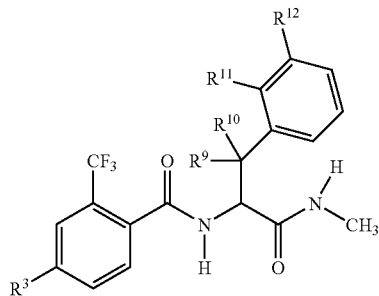

where $R^1 = CF_3$, $R^2$, $R^4$, $R^5$, $R^6$, $R^7 = H$,
$R^8 = CH_3$, $R^{13}$, $R^{14}$, $R^{15} = H$

| No. | $R^3$ | $R^9$ | $R^{10}$ | $R^{11}$ | $R^{12}$ | erthro/threo | Config. | m.p. or m/z |
|---|---|---|---|---|---|---|---|---|
| 3.129 | F | OCON(CH$_3$)$_2$ | H | H | NHSO$_2$CF$_3$ | erythro | rac | m/z 602 |
| 3.130 | F | OCON(CH$_3$)$_2$ | H | Cl | H | threo | rac | 165 |
| 3.131 | F | OCON(CH$_3$)$_2$ | H | CH$_2$OCON(CH$_3$)$_2$ | H | threo | 2-S, 3-R | 93 |
| 3.132 | F | OCONCH$_3$C$_6$H$_5$ | H | H | H | threo | rac | 178 |
| 3.133 | F | OCONHSO$_2$CF$_3$ | H | H | H | erythro | rac | m/z 559 |
| 3.134 | F | OCONHSO$_2$CF$_3$ | H | H | H | threo | rac | 174 |
| 3.135 | F | NHCONHSO$_2$CF$_3$ | H | H | H | threo | rac | m/z 574 |
| 3.136 | F | OCONHSO$_2$CF$_3$ | H | H | F | threo | 2-S, 3-R | 165 |
| 3.137 | F | OCONHSO$_2$CF$_3$ | H | CH$_3$ | F | threo | 2-S, 3-R | 170 |
| 3.138 | F | OCONHSO$_2$(2-Cl—C$_6$H$_4$) | H | H | H | threo | rac | 206 |
| 3.139 | F | OCONHSO$_2$(4-CH$_3$—C$_6$H$_4$) | H | H | H | threo | rac | 202 |
| 3.140 | F | OCONHSO$_2$(2-CF$_3$—C$_6$H$_4$) | H | H | H | threo | rac | 200 |
| 3.141 | F | O-[4,6-(OCH$_3$)$_2$-2-pyrimidyl] | H | H | H | threo | rac | 218 |
| 3.142 | F | OCO[2,2-(CH$_3$)-4-dioxolanyl] | H | H | H | threo | rac | m/z 512 |
| 3.143 | F | OCO(4-pyranyl) | H | H | H | threo | rac | m/z 496 |
| 3.144 | F | OCO-(3,6-Cl$_2$-2-pyridyl) | H | H | H | threo | rac | 210 |
| 3.145 | F | OCOCH$_2$(2-thienyl) | H | H | H | threo | rac | m/z 508 |
| 3.146 | F | OCOCH$_2$(3-thienyl) | H | H | H | threo | rac | m/z 508 |
| 3.147 | F | OCOCH$_2$(1-pyrazolyl) | H | H | H | threo | rac | m/z 492 |
| 3.148 | F | OCOCH$_2$(1-triazolyl) | H | H | H | threo | rac | m/z 493 |
| 3.149 | F | OCOCH$_2$(3-pyridyl) | H | H | H | threo | rac | m/z 503 |
| 3.150 | F | OCOCH$_2$CH$_2$(4-morpholinyl) | H | H | H | threo | rac | m/z 525 |
| 3.151 | F | OCOCHClCH$_2$(1-triazolyl) | H | H | H | threo | rac | 146 |
| 3.152 | F | OSi(CH$_2$CH$_3$)$_3$ | H | CH$_2$OSi(CH$_2$CH$_3$)$_3$ | H | threo | 2-S, 3-R | m/z 642 |
| 3.153 | F | OSi(CH$_2$CH$_3$)$_3$ | H | H | Br | threo | 2-S, 3-R | 75 |
| 3.154 | F | OSi(CH$_3$)$_2$C(CH$_3$)$_3$ | H | H | H | threo | rac | 139 |
| 3.155 | F | OSi(CH$_3$)$_2$C(CH$_3$)$_3$ | H | CH$_2$F | H | threo | 2-S, 3-R | 80 |
| 3.156 | F | OSi(CH$_3$)$_2$C(CH$_3$)$_3$ | H | CH$_2$OH | H | threo | 2-S, 3-R | m/z 528 |
| 3.157 | F | OSO$_2$CH$_3$ | H | Cl | H | threo | rac | 127 |
| 3.158 | F | OSO$_2$CH$_3$ | H | Cl | Cl | threo | rac | 148 |
| 3.159 | F | NH$_2$ | H | H | H | 4:1 | rac | 168 |
| 3.160 | F | NHCH$_3$ | H | CH$_2$OH | H | threo | 2-S, 3-R | 192 |
| 3.161 | F | NHCH$_2$C$_6$H$_5$ | H | H | H | 4:1 | rac | 186 |
| 3.162 | F | NHCOCH$_3$ | H | H | H | 4:1 | rac | oil |
| 3.163 | F | NHCOC(CH$_3$)$_3$ | H | H | H | 4:1 | rac | 222 |
| 3.164 | F | NHCOOC(CH$_3$)$_3$ | H | H | H | 4:1 | rac | m/z 483 |
| 3.165 | F | NHCON(CH$_3$)$_2$ | H | H | H | 4:1 | rac | 198 |
| 3.166 | F | NCH$_3$CON(CH$_3$)$_2$ | H | CH$_2$OCON(CH$_3$)$_2$ | H | threo | 2-S, 3-R | 190 |

TABLE 4

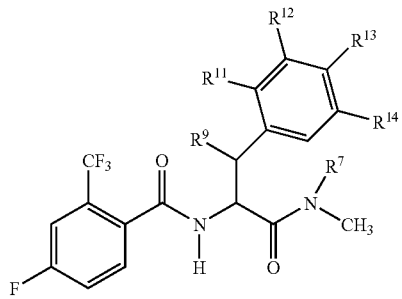

where $R^1 = CF_3$, $R^2 = H$, $R^3 = F$,
$R^4, R^5, R^6 = H$, $R^8 = CH_3$,
$R^{10}, R^{15} = H$

| No. | $R^7$ | $R^9$ | $R^{11}$ | $R^{12}$ | $R^{13}$ | $R^{14}$ | erythro/threo | Config. | m.p. or m/z |
|---|---|---|---|---|---|---|---|---|---|
| 4.1 | H | OH | H | H | F | H | threo | 2-S, 3-R | 149 |
| 4.2 | H | OH | H | H | $CF_3$ | H | threo | rac | 180 |
| 4.3 | H | OH | H | H | $SCH_3$ | H | threo | rac | 185 |
| 4.4 | H | OH | H | H | $NO_2$ | H | threo | rac | 212 |
| 4.5 | H | OH | H | H | $OCH_2C_6H_5$ | H | threo | 2-S, 3-R | 197 |
| 4.6 | H | OH | H | Br | F | H | erythro | rac | 175 |
| 4.7 | H | OH | H | Br | F | H | threo | rac | 192 |
| 4.8 | H | OH | Cl | H | F | H | threo | rac | 160 |
| 4.9 | H | OH | Cl | Cl | H | H | threo | rac | 187 |
| 4.10 | H | OH | Cl | H | Cl | H | threo | rac | 160 |
| 4.11 | H | OH | $CH_3$ | H | F | H | threo | 2-S, 3-R | m/z 416 |
| 4.12 | H | OH | $CF_3$ | H | F | H | threo | rac | 140 |
| 4.13 | H | OH | Cl | H | H | Cl | threo | rac | 214 |
| 4.14 | H | OH | H | F | H | F | threo | rac | 176 |
| 4.15 | H | OH | F | F | F | H | threo | 2-S, 3-R | 166 |
| 4.16 | H | $OCOCH_3$ | H | H | F | H | threo | 2-S, 3-R | 152 |
| 4.17 | H | $OCOCH_3$ | H | H | $CF_3$ | H | threo | rac | 217 |
| 4.18 | H | $OCOCH_3$ | Cl | H | F | H | threo | rac | 180 |
| 4.19 | H | $OCOCH_3$ | Cl | H | Cl | H | threo | rac | 190 |
| 4.20 | H | $OCOCH_3$ | H | Br | F | H | threo | rac | 200 |
| 4.21 | H | $OCOCH_3$ | H | F | H | F | threo | rac | 155 |
| 4.22 | H | $OCOC(CH_3)_3$ | H | H | F | H | threo | 2-S, 3-R | 159 |
| 4.23 | H | $OCOCH_2OCH_2CH_2OCH_2CH_2OCH_3$ | H | Br | F | H | threo | rac | m/z 641 |
| 4.24 | H | $OCOCH_2OCH_2CH_2OCH_2CH_2OCH_3$ | F | F | F | H | threo | 2-S, 3-R | 111 |
| 4.25 | H | $OCON(CH_3)_2$ | H | H | F | H | threo | 2-S, 3-R | 156 |
| 4.26 | H | $OCON(CH_3)_2$ | H | H | $CF_3$ | H | threo | rac | 190 |
| 4.27 | H | $OCON(CH_3)_2$ | H | H | $SCH_3$ | H | threo | rac | m/z 501 |
| 4.28 | H | $OCON(CH_3)_2$ | Cl | H | F | H | threo | rac | 203 |
| 4.29 | H | $OCON(CH_3)_2$ | Cl | H | Cl | H | threo | rac | 192 |
| 4.30 | H | $OCON(CH_3)_2$ | H | Br | F | H | threo | rac | 165 |
| 4.31 | H | $OCON(CH_3)_2$ | H | F | H | F | threo | rac | 203 |
| 4.32 | H | $OCON(CH_3)_2$ | F | F | F | H | threo | 2-S, 3-R | 152 |
| 4.33 | H | $OSO_2CH_3$ | Cl | H | F | H | threo | rac | 112 |
| 4.34 | H | $OSO_2CH_3$ | H | F | H | F | threo | rac | 150 |
| 4.35 | H | OH | Cl | H | H | $CF_3$ | threo | rac | 172 |
| 4.36 | H | $OCOCH_3$ | Cl | H | H | Cl | threo | rac | 195 |
| 4.37 | H | $OSO_2CH_3$ | Cl | H | H | Cl | threo | rac | 140 |
| 4.38 | H | $OCON(CH_3)_2$ | Cl | H | H | Cl | threo | rac | 192 |
| 4.39 | H | $OCON(CH_3)_2$ | Cl | H | H | $CF_3$ | threo | rac | 188 |
| 4.40 | OH | $OSi(CH_3)_2C(CH_3)_3$ | H | H | H | H | threo | 2-S, 3-R | m/z 514 |

TABLE 5

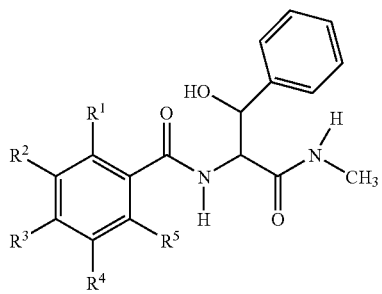

I where $R^6, R^7 = H, R^8 = CH_3, R^9 = OH,$
$R^{10}, R^{11}, R^{12}, R^{13}, R^{14}, R^{15} = H$

| No. | $R^1$ | $R^2$ | $R^3$ | $R^4$ | $R^5$ | erythro/threo | Config. | m.p. or m/z |
|---|---|---|---|---|---|---|---|---|
| 5.1 | F | H | F | H | H | threo | rac | m/z 334 |
| 5.2 | F | H | CF$_3$ | H | H | threo | rac | m/z 384 |
| 5.3 | F | H | H | F | H | threo | rac | m/z 334 |
| 5.4 | F | H | H | H | F | threo | rac | m/z 334 |
| 5.5 | F | H | H | H | Cl | threo | rac | m/z 350 |
| 5.6 | F | F | H | H | F | threo | rac | m/z 352 |
| 5.7 | F | F | H | F | F | threo | rac | m/z 370 |
| 5.8 | Cl | H | H | H | H | threo | rac | m/z 332 |
| 5.9 | Cl | Cl | H | H | H | threo | rac | m/z 367 |
| 5.10 | Cl | CF$_3$ | H | H | H | threo | rac | 167 |
| 5.11 | Cl | NO$_2$ | H | H | H | threo | rac | m/z 377 |
| 5.12 | Cl | H | Cl | H | H | threo | rac | m/z 367 |
| 5.13 | Cl | H | NO$_2$ | H | H | threo | rac | m/z 377 |
| 5.14 | Cl | H | H | Cl | H | threo | rac | m/z 367 |
| 5.15 | Cl | H | Cl | Cl | H | threo | rac | m/z 401 |
| 5.16 | Cl | H | COOCH$_3$ | Cl | H | threo | rac | m/z 425 |
| 5.17 | Cl | NO$_2$ | Cl | NO$_2$ | H | threo | rac | m/z 457 |
| 5.18 | CH$_3$ | H | H | H | H | threo | rac | m/z 312 |
| 5.19 | CH$_3$ | C(CH$_2$)(CH$_3$) | H | H | H | threo | rac | m/z 352 |
| 5.20 | CH$_3$ | NO$_2$ | H | H | H | threo | rac | m/z 357 |
| 5.21 | CH$_3$ | H | H | H | CH$_3$ | threo | rac | m/z 326 |
| 5.22 | CH$_3$ | H | H | H | NO$_2$ | threo | rac | m/z 357 |
| 5.23 | CH$_3$ | NO$_2$ | H | NO$_2$ | H | threo | rac | m/z 402 |
| 5.24 | CF$_3$ | F | H | H | H | threo | rac | 158 |
| 5.25 | CF$_3$ | Cl | H | H | H | threo | rac | m/z 400 |
| 5.26 | NO$_2$ | H | H | H | H | threo | rac | m/z 343 |
| 5.27 | NO$_2$ | Cl | H | H | H | threo | rac | m/z 377 |
| 5.28 | NO$_2$ | H | Cl | H | H | threo | rac | m/z 377 |
| 5.29 | OCH$_3$ | H | SCH$_3$ | H | H | threo | rac | m/z 374 |
| 5.30 | OCH$_3$ | H | H | Cl | H | threo | rac | m/z 362 |
| 5.31 | OCH$_3$ | H | H | OCH$_3$ | H | threo | rac | m/z 358 |
| 5.32 | OCH$_3$ | OCH$_3$ | OCH$_3$ | H | H | threo | rac | m/z 388 |
| 5.33 | OCH$_2$CH$_3$ | OCH$_2$CH$_3$ | OCH$_2$CH$_3$ | H | H | threo | rac | m/z 430 |
| 5.34 | COOH | H | F | H | H | threo | rac | 216 |
| 5.35 | C$_6$H$_5$ | H | H | H | H | threo | rac | m/z 374 |
| 5.36 | OCF$_3$ | H | H | H | H | threo | rac | m/z 382 |
| 5.37 | SCHF$_2$ | H | H | H | H | threo | rac | m/z 380 |

Biological Activity

The benzoyl-substituted phenylalanineamides of the formula I and their agriculturally useful salts are suitable, both in the form of isomer mixtures and in the form of the pure isomers, as herbicides. The herbicidal compositions comprising compounds of the formula I control vegetation on noncrop areas very efficiently, especially at high rates of application. They act against broad-leaved weeds and grass weeds in crops such as wheat, rice, corn, soya and cotton without causing any significant damage to the crop plants. This effect is mainly observed at low rates of application.

Depending on the application method in question, the compounds of the formula I, or herbicidal compositions comprising them, can additionally be employed in a further number of crop plants for eliminating undesirable plants. Examples of suitable crops are the following:

*Allium cepa, Ananas comosus, Arachis hypogaea, Asparagus officinalis, Beta vulgaris* spec. *altissima, Beta vulgaris* spec. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max, Gossypium hirsutum,* (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus* spec., *Manihot esculenta, Medicago sativa, Musa* spec., *Nicotiana tabacum* (*N. rustica*), *Olea europaea, Oryza sativa, Phaseolus lunatus, Phaseolus vulgaris, Picea abies, Pinus* spec., *Pisum sativum,*

*Prunus avium, Prunus persica, Pyrus communis, Ribes sylvestre, Ricinus communis, Saccharum officinarum, Secale cereale, Solanum tuberosum, Sorghum bicolor* (*s. vulgare*), *Theobroma cacao, Trifolium pratense, Triticum aestivum, Triticum durum, Vicia faba, Vitis vinifera* and *Zea mays*.

In addition, the compounds of the formula I may also be used in crops which tolerate the action of herbicides owing to breeding, including genetic engineering methods.

The compounds of the formula I, or the herbicidal compositions comprising them, can be used for example in the form of ready-to-spray aqueous solutions, powders, suspensions, also highly concentrated aqueous, oily or other suspensions or dispersions, emulsions, oil dispersions, pastes, dusts, materials for broadcasting, or granules, by means of spraying, atomizing, dusting, spreading or watering. The use forms depend on the intended purpose; in any case, they should guarantee the finest possible distribution of the active ingredients according to the invention.

The herbicidal compositions comprise a herbicidally effective amount of at least one compound of the formula I or an agriculturally useful salt of I, and auxiliaries which are customary for the formulation of crop protection agents.

Suitable as inert auxiliaries are essentially the following:

mineral oil fractions of medium to high boiling point, such as kerosene and diesel oil, furthermore coal tar oils and oils of vegetable or animal origin, aliphatic, cyclic and aromatic hydrocarbons, e.g. paraffin, tetrahydronaphthalene, alkylated naphthalenes and their derivatives, alkylated benzenes and their derivatives, alcohols such as methanol, ethanol, propanol, butanol and cyclohexanol, ketones such as cyclohexanone, strongly polar solvents, e.g. amines such as N-methylpyrrolidone, and water.

Aqueous use forms can be prepared from emulsion concentrates, suspensions, pastes, wettable powders or water-dispersible granules by adding water. To prepare emulsions, pastes or oil dispersions, the substrates, either as such or dissolved in an oil or solvent, can be homogenized in water by means of a wetting agent, tackifier, dispersant or emulsifier. Alternatively, it is also possible to prepare concentrates comprising active substance, wetting agent, tackifier, dispersant or emulsifier and, if desired, solvent or oil, which are suitable for dilution with water.

Suitable surfactants (adjuvants) are the alkali metal salts, alkaline earth metal salts and ammonium salts of aromatic sulfonic acids, e.g. ligno-, phenol-, naphthalene- and dibutylnaphthalenesulfonic acid, and of fatty acids, alkyl- and alkylarylsulfonates, alkyl sulfates, lauryl ether sulfates and fatty alcohol sulfates, and salts of sulfated hexa-, hepta- and octadecanols, and also of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ether, ethoxylated isooctyl-, octyl- or nonylphenol, alkylphenyl or tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors or methylcellulose.

Powders, materials for broadcasting and dusts can be prepared by mixing or grinding the active ingredients together with a solid carrier.

Granules, e.g. coated granules, impregnated granules and homogeneous granules, can be prepared by binding the active ingredients to solid carriers. Solid carriers are mineral earths such as silicas, silica gels, silicates, talc, kaolin, limestone, lime, chalk, bole, loess, clay, dolomite, diatomaceous earth, calcium sulfate, magnesium sulfate and magnesium oxide, ground synthetic materials, fertilizers such as ammonium sulfate, ammonium phosphate, ammonium nitrate and ureas, and products of vegetable origin, such as cereal meal, tree bark meal, wood meal and nutshell meal, cellulose powders, or other solid carriers.

The concentrations of the compounds of the formula I in the ready-to-use preparations can be varied within wide ranges. In general, the formulations comprise approximately from 0.001 to 98% by weight, preferably 0.01 to 95% by weight of at least one active ingredient. The active ingredients are employed in a purity of from 90% to 100%, preferably 95% to 100% (according to NMR spectrum).

The formulation examples below illustrate the preparation of such compositions:

I. 20 parts by weight of an active compound of the formula I are dissolved in a mixture composed of 80 parts by weight of alkylated benzene, 10 parts by weight of the adduct of from 8 to 10 mol of ethylene oxide to 1 mol of oleic acid N-monoethanolamide, 5 parts by weight of calcium dodecylbenzenesulfonate and 5 parts by weight of the adduct of 40 mol of ethylene oxide to 1 mol of castor oil. Pouring the solution into 100 000 parts by weight of water and finely distributing it therein gives an aqueous dispersion which comprises 0.02% by weight of the active ingredient of the formula I.

II. 20 parts by weight of an active compound of the formula I are dissolved in a mixture composed of 40 parts by weight of cyclohexanone, 30 parts by weight of isobutanol, 20 parts by weight of the adduct of 7 mol of ethylene oxide to 1 mol of isooctylphenol and 10 parts by weight of the adduct of 40 mol of ethylene oxide to 1 mol of castor oil. Pouring the solution into 100 000 parts by weight of water and finely distributing it therein gives an aqueous dispersion which comprises 0.02% by weight of the active ingredient of the formula I.

III. 20 parts by weight of an active compound of the formula I are dissolved in a mixture composed of 25 parts by weight of cyclohexanone, 65 parts by weight of a mineral oil fraction of boiling point 210 to 280° C. and 10 parts by weight of the adduct of 40 mol of ethylene oxide to 1 mol of castor oil. Pouring the solution into 100 000 parts by weight of water and finely distributing it therein gives an aqueous dispersion which comprises 0.02% by weight of the active ingredient of the formula I.

IV. 20 parts by weight of an active compound of the formula I are mixed thoroughly with 3 parts by weight of sodium diisobutylnaphthalenesulfonate, 17 parts by weight of the sodium salt of a lignosulfonic acid from a sulfite waste liquor and 60 parts by weight of pulverulent silica gel, and the mixture is ground in a hammer mill. Finely distributing the mixture in 20 000 parts by weight of water gives a spray mixture which comprises 0.1% by weight of the active ingredient of the Formula I.

V. 3 parts by weight of an active compound of the formula I are mixed with 97 parts by weight of finely divided kaolin. This gives a dust which comprises 3% by weight of the active ingredient of the formula I.

VI. 20 parts by weight of an active compound of the formula I are mixed intimately with 2 parts by weight of calcium dodecylbenzenesulfonate, 8 parts by weight of fatty alcohol polyglycol ether, 2 parts by weight of the sodium salt of a phenol/urea/formaldehyde condensate and 68 parts by weight of a paraffinic mineral oil. This gives a stable oily dispersion.

VII. 1 part by weight of an active compound of the formula I is dissolved in a mixture composed of 70 parts by weight of cyclohexanone, 20 parts by weight of ethoxylated isooctylphenol and 10 parts by weight of ethoxylated castor oil. This gives a stable emulsion concentrate.

VIII. 1 part by weight of an active compound of the formula I is dissolved in a mixture composed of 80 parts by weight of cyclohexanone and 20 parts by weight of Wettol® EM 31 (=nonionic emulsifier based on ethoxylated castor oil). This gives a stable emulsion concentrate.

The compounds of the formula I or the herbicidal compositions can be applied pre- or post-emergence. If the active ingredients are less well tolerated by certain crop plants, application techniques may be used in which the herbicidal compositions are sprayed, with the aid of the spraying equipment, in such a way that as far as possible they do not come into contact with the leaves of the sensitive crop plants, while the active ingredients reach the leaves of undesirable plants growing underneath, or the bare soil surface (post-directed, lay-by).

The rates of application of the compound of the formula I are from 0.001 to 3.0, preferably 0.01 to 1.0, kg/ha of active substance (a.s.), depending on the control target, the season, the target plants and the growth stage.

To widen the spectrum of action and to achieve synergistic effects, the benzoyl-substituted phenylalanineamides of the formula I may be mixed with a large number of representatives of other herbicidal or growth-regulating active ingredient groups and then applied concomitantly. Suitable components for mixtures are, for example, 1,2,4-thiadiazoles, 1,3,4-thiadiazoles, amides, aminophosphoric acid and its derivatives, aminotriazoles, anilides, (het)aryloxyalkanoic acids and their derivatives, benzoic acid and its derivatives, benzothiadiazinones, 2-(het)aroyl-1,3-cyclohexanediones, hetaryl aryl ketones, benzylisoxazolidinones, meta-CF$_3$-phenyl derivatives, carbamates, quinolinecarboxylic acid and its derivatives, chloroacetanilides, cyclohexenone oxime ether derivatives, diazines, dichloropropionic acid and its derivatives, dihydrobenzofurans, dihydrofuran-3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4,5,6-tetrahydrophthalimides, oxadiazoles, oxiranes, phenols, aryloxy- and hetaryloxyphenoxypropionic esters, phenylacetic acid and its derivatives, 2-phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazolecarboxamides and uracils.

It may furthermore be beneficial to apply the compounds of the formula I alone or in combination with other herbicides, or in the form of a mixture with other crop protection agents, for example together with agents for controlling pests or phytopathogenic fungi or bacteria. Also of interest is the miscibility with mineral salt solutions, which are employed for treating nutritional and trace element deficiencies. Non-phytotoxic oils and oil concentrates may also be added.

USE EXAMPLES

The herbicidal activity of the benzoyl-substituted phenylalanineamides of the formula I was demonstrated by the following greenhouse experiments:

The culture containers used were plastic flowerpots containing loamy sand with approximately 3.0% of humus as the substrate. The seeds of the test plants were sown separately for each species.

For the pre-emergence treatment, the active ingredients, which had been suspended or emulsified in water, were applied directly after sowing by means of finely distributing nozzles. The containers were irrigated gently to promote germination and growth and subsequently covered with transparent plastic hoods until the plants had rooted. This cover causes uniform germination of the test plants, unless this has been impaired by the active ingredients.

For the post-emergence treatment, the test plants were first grown to a height of 3 to 15 cm, depending on the plant habit, and only then treated with the active ingredients which had been suspended or emulsified in water. For this purpose, the test plants were either sown directly and grown in the same containers, or they were first grown separately as seedlings and transplanted into the test containers a few days prior to treatment. The rate of application for the post-emergence treatment was 1.0, 0.5, 0.25, 0.125 or 0.0625 kg/ha of a.s. (active substance).

Depending on the species, the plants were kept at 10-25° C. or 20-35° C. The test period extended over 2 to 4 weeks. During this time, the plants were tended, and their response to the individual treatments was evaluated.

Evaluation was carried out using a scale from 0 to 100. 100 means no emergence of the plants, or complete destruction of at least the aerial parts, and 0 means no damage, or normal course of growth.

The plants used in the greenhouse experiments belonged to the following species:

| Scientific Name | Common Name |
| --- | --- |
| Abutilon theophrasti | velvet leaf |
| Amaranthus retroflexus | pig weed |
| Avena fatua | wild oat |
| Chenopodium album | lambsquarters |
| Galium aparine | cleavers harrif |
| Polygonum convolvulus | black bindweed |
| Setaria viridis | green foxtail |

At application rates of 1.00 kg/ha, the compounds 3.2, 3.10, 3.11 and 3.28 (Table 3) showed very good post-emergence action against the unwanted plants pig weed, lambsquarters and green foxtail.

Furthermore, compounds 3.66, 3.67 and 3.128 (Table 3), applied by the post-emergence method, effected, at application rates of 1.00 kg/ha, very good control of the harmful plants pig weed, lambsquarters and green foxtail.

Furthermore, compounds 3.96, 3.61 and 3.131 (Table 3) effected very good post-emergence control of the harmful plants pig weed, lambsquarters, cleavers harrif and black bindweed at application rates of 0.5 kg/ha.

The post-emergence action of compound 3.65 (Table 3) at application rates of 0.5 kg/ha on the weeds pig weed, lambsquarters and black bindweed was very good.

At application rates of 0.5 kg/ha, the compounds 3.62 (Table 3) and 4.24 (Table 4) showed very good post-emergence action against the unwanted plants pig weed, lambsquarters, cleavers harrif and green foxtail.

Furthermore, compound 3.152 (Table 3) effected very good post-emergence control of the harmful plants pig weed, lambsquarters, cleavers harrif and green foxtail at application rates of 1.0 kg/ha.

At application rates of 1.00 kg/ha, the action of compounds 3.123 and 3.137 (Table 3), applied by the post-emergence method, on the weeds pig weed, lambsquarters and black bindweed was very good.

Likewise, the compound 3.154 (Table 3) effected, at application rates of 1.0 kg/ha, very good post-emergence control of the unwanted plants pig weed, lambsquarters, cleavers harrif, black bindweed and green foxtail.

At application rates of 0.5 kg/ha, the compound 5.20 (Table 5) had very good post-emergence action on the weed velvet leaf.

At application rates of 0.5 kg/ha, the compound 5.36 (Table 5) showed very good post-emergence action against the unwanted plant velvet leaf.

Furthermore, compound 5.37 (Table 5) controlled the harmful plants velvet leaf and wild oat when applied by the post-emergence method at application rates of 0.5 kg/ha.

We claim:

1. A benzoyl-substituted phenylalanineamide of the formula I

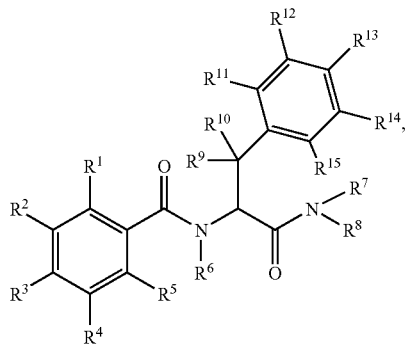

in which the variables are as defined below:
$R^1$ is halogen, cyano, $C_1$-$C_6$-alkyl, $C_1$-$C_6$-haloalkyl, $C_1$-$C_6$-haloalkoxy, nitro, hydroxycarbonyl, $C_1$-$C_6$-alkoxycarbonyl, or $C_1$-$C_6$-haloalkylthio;

$R^2$, $R^4$, $R^5$ are hydrogen, halogen, cyano, $C_1$-$C_6$-alkyl, $C_1$-$C_6$-haloalkyl, $C_1$-$C_6$-alkoxy, $C_1$-$C_6$-haloalkoxy, amino, $C_1$-$C_6$-alkylamino, di($C_1$-$C_6$-alkyl)amino, $C_1$-$C_6$-alkylthio or $C_1$-$C_6$-alkoxycarbonyl;

$R^3$ is hydrogen, halogen, cyano, $C_1$-$C_6$-alkyl, $C_1$-$C_6$-haloalkyl, $C_1$-$C_6$-alkoxy, nitro, amino, $C_1$-$C_6$-alkylamino, di($C_1$-$C_6$-alkyl)amino, $C_1$-$C_6$-alkylthio or $C_1$-$C_6$-alkoxycarbonyl;

$R^6$, $R^7$ are hydrogen, or hydroxyl;

$R^8$ is $C_1$-$C_6$-alkyl, $C_1$-$C_4$-cyanoalkyl or $C_1$-$C_6$-haloalkyl;

$R^9$ is $OR^{16}$, $SR^{17}$ or $NR^{18}R^{19}$;

$R^{10}$ is hydrogen or $C_1$-$C_6$-alkyl;

$R^{11}$, $R^{12}$ are hydrogen, halogen, cyano, $C_1$-$C_6$-alkyl, $C_1$-$C_6$-haloalkyl, hydroxyl, $C_1$-$C_6$-alkoxy, $C_1$-$C_6$-haloalkoxy, hydroxyl, nitro, hydroxy-$C_1$-$C_4$-alkyl, $C_1$-$C_6$-alkoxy-$C_1$-$C_4$-alkyl, tri($C_1$-$C_6$-alkyl)silyloxy-$C_1$-$C_4$-alkyl, $C_1$-$C_4$-alkylthio, (hydroxycarbonyl)-$C_1$-$C_6$-alkyl, ($C_1$-$C_6$-alkoxycarbonyl)-$C_1$-$C_6$-alkyl, (hydroxycarbonyl)-$C_2$-$C_6$-alkenyl, ($C_1$-$C_6$-alkoxycarbonyl)-$C_2$-$C_6$-alkenyl, (hydroxycarbonyl)-$C_1$-$C_4$-alkoxy, ($C_1$-$C_4$-alkoxycarbonyl)-$C_1$-$C_4$-alkoxy, ($C_1$-$C_4$-alkylcarbonyl)oxy-$C_1$-$C_4$-alkyl, hydroxycarbonyl-$C_1$-$C_4$-alkoxy-$C_1$-$C_4$-alkyl, ($C_1$-$C_4$-alkylsulfonyl)oxy-$C_1$-$C_4$-alkyl, $C_1$-$C_4$-alkyl-O—C(O)-[$C_1$-$C_4$-alkyl-O]$_3$—$C_1$-$C_4$-alkyl, carbamoyloxy-$C_1$-$C_4$-alkyl, ($C_1$-$C_4$-alkylamino carbonyl)oxy-$C_1$-$C_4$-alkyl, [di($C_1$-$C_4$-alkyl)aminocarbonyl]oxy-$C_1$-$C_4$-alkyl, [($C_1$-$C_4$-haloalkylsulfonyl)aminocarbonyl]oxy-$C_1$-$C_4$-alkyl, benzyloxy, where the phenyl ring may be substituted by 1 to 3 radicals from the group consisting of halogen and $C_1$-$C_4$-alkyl, amino, $C_1$-$C_4$-alkylamino, di($C_1$-$C_4$-alkyl) amino, ($C_1$-$C_4$-alkylsulfonyl)-amino, $C_1$-$C_4$-(haloalkylsulfonyl)amino, ($C_1$-$C_4$-alkylcarbonyl)amino, carbamoylamino, ($C_1$-$C_4$-alkylamino)carbonylamino, [di($C_1$-$C_4$-alkyl)amino]carbonylamino, [($C_1$-$C_4$-haloalkylsulfonyl)aminocarbonyl]-amino, phenyl or heterocyclyl, where the phenyl and the heterocyclyl radical of the two last-mentioned substituents may carry one to three radicals from the following group: halogen, nitro, $C_1$-$C_4$-alkyl, $C_1$-$C_4$-haloalkyl, hydroxycarbonyl and $C_1$-$C_6$-alkoxycarbonyl;

$R^{13}$, $R^{14}$, $R^{15}$ are hydrogen, halogen, cyano, $C_1$-$C_6$-alkyl, $C_1$-$C_6$-haloalkyl, $C_1$-$C_6$-alkoxy, $C_1$-$C_6$-haloalkoxy, nitro, hydroxyl, $C_1$-$C_4$-alkylthio or benzyloxy;

$R^{16}$, $R^{17}$, $R^{18}$ are hydrogen, $C_1$-$C_6$-alkyl, tri($C_1$-$C_6$-alkyl) silyl, $C_3$-$C_6$-cycloalkyl, $C_3$-$C_6$-alkenyl, $C_3$-$C_6$-alkynyl, $C_3$-$C_6$-haloalkenyl, $C_3$-$C_6$-haloalkynyl, formyl, $C_1$-$C_6$-alkylcarbonyl, $C_3$-$C_6$-cycloalkylcarbonyl, $C_2$-$C_6$-alkenylcarbonyl, $C_2$-$C_6$-alkynylcarbonyl, $C_1$-$C_6$-alkoxycarbonyl, $C_3$-$C_6$-alkenyloxycarbonyl, $C_3$-$C_6$-alkynyloxycarbonyl, $C_1$-$C_6$-alkylaminocarbonyl, $C_3$-$C_6$-alkenylaminocarbonyl, $C_3$-$C_6$-alkynylaminocarbonyl, $C_1$-$C_6$-alkylsulfonylaminocarbonyl, $C_1$-$C_6$-haloalkylsulfonylaminocarbonyl, di($C_1$-$C_6$-alkyl)aminocarbonyl, N—($C_1$-$C_6$-alkenyl)-N—($C_1$-$C_6$-alkyl)aminocarbonyl, N—($C_3$-$C_6$-alkynyl)-N—($C_1$-$C_6$-alkyl)aminocarbonyl, N—($C_1$-$C_6$-alkoxy)-N—($C_1$-$C_6$-alkyl)aminocarbonyl, N—($C_3$-$C_6$-alkenyl)-N—($C_1$-$C_6$-alkoxy)aminocarbonyl, N—($C_3$-$C_6$-alkynyl)-N—($C_1$-$C_6$-alkoxy)aminocarbonyl, di($C_1$-$C_6$-alkyl) aminothiocarbonyl, $C_1$-$C_6$-alkylcarbonyl-$C_1$-$C_6$-alkyl, $C_1$-$C_6$-alkoxyimino-$C_1$-$C_6$-alkyl, N—($C_1$-$C_6$-alkylamino)imino-$C_1$-$C_6$-alkyl or N-(di-$C_1$-$C_6$-alkylamino) imino-$C_1$-$C_6$-alkyl, where the alkyl, cycloalkyl and alkoxy radicals mentioned may be partially or fully halogenated and/or may carry one to three of the following groups: cyano, hydroxyl, $C_3$-$C_6$-cycloalkyl, $C_1$-$C_4$-alkoxy, $C_1$-$C_4$-alkylthio, di($C_1$-$C_4$-alkyl)amino, $C_1$-$C_4$-alkylcarbonyl, hydroxycarbonyl, $C_1$-$C_4$-alkoxycarbonyl, aminocarbonyl, $C_1$-$C_4$-alkylaminocarbonyl, di($C_1$-$C_4$-alkyl)-aminocarbonyl or $C_1$-$C_4$-alkylcarbonyloxy;

phenyl, phenyl-$C_1$-$C_6$-alkyl, phenylcarbonyl, phenylcarbonyl-$C_1$-$C_6$-alkyl, phenoxycarbonyl, phenylaminocarbonyl, phenylsulfonylaminocarbonyl, N—($C_1$-$C_6$-alkyl)-N-(phenyl)aminocarbonyl, phenyl-$C_1$-$C_6$-alkylcarbonyl, heterocyclyl, heterocyclyl-$C_1$-$C_6$-alkyl, heterocyclylcarbonyl, heterocyclylcarbonyl-$C_1$-$C_6$-alkyl, heterocyclyloxycarbonyl, heterocyclylaminocarbonyl, heterocyclylsulfonylaminocarbonyl, N—($C_1$-$C_6$-alkyl)-N-(heterocyclyl)aminocarbonyl or heterocyclyl-$C_1$-$C_6$-alkylcarbonyl, where the phenyl and the heterocyclyl radicals may be partially or fully halogenated and/or may carry one to three of the following groups: nitro, cyano, $C_1$-$C_4$-alkyl, $C_1$-$C_4$-haloalkyl, $C_1$-$C_4$-alkoxy or $C_1$-$C_4$-haloalkoxy $SO_2R^{20}$; —C(O)—[$C_1$-$C_4$-alkyl-O]$_3$—$C_1$-$C_4$-alkyl; or —C(O)—O—$C_1$-$C_4$-alkyl-O-phenyl, where the phenyl radical may optionally be substituted by one to three radicals from the group consisting of halogen and $C_1$-$C_4$-alkyl;

$R^{19}$ is hydrogen, $C_1$-$C_6$-alkyl, $C_3$-$C_6$-cycloalkyl, $C_3$-$C_6$-alkenyl, $C_3$-$C_6$-alkynyl, $C_3$-$C_6$-haloalkenyl, $C_3$-$C_6$-haloalkynyl, where the alkyl and cycloalkyl radicals mentioned may be partially or fully halogenated and/or may carry one to three of the following groups: cyano, hydroxyl, $C_3$-$C_6$-cycloalkyl, $C_1$-$C_4$-alkoxy, $C_1$-$C_4$-alkylthio, di($C_1$-$C_4$-alkyl)amino, $C_1$-$C_4$-alkylcarbonyl, hydroxycarbonyl, $C_1$-$C_4$-alkoxycarbonyl, aminocarbonyl, $C_1$-$C_4$-alkylaminocarbonyl, di($C_1$-$C_4$-alkyl) amino-carbonyl or $C_1$-$C_4$-alkylcarbonyloxy; or phenyl, phenyl-$C_1$-$C_6$-alkyl, heterocyclyl or heterocyclyl-$C_1$-$C_6$-alkyl, where the phenyl and the heterocyclyl radicals of the 4 last-mentioned substituents may be partially or fully halogenated, and/or may carry one to three of the following groups: nitro, cyano, $C_1$-$C_4$-alkyl, $C_1$-$C_4$-haloalkyl, $C_1$-$C_4$-alkoxy or $C_1$-$C_4$-haloalkoxy;

$R^{20}$ is $C_1$-$C_6$-alkyl, $C_1$-$C_6$-haloalkyl or phenyl, where the phenyl radical may be partially or fully halogenated and/or may carry one to three of the following groups: $C_1$-$C_6$-alkyl, $C_1$-$C_6$-haloalkyl or $C_1$-$C_6$-alkoxy;

or an agriculturally useful salt thereof.

2. The benzoyl-substituted phenylalanineamide of the formula I according to claim 1, where $R^1$ is halogen or $C_1$-$C_6$-haloalkyl.

3. The benzoyl-substituted phenylalanineamide of the formula according to claim 1, where $R^2$ and $R^3$ independently of one another are hydrogen, halogen or $C_1$-$C_6$-haloalkyl.

4. The benzoyl-substituted phenylalanineamide of the formula I according to claim 1, where $R^4$, $R^5$, $R^6$, $R^7$, $R^{10}$, $R^{13}$, $R^{14}$ and $R^{15}$ are hydrogen.

5. The benzoyl-substituted phenylalanineamide of the formula I according to claim 1, where $R^9$ is $OR^{16}$.

6. A process for preparing benzoyl-substituted phenylalanineamides of the formula I according to claim 1, which comprises reacting phenylalanines of the formula V

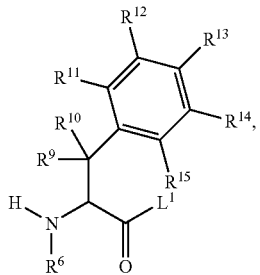

where $R^6$ and $R^9$ to $R^{15}$ are as defined in claim 1 and $L^1$ is a nucleophilically displaceable leaving group, with benzoic acids or benzoic acid derivatives of the formula IV

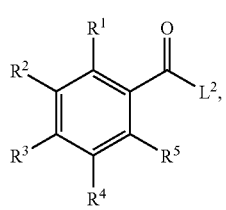

where $R^1$ to $R^5$ are as defined in claim 1 and $L^2$ is a nucleophilically displaceable leaving group to give the corresponding benzoyl derivatives of the formula III

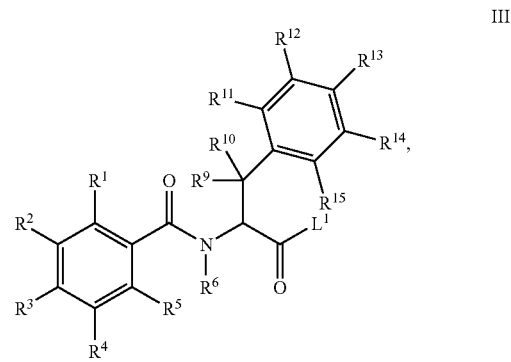

where $R^1$ to $R^6$ and $R^9$ to $R^{15}$ are as defined in claim 1 and $L^1$ is a nucleophilically displaceable leaving group and then reacting the resulting benzoyl derivatives of the formula III with an amine of the formula II $HNR^7R^8$  II, where $R^7$ and $R^8$ are as defined in claim 1.

7. The process of claim 6 for preparing benzoyl-substituted phenylalanineamides of the formula I, where $R^9$ is hydroxyl and $R^{10}$ is hydrogen, which comprises preparing benzoyl derivatives of the formula III where $R^9$ is hydroxyl and $R^{10}$ is hydrogen by acylating keto compounds of the formula XIII

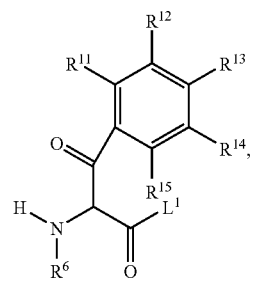

where $R^6$ and $R^{11}$ to $R^{15}$ are as defined in claim 6 and $L^1$ is a nucleophilically displaceable leaving group with benzoic acids/benzoic acid derivatives of the formula IV to produce N-acyl keto compounds of the formula XII

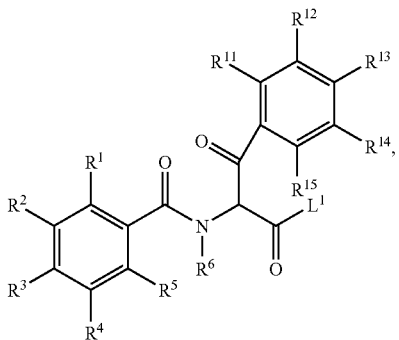

where $R^1$ to $R^6$ and $R^{11}$ to $R^{15}$ are as defined in claim 6 and $L^1$ is a nucleophilically displaceable leaving group, and thereafter reducing the keto group.

8. A herbicidal composition comprising a herbicidally effective amount of at least one benzoyl-substituted phenylalanineamide of the formula I

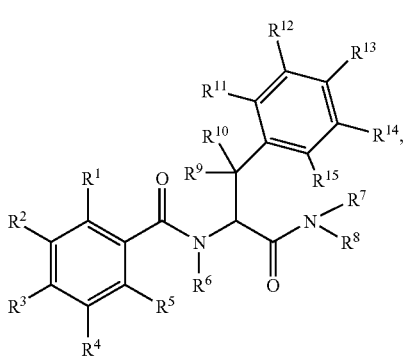

in which the variables are as defined below:

$R^1$ is halogen, cyano, $C_1$-$C_6$-alkyl, $C_1$-$C_6$-haloalkyl, $C_1$-$C_6$-haloalkoxy, nitro, hydroxycarbonyl, $C_1$-$C_6$-alkoxycarbonyl, $C_1$-$C_6$-haloalkylthio, or phenyl;

$R^2$, $R^3$, $R^4$, $R^5$ are hydrogen, halogen, cyano, $C_1$-$C_6$-alkyl, $C_1$-$C_6$-haloalkyl, $C_1$-$C_6$-alkoxy, $C_1$-$C_6$-haloalkoxy, nitro, amino, $C_1$-$C_6$-alkylamino, di($C_1$-$C_6$-alkyl)amino, $C_1$-$C_6$-alkylthio or $C_1$-$C_6$-alkoxycarbonyl;

$R^6$, $R^7$ are hydrogen, hydroxyl or $C_1$-$C_6$-alkoxy;

$R^8$ is $C_1$-$C_6$-alkyl, $C_1$-$C_4$-cyanoalkyl or $C_1$-$C_6$-haloalkyl;

$R^9$ is $OR^6$, $SR^{17}$ or $NR^{18}R^{19}$;

$R^{10}$ is hydrogen or $C_1$-$C_6$-alkyl;

$R^{11}$, $R^{12}$ are hydrogen, halogen, cyano, $C_1$-$C_6$-alkyl, $C_1$-$C_6$-haloalkyl, hydroxyl, $C_1$-$C_6$-alkoxy, $C_1$-$C_6$-haloalkoxy, hydroxyl, nitro, hydroxy-$C_1$-$C_4$-alkyl, $C_1$-$C_6$-alkoxy-$C_1$-$C_4$-alkyl, tri($C_1$-$C_6$-alkyl)silyloxy-$C_1$-$C_4$-alkyl, $C_1$-$C_4$-alkylthio, (hydroxycarbonyl)-$C_1$-$C_6$-alkyl, ($C_1$-$C_6$-alkoxycarbonyl)-$C_1$-$C_6$-alkyl, (hydroxycarbonyl)-$C_2$-$C_6$-alkenyl, ($C_1$-$C_6$-alkoxycarbonyl)-$C_2$-$C_6$-alkenyl, (hydroxycarbonyl)-$C_1$-$C_4$-alkoxy, ($C_1$-$C_4$-alkoxycarbonyl)-$C_1$-$C_4$-alkoxy, ($C_1$-$C_4$-alkylcarbonyl)oxy-$C_1$-$C_4$-alkyl, hydroxycarbonyl-$C_1$-$C_4$-alkoxy-$C_1$-$C_4$-alkyl, ($C_1$-$C_4$-alkylsulfonyl)oxy-$C_1$-$C_4$-alkyl, $C_1$-$C_4$-alkyl-O—C(O)-[$C_1$-$C_4$-alkyl-O]$_3$—$C_1$-$C_4$-alkyl, carbamoyloxy-$C_1$-$C_4$-alkyl, ($C_1$-$C_4$-alkylamino)carbonyl]oxy-$C_1$-$C_4$-alkyl, [di($C_1$-$C_4$-alkyl)aminocarbonyl]oxy-$C_1$-$C_4$-alkyl, [($C_1$-$C_4$-haloalkylsulfonyl)aminocarbonyl]oxy-$C_1$-$C_4$-alkyl, benzyloxy, where the phenyl ring may be substituted by 1 to 3 radicals from the group consisting of halogen and $C_1$-$C_4$-alkyl, amino, $C_1$-$C_4$-alkylamino, di($C_1$-$C_4$-alkyl)amino, ($C_1$-$C_4$-alkylsulfonyl)amino, $C_1$-$C_4$-(haloalkylsulfonyl)amino, ($C_1$-$C_4$-alkylcarbonyl)amino, carbamoylamino, ($C_1$-$C_4$-alkylamino)carbonylamino, [di($C_1$-$C_4$-alkyl)amino]carbonylamino, [($C_1$-$C_4$-haloalkylsulfonyl)aminocarbonyl]-amino, phenyl or heterocyclyl, where the phenyl and the heterocyclyl radical of the two last-mentioned substituents may carry one to three radicals from the following group: halogen, nitro, $C_1$-$C_4$-alkyl, $C_1$-$C_4$-haloalkyl, hydroxycarbonyl and $C_1$-$C_6$-alkoxycarbonyl;

$R^{13}$, $R^{14}$, $R^{15}$ are hydrogen, halogen, cyano, $C_1$-$C_6$-alkyl, $C_1$-$C_6$-haloalkyl, $C_1$-$C_6$-alkoxy, $C_1$-$C_6$-haloalkoxy, nitro, hydroxyl, $C_1$-$C_4$-alkylthio or benzyloxy;

$R^{16}$, $R^{17}$, $R^{18}$ are hydrogen, $C_1$-$C_6$-alkyl, tri($C_1$-$C_6$-alkyl)silyl, $C_3$-$C_6$-cycloalkyl, $C_3$-$C_6$-alkenyl, $C_3$-$C_6$-alkynyl, $C_3$-$C_6$-haloalkenyl, $C_3$-$C_6$-haloalkynyl, formyl, $C_1$-$C_6$-alkylcarbonyl, $C_3$-$C_6$-cycloalkylcarbonyl, $C_2$-$C_6$-alkenylcarbonyl, $C_2$-$C_6$-alkynylcarbonyl, $C_1$-$C_6$-alkoxycarbonyl, $C_3$-$C_6$-alkenyloxycarbonyl, $C_3$-$C_6$-alkynyloxycarbonyl $C_1$-$C_6$-alkylaminocarbonyl, $C_3$-$C_6$-alkenylaminocarbonyl, $C_3$-$C_6$-alkynylaminocarbonyl, $C_1$-$C_6$-alkylsulfonylaminocarbonyl, $C_1$-$C_6$-haloalkylsulfonylaminocarbonyl, di($C_1$-$C_6$-alkyl)aminocarbonyl, N—($C_3$-$C_6$-alkenyl)-N—($C_1$-$C_6$-alkyl) aminocarbonyl, N—($C_3$-$C_6$-alkynyl)-N—($C_1$-$C_6$-alkyl) aminocarbonyl, N—($C_1$-$C_6$-alkoxy)-N—($C_1$-$C_6$-alkyl) aminocarbonyl, N—($C_3$-$C_6$-alkenyl)-N—($C_1$-$C_6$-alkoxy)aminocarbonyl, N—($C_3$-$C_6$-alkynyl)-N—($C_1$-$C_6$-alkoxy)aminocarbonyl, di($C_1$-$C_6$-alkyl) aminothiocarbonyl, $C_1$-$C_6$-alkylcarbonyl-$C_1$-$C_6$-alkyl, $C_1$-$C_6$-alkoxyimino-$C_1$-$C_6$-alkyl, N—($C_1$-$C_6$-alkylamino)imino-$C_1$-$C_6$-alkyl or N-(di-$C_1$-$C_6$-alkylamino) imino-$C_1$-$C_6$-alkyl, where the alkyl, cycloalkyl and alkoxy radicals mentioned may be partially or fully halogenated and/or may carry one to three of the following groups: cyano, hydroxyl, $C_3$-$C_6$-cycloalkyl, $C_1$-$C_4$-alkoxy, $C_1$-$C_4$-alkylthio, di($C_1$-$C_4$-alkyl)amino, $C_1$-$C_4$-alkylcarbonyl, hydroxycarbonyl, $C_1$-$C_4$-alkoxycarbonyl, aminocarbonyl, $C_1$-$C_4$-alkylaminocarbonyl, di($C_1$-$C_4$-alkyl)-aminocarbonyl or $C_1$-$C_4$-alkylcarbonyloxy;

phenyl, phenyl-$C_1$-$C_6$-alkyl, phenylcarbonyl, phenylcarbonyl-$C_1$-$C_6$-alkyl, phenoxycarbonyl, phenylaminocarbonyl, phenylsulfonylaminocarbonyl, N—($C_1$-$C_6$-alkyl)-N-(phenyl)aminocarbonyl, phenyl-$C_1$-$C_6$-alkylcarbonyl, heterocyclyl, heterocyclyl-$C_1$-$C_6$-alkyl, heterocyclylcarbonyl, heterocyclylcarbonyl-$C_1$-$C_6$-alkyl, heterocyclyloxycarbonyl, heterocyclylaminocarbonyl, heterocyclylsulfonylaminocarbonyl, N—($C_1$-$C_6$-alkyl)-N-(heterocyclyl) aminocarbonyl or heterocyclyl-$C_1$-$C_6$-alkylcarbonyl, where the phenyl and the heterocyclyl radicals may be partially or fully halogenated and/or may carry one to three of the following groups: nitro, cyano, $C_1$-$C_4$-alkyl, $C_1$-$C_4$-haloalkyl, $C_1$-$C_4$-alkoxy or $C_1$-$C_4$-haloalkoxy $SO_2R^{20}$; —C(O)—[$C_1$-$C_4$-alkyl-O]$_3$—$C_1$-$C_4$-alkyl; or —C(O)—O—$C_1$-$C_4$-alkyl-O-phenyl, where the phenyl radical may optionally be substituted by one to three radicals from the group consisting of halogen and $C_1$-$C_4$-alkyl;

$R^{19}$ is hydrogen, $C_1$-$C_6$-alkyl, $C_3$-$C_6$-cycloalkyl, $C_3$-$C_6$-alkenyl, $C_3$-$C_6$-alkynyl, $C_3$-$C_6$-haloalkenyl, $C_3$-$C_6$-haloalkynyl, where the alkyl and cycloalkyl radicals mentioned may be partially or fully halogenated and/or may carry one to three of the following groups: cyano, hydroxyl, $C_3$-$C_6$-cycloalkyl, $C_1$-$C_9$ alkoxy, $C_1$-$C_4$-alkylthio, di($C_1$-$C_4$-alkyl)amino, $C_1$-$C_4$-alkylcarbonyl, hydroxycarbonyl, $C_1$-$C_4$-alkoxycarbonyl, aminocarbonyl, $C_1$-$C_4$-alkylaminocarbonyl, di($C_1$-$C_4$-alkyl)amino-carbonyl or $C_1$-$C_4$-alkylcarbonyloxy; or phenyl, phenyl-$C_1$-$C_6$-alkyl, heterocyclyl or heterocyclyl-$C_1$-$C_6$-alkyl, where the phenyl and the heterocyclyl radicals of the 4 last-mentioned substituents may be partially or fully halogenated, and/or may carry one to three of the following groups: nitro, cyano, $C_1$-$C_4$-alkyl, $C_1$-$C_4$-haloalkyl, $C_1$-$C_4$-alkoxy or $C_1$-$C_4$-haloalkoxy;

$R^{20}$ is $C_1$-$C_6$-alkyl, $C_1$-$C_6$-haloalkyl or phenyl, where the phenyl radical may be partially or fully halogenated and/or may carry one to three of the following groups: $C_1$-$C_6$-alkyl, $C_1$-$C_6$-haloalkyl or $C_1$-$C_4$-alkoxy;

or an agriculturally useful salt thereof and auxiliaries customary for formulating crop protection agents.

9. A process for preparing herbicidal compositions comprising mixing a herbicidally effective amount of at least one benzoyl-substituted phenylalanineamide of the formula I

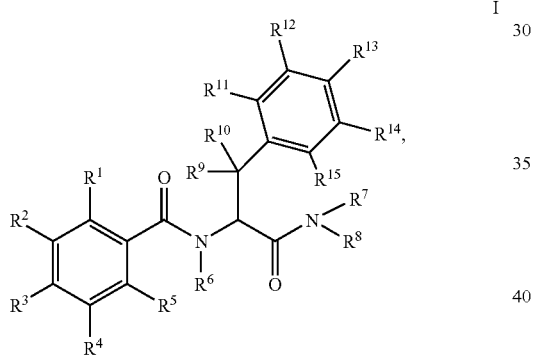

in which the variables are as defined below:

$R^1$ is halogen, cyano, $C_1$-$C_6$-alkyl, $C_1$-$C_6$-haloalkyl, $C_1$-$C_6$-haloalkoxy, nitro, hydroxycarbonyl, $C_1$-$C_6$-alkoxycarbonyl, $C_1$-$C_6$-haloalkylthio, or phenyl;

$R^2$, $R^3$, $R^4$, $R^5$ are hydrogen, halogen, cyano, $C_1$-$C_6$-alkyl, $C_1$-$C_6$-haloalkyl, $C_1$-$C_6$-alkoxy, $C_1$-$C_6$-haloalkoxy, nitro, amino, $C_1$-$C_6$-alkylamino, di($C_1$-$C_6$-amino $C_1$-$C_6$-alkylthio or $C_1$-$C_6$-alkoxycarbonyl;

$R^6$, $R^7$ are hydrogen, hydroxyl or $C_1$-$C_6$-alkoxy;

$R^8$ is $C_1$-$C_6$-alkyl, $C_1$-$C_4$-cyanoalkyl or $C_1$-$C_6$-haloalkyl;

$R^9$ is $OR^{16}$, $SR^{17}$ or $NR^{18}R^{19}$;

$R^{10}$ is hydrogen or $C_1$-$C_6$-alkyl;

$R^{11}$, $R^{12}$ are hydrogen, halogen, cyano, $C_1$-$C_6$-alkyl, $C_1$-$C_6$-haloalkyl, hydroxyl, $C_1$-$C_6$-alkoxy, $C_1$-$C_6$-haloalkoxy, hydroxyl, nitro, hydroxy-$C_1$-$C_4$-alkyl, $C_1$-$C_6$-alkoxy-$C_1$-$C_4$-alkyl, tri($C_1$-$C_6$-alkyl)silyloxy-$C_1$-$C_4$-alkyl, $C_1$-$C_4$-alkylthio, (hydroxycarbonyl)-$C_1$-$C_6$-alkyl, ($C_1$-$C_6$-alkoxycarbonyl)-$C_1$-$C_6$-alkyl, (hydroxycarbonyl)-$C_2$-$C_6$-alkenyl, ($C_1$-$C_6$-alkoxycarbonyl)-$C_2$-$C_6$-alkenyl, (hydroxycarbonyl)-$C_1$-$C_4$-alkoxycarbonyl-$C_1$-$C_4$-alkoxy, ($C_1$-$C_4$-alkylcarbonyl)oxy-$C_1$-$C_4$-alkyl, hydroxycarbonyl-$C_1$-$C_4$-alkoxy-$C_1$-$C_4$-alkyl, ($C_1$-$C_4$-alkylsulfonyl)oxy-$C_1$-$C_4$-alkyl, $C_1$-$C_4$-alkyl-O—C(O)-[$C_1$-$C_4$-alkyl-O]$_3$—$C_1$-$C_4$-alkyl, carbamoyloxy-$C_1$-$C_4$-alkyl, ($C_1$-$C_4$-alkylaminocarbonyl)oxy-$C_1$-$C_4$-alkyl, [di($C_1$-$C_4$-alkyl)aminocarbonyl]oxy-$C_1$-$C_4$-alkyl, [($C_1$-$C_4$-haloalkylsulfonyl)aminocarbonyl]oxy-$C_1$-$C_4$-alkyl, benzyloxy, where the phenyl ring may be substituted by 1 to 3 radicals from the group consisting of halogen and $C_1$-$C_4$-alkyl, amino, $C_1$-$C_4$-alkylamino, di($C_1$-$C_4$-alkyl)amino, ($C_1$-$C_4$-alkylsulfonyl)amino, $C_1$-$C_4$-(haloalkylsulfonyl)amino, ($C_1$-$C_4$-alkylcarbonyl)amino, carbamoylamino, ($C_1$-$C_4$-alkylamino)carbonylamino, [di($C_1$-$C_4$-alkyl)amino]carbonylamino, [($C_1$-$C_4$-haloalkylsulfonyl)aminocarbonyl]-amino, phenyl or heterocyclyl, where the phenyl and the heterocyclyl radical of the two last-mentioned substituents may carry one to three radicals from the following group: halogen, nitro, $C_1$-$C_4$-alkyl, $C_1$-$C_4$-haloalkyl, hydroxycarbonyl and $C_1$-$C_6$-alkoxycarbonyl;

$R^{13}$, $R^{14}$, $R^{15}$ are hydrogen, halogen, cyano, $C_1$-$C_6$-alkyl, $C_1$-$C_6$-haloalkyl, $C_1$-$C_6$-alkoxy, $C_1$-$C_6$-haloalkoxy, nitro, hydroxyl, $C_1$-$C_4$-alkylthio or benzyloxy;

$R^{16}$, $R^{17}$, $R^{18}$ are hydrogen, $C_1$-$C_6$-alkyl, tri($C_1$-$C_6$-alkyl)silyl, $C_3$-$C_6$-cycloalkyl, $C_3$-$C_6$-alkenyl, $C_3$-$C_6$-alkynyl, $C_3$-$C_6$-haloalkenyl, $C_3$-$C_6$-haloalkynyl, formyl, $C_1$-$C_6$-alkylcarbonyl, $C_3$-$C_6$-cycloalkylcarbonyl, $C_2$-$C_6$-alkenylcarbonyl, $C_2$-$C_6$-alkynylcarbonyl, $C_1$-$C_6$-alkoxycarbonyl, $C_3$-$C_6$-alkenyloxycarbonyl, $C_3$-$C_6$-alkynyloxycarbonyl, $C_1$-$C_6$-alkylaminocarbonyl, $C_3$-$C_6$-alkenylaminocarbonyl, $C_3$-$C_6$-alkynylaminocarbonyl, $C_1$-$C_6$-alkylsulfonylaminocarbonyl, $C_1$-$C_6$-haloalkylsulfonylaminocarbonyl, di($C_1$-$C_6$-alkyl)aminocarbonyl, N—($C_3$-$C_6$-alkenyl)-N—($C_1$-$C_6$-alkyl)aminocarbonyl, N—($C_3$-$C_6$-alkynyl)-N—($C_1$-$C_6$-alkyl)aminocarbonyl, N—($C_1$-$C_6$-alkoxy)-N—($C_1$-$C_6$-alkyl)aminocarbonyl, N—($C_3$-$C_6$-alkenyl)-N—($C_1$-$C_6$-alkoxy)aminocarbonyl, N—($C_3$-$C_6$-alkynyl)-N—($C_1$-$C_6$-alkoxy)aminocarbonyl, di($C_1$-$C_6$-alkyl)aminothiocarbonyl, $C_1$-$C_6$-alkylcarbonyl-$C_1$-$C_6$-alkyl, $C_1$-$C_6$-alkoxyimino-$C_1$-$C_6$-alkyl, N—($C_1$-$C_6$-alkylamino)imino-$C_1$-$C_6$-alkyl or N-(di-$C_1$-$C_6$-alkylamino)imino-$C_1$-$C_6$-alkyl, where the alkyl, cycloalkyl and alkoxy radicals mentioned may be partially or fully halogenated and/or may carry one to three of the following groups: cyano, hydroxyl, $C_3$-$C_6$-cycloalkyl, $C_1$-$C_4$-alkoxy, $C_1$-$C_4$-alkylthio, di($C_1$-$C_4$-alkyl)amino, $C_1$-$C_4$-alkylcarbonyl, hydroxycarbonyl, $C_1$-$C_4$-alkoxycarbonyl, aminocarbonyl, $C_1$-$C_4$-alkylaminocarbonyl, di($C_1$-$C_4$-alkyl)-aminocarbonyl or $C_1$-$C_4$-alkylcarbonyloxy;

phenyl, phenyl-$C_1$-$C_6$-alkyl, phenylcarbonyl, phenylcarbonyl-$C_1$-$C_6$-alkyl, phenoxycarbonyl, phenylaminocarbonyl, phenylsulfonylaminocarbonyl, N—($C_1$-$C_6$-alkyl)-N-(phenyl)aminocarbonyl, phenyl-$C_1$-$C_6$-alkylcarbonyl, heterocyclyl, heterocyclyl-$C_1$-$C_6$-alkyl, heterocyclylcarbonyl, heterocyclylcarbonyl-$C_1$-$C_6$-alkyl, heterocyclyloxycarbonyl, heterocyclylaminocarbonyl, heterocyclylsulfonylaminocarbonyl, N—($C_1$-$C_6$-alkyl)-N-(heterocyclyl)aminocarbonyl or heterocyclyl-$C_1$-$C_6$-alkylcarbonyl, where the phenyl and the heterocyclyl radicals may be partially or fully halogenated and/or may carry one to three of the following groups: nitro, cyano, $C_1$-$C_4$-alkyl, $C_1$-$C_4$-haloalkyl, $C_1$-$C_4$-alkoxy or $C_1$-$C_4$-haloalkoxy $SO_2R^{20}$; —C(O)—[$C_1$-$C_4$-alkyl-O]$_3$—$C_1$-$C_4$-alkyl; or —C(O)—O—$C_1$-$C_4$-alkyl-O-phenyl, where the phenyl radical may optionally be substituted by one to three radicals from the group consisting of halogen and $C_1$-$C_4$-alkyl;

$R^{19}$ is hydrogen, $C_1$-$C_6$-alkyl, $C_3$-$C_6$-cycloalkyl, $C_3$-$C_6$-alkenyl, $C_3$-$C_6$-alkynyl, $C_3$-$C_6$-haloalkenyl, $C_3$-$C_6$-haloalkynyl, where the alkyl and cycloalkyl radicals mentioned may be partially or fully halogenated and/or may carry one to three of the following groups: cyano, hydroxyl, $C_3$-$C_6$-cycloalkyl, $C_1$-$C_4$-alkoxy, $C_1$-$C_4$-alkylthio, di($C_1$-$C_4$-alkyl)amino, $C_1$-$C_4$-alkylcarbonyl, hydroxycarbonyl, $C_1$-$C_4$-alkoxycarbonyl, aminocarbonyl, $C_1$-$C_4$-alkylaminocarbonyl, di($C_1$-$C_4$-alkyl)amino-carbonyl or $C_1$-$C_4$-alkylcarbonyloxy; or phenyl, phenyl-$C_1$-$C_6$-alkyl, heterocyclyl or heterocyclyl-$C_1$-$C_6$-alkyl, where the phenyl and the heterocyclyl radicals of the 4 last-mentioned substituents may be partially or fully halogenated, and/or may carry one to three of the following groups: nitro, cyano, $C_1$-$C_4$-alkyl, $C_1$-$C_4$-haloalkyl, $C_1$-$C_4$-alkoxy or $C_1$-$C_4$-haloalkoxy;

$R^{20}$ is $C_1$-$C_6$-alkyl, $C_1$-$C_6$-haloalkyl or phenyl, where the phenyl radical may be partially or fully halogenated and/or may carry one to three of the following groups: $C_1$-$C_6$-alkyl, $C_1$-$C_6$-haloalkyl or $C_1$-$C_6$-alkoxy;

or an agriculturally useful salt thereof with auxiliaries customary for formulating crop protection agents.

10. A method for controlling unwanted vegetation, which comprises allowing a herbicidally effective amount of at least one benzoyl-substituted phenylalanineamide or an agriculturally useful salt thereof of claim 1 to act on plants, their habitat and/or on seed.

11. The method of claim 10, wherein the application rate of the compound of formula I or salt thereof is from 0.001 to 3.0 kg/ha.

12. The method of claim 11, wherein the application rate is 0.01 to 1.0 kg/ha.

13. The phenylalanineamide or salt thereof of claim 1, wherein $R^1$ is F; $R^2$, $R^3$, $R^4$, $R^5$, $R^6$, $R^7$, $R^{10}$, $R^{14}$ and $R^{15}$ are all H; and $R^8$ is $CH_3$.

* * * * *